(12) United States Patent
Vetter

(10) Patent No.: US 10,231,750 B2
(45) Date of Patent: Mar. 19, 2019

(54) EXCISIONAL DEVICE DISTAL WORKING END ACTUATION MECHANISM AND METHOD

(71) Applicant: TRANSMED7, LLC, Portola Valley, CA (US)

(72) Inventor: James William Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 344 days.

(21) Appl. No.: 14/599,481

(22) Filed: Jan. 17, 2015

(65) Prior Publication Data

US 2016/0089208 A1    Mar. 31, 2016

Related U.S. Application Data

(60) Provisional application No. 62/063,848, filed on Oct. 14, 2014, provisional application No. 62/056,983, filed on Sep. 29, 2014.

(51) Int. Cl.
*A61B 10/02* (2006.01)
*A61B 10/06* (2006.01)
(Continued)

(52) U.S. Cl.
CPC ...... *A61B 17/3207* (2013.01); *A61B 10/0266* (2013.01); *A61B 17/3201* (2013.01);
(Continued)

(58) Field of Classification Search
CPC .... A61B 2017/2939; A61B 2017/2937; A61B 2017/2944; A61B 2017/320024;
(Continued)

(56) References Cited

U.S. PATENT DOCUMENTS 1,493,240 A    5/1924    Bohn
2,751,908 A    6/1956    Wallace
(Continued)

FOREIGN PATENT DOCUMENTS

CA    2008190    7/1990

OTHER PUBLICATIONS

International Search Report dated Feb. 26, 2013 in PCT/US12/60149.
(Continued)

*Primary Examiner* — Darwin P Erezo
*Assistant Examiner* — Katherine H Schwiker
(74) *Attorney, Agent, or Firm* — Young Law Firm, P.C.

(57) ABSTRACT

An excisional device may comprise a sheath; a tubular element configured for rotation with the sheath; and an inner element configured for rotation and disposed at least partially within the tubular element. The inner element may comprise an articulable distal assembly configured to core through tissue in an open configuration and part-off cored tissue in a closed configuration. Differential rotation of the inner element with respect to the tubular element causes the articulable distal assembly to selectively assume the open and closed configurations. For example, lagging the rotation of the inner element relative to the rotation of the tubular element may control the articulable distal assembly to assume the open configuration whereas leading the rotation of the inner element relative to the rotation of the tubular element may control the articulable distal assembly to assume the closed configuration.

16 Claims, 42 Drawing Sheets

(51) Int. Cl.
*A61B 17/29* (2006.01)
*A61B 17/32* (2006.01)
*A61B 17/3205* (2006.01)
*A61B 17/3207* (2006.01)
*A61B 17/3201* (2006.01)
*A61B 17/00* (2006.01)

(52) U.S. Cl.
CPC .......... *A61B 17/3205* (2013.01); *A61B 10/06* (2013.01); *A61B 17/32053* (2013.01); *A61B 17/320068* (2013.01); *A61B 2010/0208* (2013.01); *A61B 2017/00685* (2013.01); *A61B 2017/2903* (2013.01); *A61B 2017/320064* (2013.01); *A61B 2217/005* (2013.01)

(58) Field of Classification Search
CPC ....... A61B 2017/320028; A61B 2017/320032; A61B 2017/320052; A61B 2017/320064; A61B 10/02; A61B 10/0233; A61B 10/0266; A61B 10/06; A61B 10/04; A61B 2010/0208; A61B 2010/0225; A61B 10/0275; A61B 17/32002
USPC .......................................................... 606/170
See application file for complete search history.

(56) References Cited

U.S. PATENT DOCUMENTS

| | | | |
|---|---|---|---|
| 4,522,206 A | 6/1985 | Whipple et al. | |
| 4,653,496 A | 3/1987 | Bundy et al. | |
| 4,682,606 A | 7/1987 | DeCaprio | |
| 5,052,402 A | 10/1991 | Bencini et al. | |
| 5,074,311 A | 12/1991 | Hasson | |
| 5,174,300 A | 12/1992 | Bales et al. | |
| 5,251,641 A | 10/1993 | Xavier | |
| 5,259,365 A | 11/1993 | Nishikori et al. | |
| 5,415,169 A | 5/1995 | Siczek et al. | |
| 5,507,296 A | 4/1996 | Bales et al. | |
| 5,526,822 A | 6/1996 | Burbank et al. | |
| 5,573,008 A | 11/1996 | Robinson et al. | |
| 5,609,152 A | 3/1997 | Pellegrino et al. | |
| 5,649,547 A | 7/1997 | Ritchart et al. | |
| 5,762,069 A | 6/1998 | Kelleher et al. | |
| 5,827,305 A * | 10/1998 | Gordon .............. | A61B 10/0266 606/159 |
| 5,871,453 A | 2/1999 | Banik et al. | |
| 5,873,886 A | 2/1999 | Larsen et al. | |
| 5,976,164 A | 11/1999 | Bencini et al. | |
| 6,083,237 A | 7/2000 | Huitema et al. | |
| 6,086,543 A | 7/2000 | Anderson et al. | |
| 6,139,508 A | 10/2000 | Simpson et al. | |
| 6,142,957 A | 11/2000 | Diamond et al. | |
| 6,149,607 A | 11/2000 | Simpson et al. | |
| 6,193,673 B1 | 2/2001 | Viola et al. | |
| 6,383,145 B1 | 5/2002 | Worm et al. | |
| 6,391,043 B1 | 5/2002 | Moll et al. | |
| 6,582,451 B1 | 6/2003 | Marucci et al. | |
| 6,599,309 B1 | 7/2003 | Gilman | |
| 6,655,542 B2 | 12/2003 | Koshikawa et al. | |
| 7,008,381 B2 | 3/2006 | Janssens | |
| 7,641,667 B2 | 1/2010 | Sample | |
| 7,762,960 B2 | 7/2010 | Timberlake et al. | |
| 2001/0034495 A1 | 10/2001 | Wilson et al. | |
| 2002/0038129 A1 * | 3/2002 | Peters .............. | A61B 17/32002 606/167 |
| 2002/0165580 A1 | 11/2002 | Zwiefel et al. | |
| 2002/0169472 A1 * | 11/2002 | Douk .............. | A61B 17/12022 606/200 |
| 2003/0032955 A1 | 2/2003 | Muller | |
| 2003/0114773 A1 | 6/2003 | Janssens | |
| 2004/0073139 A1 | 4/2004 | Hirsch et al. | |
| 2005/0054972 A1 * | 3/2005 | Adams .............. | A61B 17/1688 604/22 |
| 2005/0070885 A1 | 5/2005 | Nobis et al. | |
| 2005/0209564 A1 | 9/2005 | Bonner et al. | |
| 2006/0264927 A1 * | 11/2006 | Ryan ................ | A61B 17/32002 606/45 |
| 2007/0219459 A1 | 9/2007 | Cohen | |
| 2007/0255311 A1 | 11/2007 | Hiraoka | |
| 2007/0270712 A1 | 11/2007 | Wiksell et al. | |
| 2008/0045860 A1 | 2/2008 | Miller et al. | |
| 2009/0204023 A1 | 8/2009 | Goldenberg | |
| 2009/0264910 A1 | 10/2009 | Laufer | |
| 2009/0306689 A1 | 10/2009 | Welty et al. | |
| 2009/0287114 A1 | 11/2009 | Lee | |
| 2009/0299220 A1 | 12/2009 | Field et al. | |
| 2010/0078296 A1 | 4/2010 | Lapeyre et al. | |
| 2010/0121153 A1 | 5/2010 | To | |
| 2010/0234866 A1 * | 9/2010 | Arcenio ............. | A61B 17/1671 606/170 |
| 2010/0280407 A1 * | 11/2010 | Polster ............... | A61B 10/0266 600/566 |
| 2010/0312141 A1 | 12/2010 | Keast et al. | |
| 2011/0125054 A1 | 5/2011 | Clements et al. | |
| 2011/0132961 A1 | 6/2011 | Whitman et al. | |
| 2011/0245716 A1 | 10/2011 | Flatland et al. | |
| 2011/0245725 A1 | 10/2011 | Flatland et al. | |
| 2013/0041266 A1 | 2/2013 | Flebig | |
| 2013/0096459 A1 | 4/2013 | Vetter | |
| 2013/0190651 A1 | 7/2013 | Vetter | |
| 2014/0142602 A1 * | 5/2014 | Polo ...................... | A61B 10/02 606/174 |
| 2014/0213932 A1 | 7/2014 | Knoll et al. | |
| 2014/0336530 A1 | 11/2014 | Vetter et al. | |

OTHER PUBLICATIONS

Written Opinion of the International Searching Authority dated Feb. 26, 2013 in PCT/US12/60149.
USPTO Office Action dated Jan. 16, 2015 in related U.S. Appl. No. 13/651,393.
International Search Report and Written Opinion in PCT/US15/50868, dated Dec. 18, 2015.
USPTO Office Action dated Oct. 16, 2015 in U.S. Appl. No. 14/052,727.
USPTO Office Action dated Oct. 9, 2015 in U.S. Appl. No. 14/853,806.
International Search Report and Written Opinion in PCT/US14/039676, dated Apr. 23, 2015.
International Search Report and Written Opinion in PCT/US14/039688, dated Apr. 23, 2015.
USPTO Office Action dated Oct. 30, 2015 in U.S. Appl. No. 13/903,800.
USPTO Office Action dated Feb. 3, 2015 in related U.S. Appl. No. 13/973,898.
USPTO Office Action dated Apr. 13, 2015 in related U.S. Appl. No. 13/853,768.
USPTO Office Action dated Apr. 10, 2015 in related U.S. Appl. No. 13/853,636.
International Search Report and Written Opinion of International Searching Authority dated Apr. 16, 2015 in related PCT application PCT/US14/51945.
European Patent Office Extended Search Report dated Mar. 20, 2015 in related EP patent application 12839250.3.
International Search Report and Written Opinion of International Searching Authority dated Mar. 11, 2015 in related PCT application PCT/US14/55190.
International Search Report and Written Opinion of International Searching Authority dated Mar. 23, 2015 in related PCT application PCT/US14/39576.
International Search Report and Written Opinion of International Searching Authority dated Apr. 23, 2015 in related PCT application PCT/US14/39688.
USPTO Office Action dated Apr. 10, 2015 in related U.S. Appl. No. 13/853,837.
USPTO Office Action dated May 5, 2015 in related U.S. Appl. No. 13/973,898.

(56) References Cited

OTHER PUBLICATIONS

International Search Report and Written Opinion in PCT/US2016/013551, dated Mar. 17, 2016.

* cited by examiner

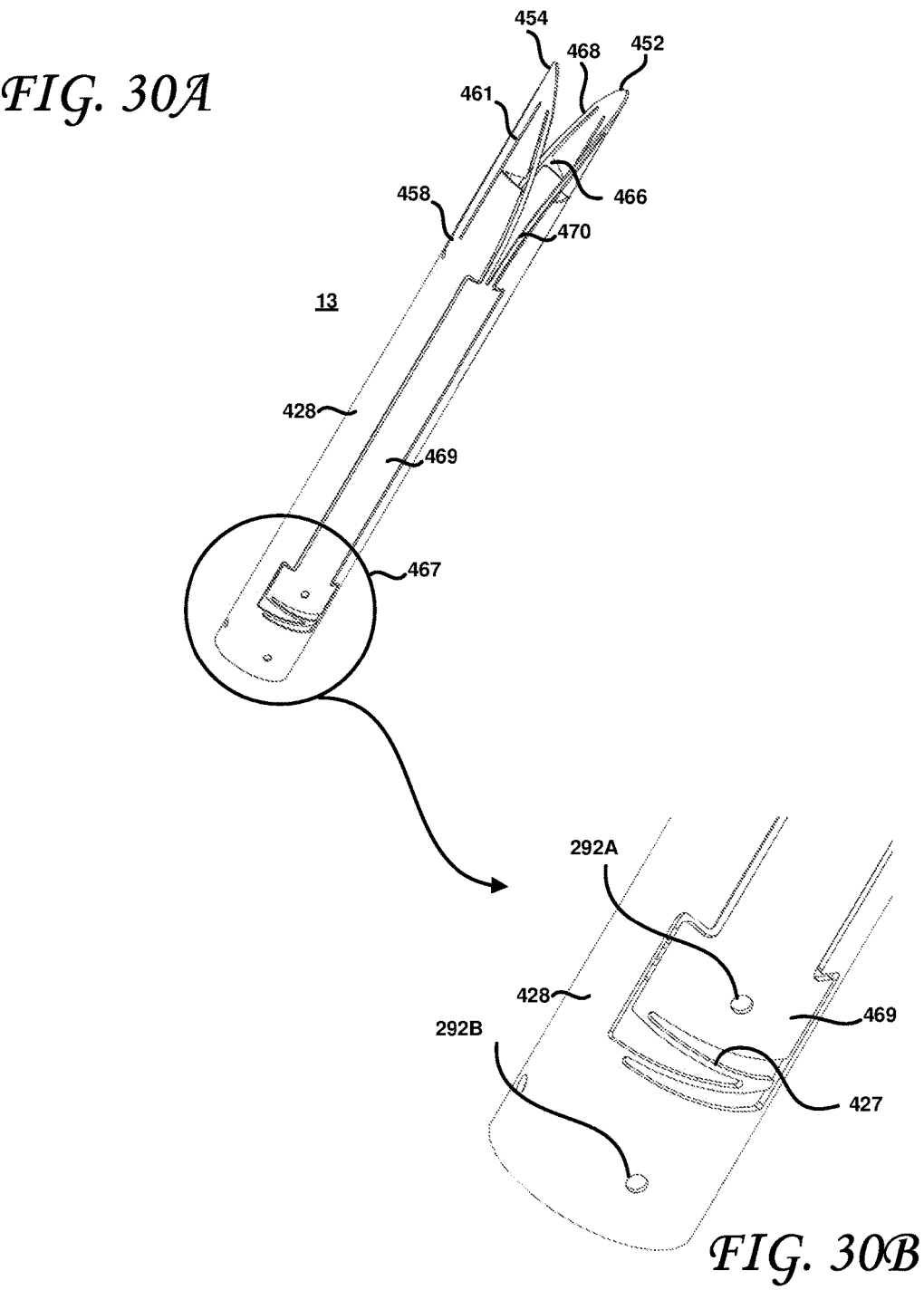

EXCISIONAL DEVICE DISTAL WORKING END ACTUATION MECHANISM AND METHOD

BACKGROUND

Embodiments relate to medical devices and methods. More particularly, embodiments relate to stereotactic table mounted or hand-held single insertion, multiple sample soft tissue excisional biopsy and coring devices and corresponding methods for retrieving multiple soft tissue biopsy samples using a single insertion.

SUMMARY

Embodiments are drawn to medical devices and methods that are used for core biopsy procedures. According to one embodiment, a biopsy corning/delivery device, also referred to herein as an excisional device, may be configured to retrieve multiple samples of normal and/or abnormal appearing tissues during a single insertion through the skin (percutaneous procedure). Embodiments may comprise structures and functionality for different phases of a multi-phase biopsy procedure, which may be performed by hand or through attachment to a stereotactic table or Magnetic Resonance Imaging (MRI) stage. For example, embodiments may comprise a pre-treatment of the area and/or of the abnormal tissue, or the delivery of tracer materials for tracking the potential spread or flow patterns of abnormal tissues (such as cancerous tissues) through the process of metastasis. Embodiments may also comprise an intra-procedure delivery of medications that may anesthetize tissues at the site, or that may deliver other therapeutic agents such as, for example, pro-coagulants. Embodiments may also be configured for the delivery of post-procedure materials such as medications, implantable materials for cosmetic purposes, marking elements and other implantable elements for later imaging reference, or other purposes. Embodiments may also be configured for imaging of the surrounding tissues during pre-operative, intra-operative, and/or post-operative phases of the device's clinical use. Embodiments may also be configured to allow for ablation of tissue during pre-, intra-, and/or post-operative phases. Embodiments of the biopsy device, along with associated related subcomponents described herein, may be configured to retrieve solid, contiguous and/or fragmented tissues as well as liquid and semi-solid tissues for analysis, diagnosis and treatment. Embodiments may be portable, disposable or reusable and may be electrically, mechanically and/or manually powered and operated.

BRIEF DESCRIPTION OF THE DRAWINGS

FIG. 30A shows a monolithic beak assembly of an excisional device according to one embodiment.

FIG. 30B shows a detail of a proximal end of a monolithic beak assembly of an excisional device according to one embodiment.

DETAILED DESCRIPTION

Figure 1:
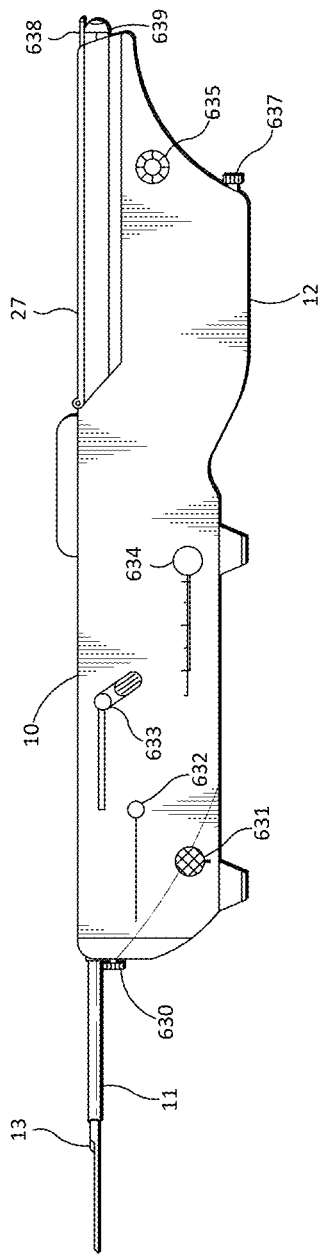
FIG. 1 is a perspective view of a core biopsy device according to one embodiment.

Reference will now be made in detail to the construction and operation of embodiments illustrated in the accompanying drawings. The following description is only exemplary of the embodiments described and shown herein. The embodiments, therefore, are not limited to these implementations, but may be realized by other implementations.

Core biopsy procedures have evolved from simple core needle biopsies comprising aspiration of fluids using a simple syringe and needle to devices having the capability to extract solid tissues for histopathological analysis. This more recent capability has proved to be a far more powerful way to diagnose diseases and abnormal tissue entities, some of which are extremely life threatening, and others, which may be more benign but nevertheless must be definitively distinguished from the more dangerous types of abnormalities, including pre-cancerous lesions, in-situ cancers, invasive cancers, and other space occupying lesions such as cystic lesions, serious infections and others. As core biopsy procedures have evolved into far more diagnostically powerful tools, they have displaced many of the more invasive open surgical procedures which, however, continue to be performed for diagnostic purposes based on the advantages of retrieving a sufficient volume of tissue with the preserved architecture that is so important in the diagnosis and treatment algorithm used by clinicians in addressing those abnormalities and diseases. One of the basic needs during a biopsy procedure is to accurately correlate tissue diagnoses with imaging diagnoses. In order to successfully accomplish this, it is important to know that the retrieved tissue actually and accurately represents the imaged abnormality. This is an aspect where many coring biopsy devices fall short. It is for this reason that open surgical diagnostic procedures and other invasive procedures continue to be performed. Other clinically significant limitations of core biopsy procedures include the manner in which the abnormal tissue is separated from the host organ, the manner in which the tissue is retrieved and handled during the procedure by the coring biopsy device, and the amount of biopsy artifact/damage imparted to the tissue specimens by the coring procedure and device. It is well known that the larger the caliber of the retrieved tissue samples, the better the correlation with the imaging abnormality, and thus the easier and more accurate, definitive and helpful the diagnosis. However, in order to retrieve larger caliber specimens, most biopsy devices have large outer diameters, leading to increased complications, pain and other adverse effects, due principally to the greater trauma associated with the larger bore devices. Moving these larger bore devices through the tissue is much more difficult, particularly without the help of an active mechanism to aid in smoother and more gradual advancement of the biopsy device. Additionally, the larger the caliber of the biopsy device, the more difficult it becomes to precisely visualize the biopsy device in relation to the target abnormality, especially for small lesions (on the order of about ½ cm to less than ¼ cm). Despite these limitations, more than 4-5 million diagnostic core biopsies are performed each year around the world in the breast alone, with as many as 2 million diagnostic breast biopsies being performed each year in the US. There is little doubt that many invasive, open surgical diagnostic biopsies should be replaced by improved core biopsy procedures.

Reference will now be made in detail to the construction and operation of embodiments illustrated in the accompanying drawings. FIG. 1 shows a biopsy or, more generally, an excisional device 10 according to embodiments. The excisional biopsy device 10 may comprise a tubular coring and transport assembly 11 that may, according to one embodiment, have a distal end defining a scoopula shape. The distal end may have a shape that differs from the scoopula shape and that differs from that shown in the figures. The scoopula forms part of an outer sheath (also called "outer tube," or "non-rotating outer sheath," or "differentially rotating outer sheath," or "manually rotating outer sheath") of appropriate dimensions to retrieve a single or multiple core samples of tissue (not shown) that is/are sufficient to provide the desired clinical diagnostic or therapeutic result. The scoopula may be made of materials, or include coatings, that may enhance penetration and/or hemostasis, and may also be configured to include external features that enhance penetration and/or stabilization within the tissue, for example, spirally-disposed ridges and/or grooves, as well as features such as axial slits to enhance visibility under guidance modalities such as ultrasound. Such an appropriate dimension may be, for example, about 4 inches in length, in addition to a forward excursion of the tubular coring and transport assembly 11 during the coring phase. It is to be understood, however, that the foregoing dimensions and any dimensions referred to herein are exemplary in nature only. Those of skill in this art will recognize that other dimensions and/or configurations may be implemented, depending upon the application, and that the tubular coring and transport assembly 11 and its subparts, as well as other elements of the device, could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting. The outer sheath may be removable such that, according to one embodiment, such outer sheath may be fully detached from the biopsy device 10 and thus be temporarily placed or left in place in the body to enable delivery through its lumen of substances or other devices during pre-operative, biopsy, and/or post-operative phases.

One embodiment of the biopsy device 10, as shown in the figures, may be configured for hand-held operation and may comprise an economically comfortable and secure handle 12 at its proximal end from which the tubular coring and transport assembly 11 extends so that the biopsy device 10 may be easily directed with one hand while the other hand is free to hold a guiding probe such as an ultrasound transducer. However, it is to be understood that embodiments may readily be configured to fit onto any number of guiding devices such as a stereotactic table imaging stage or equipment associated with other guidance modalities such as Magnetic Resonance Imaging (MRI) (not shown). As shown, one embodiment of the biopsy device 10 may comprise one or more sharp, rotating or non-rotating cutting elements 13 (herein, alternatively and collectively referred to as "cutting element," "work element," "beak," "beak assembly," "articulable beak," or "beak element" or "beak elements") projecting forward from the distal free end of the removable tubular coring and transport assembly 11. According to one embodiment, the (one or more) cutting element 13 may travel distally up to the end of a distal scoopula for the purposes of forward penetration, coring and/or parting off of the core sample in a combined forward cutting and side cutting motion in reference to the scoopula. Such a scoopula itself may be composed of one or more elements, such as a series of small forward projections, which in the aggregate have the form of a scoopula. There may also be more than one scoopula extending from the tubular corning and transport assembly, and these may be of different shapes to each other. The tubular coring and transport assembly 11 may comprise a plurality of components, which plurality may be configured to transmit rotational movement and opening/closing actions to the rotating or non-rotating cutting beak elements 13. It is to be understood that the "tubular" description of the coring and transport assembly 11 expressly encompasses any cross sectional shape and size, of any length and may in addition be flexible, as for example, to navigate through vascular spaces or around sensitive structures within soft tissues. It is further to be understood that the term non-rotating also includes other cutting actions such as axially aligned, for and aft movements of cutter elements, which may be powered or manually actuated. Such actions may consist of slow "jack-hammering" movements alone or in combination with rotation, or may include high frequency motions such as ultrasonic vibrations. Cutting may also be carried out alone or in combination with these motions and/or rotation (rotation including continuous in one direction, cyclic reversing or in oscillation) by energizing cutting surfaces with modalities or combinations of modalities such as laser, radiofrequency, microwave, heat and chemical among others. Embodiments include tailoring of excursion of fore and aft and/or rotational movements such that they may be configured to preferentially cut/core specific tissues. For example, shorter frequently repetitious excursions could preferentially sever hard tissue leaving soft tissue intact, while longer excursions that exceed certain soft tissue elastic limits could bias cutting towards more effective soft tissue severing. The components and features of the tubular coring and transport assembly 11 may also be configured to transfer the core sample(s) back proximally along the internal length of an inner lumen defined within the tubular coring and transport assembly 11 to the handle 12 and to the transfer compartment or magazine 27.

According to one embodiment thereof, the biopsy device 10 may comprise a handle 12, which handle 12 may comprise and/or be coupled to mechanical components (not shown in this figure) configured to drive the distal tubular coring and transport assembly 11 to enable it to discharge its coring, transport, part-off and delivery functions. As shown, one embodiment may comprise a distally-disposed beak element 13 that may comprise one or more sharp cutting tip blades configured, together with a distal scoopula portion of an outer sheath, to penetrate tissue to the target site of the intended biopsy, core the target biological tissue and part-off or cut off the core sample (not shown) at the end of the scoopula or beyond, or at any desired point along the length of the scoopula of the outer sheath. The ability of the present biopsy device to repeatedly core and retrieve multiple samples (not shown) during a single insertion and then accumulate the cored samples in a transfer magazine 27 means that with a single penetration through the skin of, for example, a human breast, the operator can sample multiple areas without causing additional trauma that would otherwise be associated by repeatedly removing the biopsy device 10 each time a sample is taken, and reintroducing the biopsy device 10 back into the patient to take additional core samples. The handle 12 may also comprise and/or be couple to (internal or external) mechanical components (not shown) and features for vacuum-assisted fluid evacuation as well as components configured for the delivery of materials such as, for example, a variety of medications, tracer materials, implantable elements, marker elements and diagnostic and therapeutic devices. The tubular coring and transport assembly 11, according to one embodiment, may be configured such as to create the smallest possible caliber (e.g., outside diameter) of coring tube (tubular coring and transport assembly 11) with a range of (for example) about hypotube 16 gauge to about 8 gauge diameter, while providing a sufficiently large diameter of core sample obtained to be clinically useful. The tubular coring and transport assembly 11 may also be constructed of flexible materials and be of a sufficient length to reach target sites distant from the skin surface without the need for an open surgical procedure to enable the distal end (that end thereof that is furthest from the handle 12) of the biopsy device 10 to reach the targeted site. In the embodiment of FIG. 1, the distal tubular coring and transport assembly 11 of the biopsy device 10 may extend distally from the handle 12 and be configured to provide a distance sufficient to create a core of sufficient length for diagnosis and/or treatment purposes. As is described below, this distance of forward or distal projection may be selectively changed at will, thanks to structure configured for that purpose, which may be built into or otherwise coupled to the present biopsy device 10.

Embodiments of the present biopsy device 10 may be used by right and/or left handed persons and in multiple positions and orientations, so that in areas of limited access, the present biopsy device may still be easily positioned for ideal orientation to perform a biopsy procedure under real-time or other image guidance modality. The entire device may be configured to be disposable or may be configured to be reusable in whole or in part. Embodiments of the present biopsy device 10 may be electrically powered by one or more batteries and/or external power sources through a simple electrical coupling to connect to an external power supply conveniently placed, for example, in the handle or proximal end of the present biopsy device as shown at element 637. The entire device may also be internally or externally manually powered, mechanically powered or be powered by means such as compressed air, gas or pressurized fluid. Powering the excisional device entirely mechanically may be advantageous in areas in which the electric grid is absent, unavailable, or unreliable. In FIG. 1, the biopsy device 10 is shown in a pre-coring configuration with the scoopula-shaped distal end thereof open and in a configuration in which it partially projects forward from the proximal handle 12 from its resting position with a portion of the beak element 13 extending slightly distally in closed configuration along the first part of its forward excursion. In this view, the biopsy device 10 is shown with various illustrative switches to activate and/or physically move various internal components (not shown).

One embodiment is a method of carrying out a breast biopsy. Such a method may comprise imaging the tissue of the organ (the breast, in this example) of interest and identifying the target lesion(s) or tissue to be removed or biopsied. The skin may then be cleaned using sterile techniques, the patient may be draped and anesthetics may be delivered. In the case wherein the present biopsy device is configured for stereotactic operation, the present biopsy device may be mounted to the stage of a stereotactic table. The stage is used to fix the position of the biopsy instrument, which may be electronically registered and rendered on a screen. The generated electronic data may be used to position the device within the patient, under computer assistance. The coordinates of the target lesion from the initial images may be recorded in x, y and z axes. Thereafter, once the biopsy device is attached, those dimensions are automatically keyed into the system and x, y and z axes are then calculated to aim the biopsy device (manually entered into the adjusting wheels of the stage) and the stage is cocked for firing or, according to embodiments, the internal firing mechanism of the device 10 is used in place of or in addition to the stereotactic table stage firing mechanism. Once the biopsy device is in place (after firing), a new set of images are taken with X-ray and the new target coordinates (if changed) are entered. If the biopsy device appears well placed, biopsies are generally taken "about the clock face", according to one embodiment. Herein, "about the clock face" generally means in 6-12 spaced positions around the clock face (i.e., 6 to 12 samples over a 360 degree sweep around the initial biopsy penetration axis). If short samples (shorter than the length of the scoopula, for instance) are desired, the operator may manually part off the core sample at any length along the forward movement of the cutting elements and continue to core forward or reset the coring assembly at its most rear-ward position for further full length or short coring procedures. Once all core samples are taken, the device may then be backed out with the stage controls (manually) and a post-procedure set of X-ray images may be taken to determine whether the target was partially or fully removed. Next, a photographic record may be taken of the samples in the transfer magazine and/or a post procedure set of X-ray images may be taken of the removed samples to determine whether markers of the lesion (micro-calcifications in this instance) are present in the retrieved samples. Lastly, a post procedure clip or marker may be placed in the biopsy site area to mark the location of the biopsy to enable a later precise identification of the location of the biopsy and the wound may be dressed and bandaged.

In more detail and according to one embodiment, once the present biopsy device has been fixed to the stereotactic table stage, the distal tip of the biopsy device may be introduced through a nick/incision in the patient's skin. The present biopsy device may then be maneuvered into the desired position, using one of the penetration modes of the device. Once the distal end of the device is in close proximity to and aligned with the target lesion, a further penetration mode of the present biopsy device may be activated, either with the stereotactic table's own firing mechanism or the depth controllable firing mechanism built into the present biopsy device or both, according to embodiments. Such embodiments may specify that only the outer sheath and incorporated scoopula are actually fired through the lesion or the entire tubular coring and transport assembly may be fired forward together with the outer sheath and scoopula. In one embodiment, the scoopula may be fired to a specified distance less than its full travel capabilities. It should be noted that the scoopula and any other elements, for example, a guide, may be fired independently of any other element. In any of these penetration modes, or in otherwise maneuvering the device, the scoopula-shaped distal end of the outer sheath of the biopsy device may be placed in proximity to or through the target lesion. Alternatively, the removable outer sheath may be similarly placed by itself through a nick in the patient's skin to a position in proximity to or through the target lesion, with or without a jig or fixture or holding device to fix it to the stereotactic table stage or manually, as which point an optional delivery stage may then be initiated to deliver, for example, the contents of a preloaded cartridge comprising, for example, tracer elements such as visible dyes, echo-enhancing materials and/or radioactive tracer elements. After or instead of such an optional delivery stage, the device 10 may be connected to the previously placed removable outer sheath in order to deliver biologically-active substances such as medications (such as epinephrine, for example) or anesthetics. It should be noted that such biologically-active substances may also be delivered at any stage of the biopsy procedure, either directly through the open beaks, through the living hinges of the closed beaks or via a reverse flow from the flush system built into the device. After or instead of such an optional injection stage, the distal beak or beaks or work element 13 may then be opened and advanced along the scoopula-shaped distal portion of the outer sheath and may be caused to rotate to facilitate penetration through the tissue and coring. The rotation and advancement of the distal beak or beaks 13 may be caused to stop just at or near the forward edge of the scoopula leaving, according to one embodiment, no or substantially no dead space at the distal-most tip of the present biopsy device that would otherwise be unavailable for sample acquisition. The coring may then continue as normally encountered in stereotactic procedures, i.e., around the clock face but also laterally in any direction with the present device, and in either an automatic or semiautomatic mode. During one or more of the corings, a record stage may be activated to halt the coring stage just after the specimen has been parted-off in order to enable the practitioner to record images(s) of the shaft or scoopula of the biopsy device in place in the lesion, and to record and document that core samples in the transfer magazine 27 (particularly those of different chosen lengths obtained serially during the procedure) were acquired precisely and sequentially from the previously-imaged lesions. Following the acquisition of a sufficient number of core samples and following the herein aforementioned documentation stage, the core sample acquisition site may be firmly correlated with the image abnormality location.

Another embodiment is another method of carrying out a biopsy. Such a method may comprise imaging the tissue of the organ (the breast, in this example) of interest and identifying the target lesion(s) or tissue to be removed or biopsied. The skin may then be cleaned using sterile techniques, the patient may be draped and anesthetics may be delivered. In the case wherein the present biopsy device is configured to enable independent forward firing of the outer sheath or scoopula, the device may be introduced through the skin nick in the "pre-fire" loaded position and moved forward with or without rotation to the nearest edge of an imaged lesion. At that point, the operator would release the scoopula to fire forward under the force of a spring or compressed gas, such as a $CO_2$ cartridge for example, or manually, or by any other mechanical means, including pressurized fluids for example, or by electromechanical means. Once fired, the scoopula would enter the lesion center with little if any residual shift in the lesion position, even if the lesion were to be of a firm nature (as in a benign fibroadenoma or a malignant carcinoma for example) and even if situated within very elastic fatty/fibrous tissue such as exists in the majority of otherwise normal breast organs. Once across the target lesion and approximately centered, the scoopula may be re-imaged for verification purposes and to precisely correlate the biopsy device position with respect to imaged abnormality. Additionally, the device may then be easily manipulated for fine-tuning purposes if desired. Also, were the scoopula to be fired to a position close to a nearby vulnerable structure (whether tissue or radiology backing plate or other), the operator may then be able to advance carefully the last few millimeters to the most optimal location. After these maneuvers and verifications have been completed, the target is now fixed by virtue of the pinning stabilization effect of the scoopula component. This enables the operator to then proceed with a number of options. First, the operator may elect to deliver substances in a more pinpoint location using the scoopula as a reference as well as a delivery pathway. For example, a radiation source could be introduced through the central lumen, antibiotics and/or local anesthetic medications as well as coagulants and/or vasoconstrictors may be introduced. Likewise tracer elements to trace the pathway to sentinel node drainage may be introduced at this stage of the procedure such that sufficient time passes while the rest of the biopsy procedure is completed to enable detection in the sentinel node toward the end of or after the biopsy portion of the procedure has been completed. Another option is to simply proceed with multi-sample biopsy while taking cores "about the clock face" as previously described. Following sampling to completion, other options may follow such as halting the coring beaks in open and proximal position while leaving the scoopula distally placed, such that post-procedure elements may then be introduced via the distally placed (across the lesion that had been completely sampled or removed) scoopula, precisely in the place of the biopsy sampling. These elements could include implants such as cosmetic filler/delivery substances as well as other post-procedure devices that may be introduced via the central lumen/scoopula pathway, such as an electron beam reflector, a fiber-optic scope, an ultrasound transducer, a cryotherapy element such as an "ice-ball-on-a-stick" probe (as described in more detail in the following paragraph), a laser or radiofrequency tissue ablating device or even an optical signal acquisition and processing device to capture micrometer-resolution, three-dimensional images. Upon completion of any of these options, the scoopula may be detached and left in place for other purposes or may optionally be removed together with the parent device and then the procedure terminated in the usual way with control of any bleeding, closure of the skin nick and the usual post-procedure dressing(s).

An embodiment of a biopsy device additionally includes an independently movable or fixed guiding element such as a stiff or floppy wire that my lead the way through a natural surface or potential space. Such a guiding element could be pre-placed and then elements of a biopsy device advanced over the guiding element. Alternatively, a guiding element may be fired forward in the same manner as the scoopula described above, or it may simply be fixed near or at a forward (distal) position of elements of the biopsy device. Further still, a guiding element could be coaxial with, in tandem with or adjacent to the long axis of elements of the biopsy device. The guiding element could additionally, be a completely separate entity that may be pre-placed by an operator skilled in imaging and targeting and fixed in place near or within the target tissue. After placement and fixation an operator may then proceed by advancing the biopsy instrument over the previously precisely placed and anchored guiding element.

Embodiments of the biopsy device, along with related subcomponents and features, may also be configured for imaging of the surrounding tissue during pre-operative, intra-operative, and/or post-operative phases of the device clinical use. One embodiment for imaging integration may be implemented by insertion of a transducer or associated optical components for ultrasound imaging, direct visual imaging, or Optical Coherence Tomography (OCT), through the lumen of the biopsy device which may be carried out at any one or multiples of the aforementioned phases. The transducer may be comprised of a single element, a phased array, or a stacked array and may be fixed or move in rotation or translation relative to the scoopula and may move with a beak(s). Embodiments of the biopsy device might incorporate imaging transducers in parts of distal biopsy device subassemblies such as the distal portion of the outer sheath or scoopula or as a part of the beak. Embodiments of the biopsy device could also use a lumen for free-space coupling of laser or broad spectrum light into and/or out of the tissue and may use the living hinge or a reflective component attached thereto to direct or steer the electromagnetic radiation. The internal surfaces of the tubes or scoopula may also act as reflectors or directors for the light beam. Embodiments of the biopsy device may also be configured to allow for ablation of tissue during pre-operative, intra-operative, and/or post-operative phases. Ablation may be accomplished through one or more combinations of hyperthermic ablation (such as radiofrequency, microwave, laser, and ultrasound) and/or cryoablation techniques. The ablation sub-assembly may attain access through the central lumen of the biopsy device, may be an integral part of the biopsy device, or may connect to or be inserted through a portion of the biopsy device that is left in the body providing appropriate access to the tissue site. One embodiment may use radio frequency ablation techniques where parts of the scoopula or beaks are energized. The relative rotation and/or placement of the distal components of the biopsy device may serve to selectively direct and/or focus the energy. The sub-assemblies to accomplish this may be an integral part of the biopsy device or may be inserted through the lumen of the biopsy device. These sub-assemblies may be configured to interact with elements of the distal scoopula to raise them into position needed for their function and these interactions may also enable them to perform a part of the biopsy procedure itself, such as forming a surface against which part-off may be accomplished. They may also accomplish coring and/or part off by themselves (through flexing, rotation or other actions as described for beak elements, or by being energized) or in combination with surfaces of the scoopula or with other elements introduced along the scoopula including physical elements and/or beams or other forms of energy such as electromagnetic sources, heat sources and others, according to embodiments. Another embodiment may use microwave radiation ablation and may incorporate antennae elements into the beak, outer tube or scoopula or may incorporate antennae elements in a sub-assembly that could be inserted through the central lumen or in close proximity to the axial length of the tubular coring and transport assembly 11 (just underneath or alongside, for example) of the biopsy device when desired. The location of the antennae may be varied along the axial length of the open scoopula and may also be rotated relative to the scoopula resulting in selectively directing the microwave energy. Furthermore, electromagnetic reflectors could be built into the scoopula or other members and stacked or phased arrays of antennae may be employed to further direct or dynamically tune the radiation pattern. Another embodiment may also use electron-beam ablation and may incorporate a beam guide tube that may be inserted through a lumen in the biopsy device to deliver the electron beam to selective locations in the tissue surrounding the device. Another embodiment may use laser ablation and may deliver and direct the laser beam through an optical fiber or through a free-space coupled beam. The beam or fiber may be directed by a reflective surface on or attached to the internal angle of the living hinge and/or a reflective surface of the scoopula. This may allow the beam to be directed in a pattern optimal for the desired ablation. The laser ablation sub-assembly may use the central lumen to deliver the light to the distal portion of the biopsy device or may attach to an integral optical delivery system. Another embodiment of the biopsy device may include a probe that provides cryosurgical ablation of tissue surrounding a cold probe that may be inserted through or be integral to the biopsy device. The cold probe may repeatedly warm and rapidly cool the surrounding tissue resulting in ablation. The probe may be positioned relative to the scoopula such that the rotatable scoopula provides a heat sink selectively shielding tissue from ablation.

Upon completion of the biopsy procedure and, if desired, prior to removal of the device, a specimen ultrasound or a radiograph may be carried out upon the specimens collected within the transfer magazine 27, which magazine may be specifically configured for echo- and radio-lucency as well as compatibility with MRI and/or other imaging technologies. The removable transfer magazine 27 may then be placed into a receptacle that may be preloaded with preservative and sealed. If desired, a replacement transfer magazine 27 may then be loaded into the biopsy device to continue the biopsy procedure. Alternatively, with the biopsy device 10 in place, an adapter configured for the delivery of materials to the biopsy site may be substituted for the transfer magazine 27 at any time. Alternatively, with the biopsy device 10 in place, the tissue transfer magazine 27 may be removed and replaced with an injection cartridge that may be pre-loaded with post-biopsy elements such as medications, cosmetic implants, brachytherapy elements such as a radio-active seeds, and/or a porous element loaded with a biologically active substance and/or other materials. Alternatively still, the biopsy device 10 may be withdrawn from the removable outer sheath, which outer sheath may then be used for delivery of post-procedure materials to the target site while other components of the biopsy device may be packaged appropriately and delivered to an appropriate laboratory for pathology/cytology analysis. The outer sheath of the biopsy device may then be completely removed from the site and the would dressed using the customary standard of care procedures. If so attached to biopsy device 10 via an aspiration/material delivery port 639, a liquid aspirate storage vessel may be removed from biopsy device 10 at any time and capped securely for transport to an appropriate laboratory for cellular and subcellular analysis. An illustrative placement of an aspiration/material delivery port 639 on biopsy device 10 is shown in FIG. 1 herein.

FIG. 1 also shows illustrative placement of various external controls, including a depth stop adjustment mechanism 630, a forward firing trigger and lever 631, a drive train carrier bolt 632, a manual part-off lever 633, and a cam clutch button 634, as well as other features such as a power switch/indicator 635, a DC power plug 637, a flush port 638 and an aspiration/material delivery port 639, which will be discussed in more detail in further figures. The placement of these external controls is illustrative in nature and embodiments may contain some or all of these controls in the locations shown in FIG. 1 or other locations.

It is to be understood that the above descriptions are but exemplary methodologies and that one or more of the steps described above may be omitted, while other steps may be added thereto to any of these embodiments, depending on the target site within the body, which is not limited to the breast. Other operator method embodiments and device 10 embodiments are supported as well. The order of some of the steps may additionally be changed, according to the desired procedure.

Figure 2:
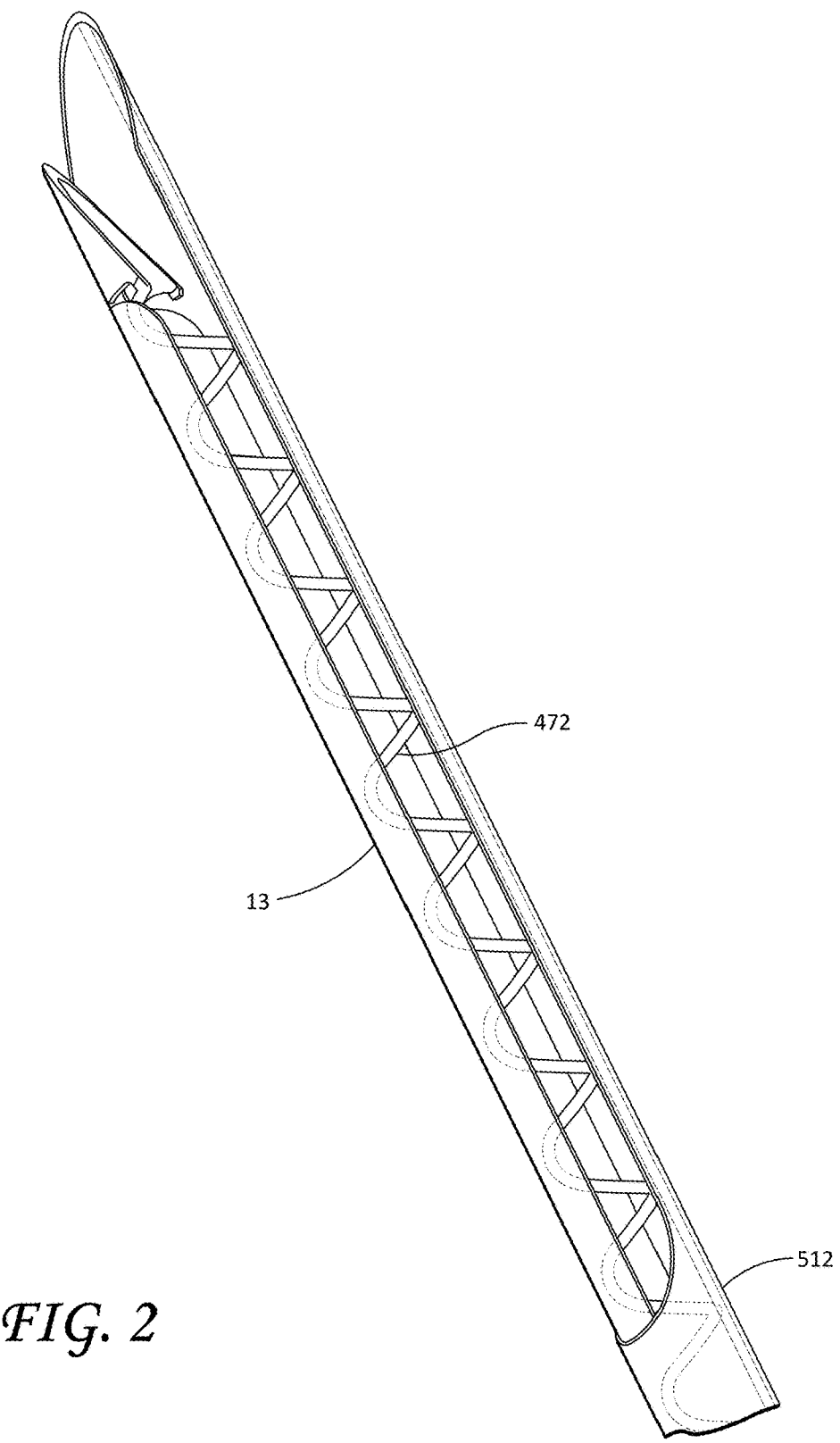
FIG. 2 is a perspective view of a movable, rotatable scoopula-shaped outer sheath with a movable, rotatable cutting element and transport helix attached, according to one embodiment.

FIG. 2 shows a distal end of a coring and transport assembly 11 of FIG. 1, with a configuration of a manually rotatable outer sheath 512, having a distal tip in the form of an edge-sharpened trough or scoopula. As shown, the coring and transport assembly 11 may comprise a rotating and longitudinally movable (e.g., selectably movable in the distal and proximal directions) articulable beak (or work element) 13, which may, in one embodiment, be actuated by an internal helix 472. Although a single beak is shown and described in this figure and some of the following figures, it is to be understood that more than one beak may be used in embodiments, and for that reason, whether only one beak, double beaks or multiple beaks are described herein, all such embodiments are considered to be within the scope of this disclosure. If more than one beak is present, their individual shapes may be asymmetric to each other or have differing features. As described above, upon entry of the coring and transport assembly 11 to the target site within the body a procedural option may be chosen where only the scoopula-shaped distal portion of the outer sheath may be exposed, and the work element may be held in place at the proximal opening of the scoopula. As the device is advanced, the sharpened trough-like scoopula may be made to cut its way forward in the distal direction, with little disturbance to the target lesion. Indeed, as the scoopula-shaped distal portion of the outer sheath presents a minimized cross section (as compared, for example, to the cross-sectional profile presented by a tube), dissection of the tissue path to the lesion occurs with reduced distally-directed force and little disturbance to the surrounding tissue and to the target lesion. This is a significant feature of the device 10, according to embodiments, because with a minimized cross-section, such a scoopula may be made to cross the lesion (or tissue immediately adjacent thereto) with minimal disturbance to or displacement of the lesion and may also be moved laterally for precise positioning, as previously discussed herein. As coring has not yet occurred, the scoopula-shaped distal portion of the outer sheath enables the device 10 to be advanced to or past the target lesion with a reduced chance of transporting potentially malignant cells or material through the lesion to otherwise healthy tissue. A further advantage of optionally advancing only the trough shaped scoopula is that it minimizes both physical and visual distortion of the image, enabling a guidance modality to identify structures nearly as easily as before anything was introduced across the lesion, enabling positive correlation between the imaged tissue and later pathology findings. It is to be understood that, according to embodiments, the phrase "scoopula-shaped distal portion of the outer sheath" is intended to encompass a distal portion of the outer sheath that is shaped so as to present an open portion or a less-than full cross-section, as compared to more proximally-disposed portion(s) of the outer sheath 512.

The sides or edges of the distal scoopula may be sharpened, may be parallel to the long axis, or may be of varying profile with respect to the long axis. For example, the sidewalls of the scoopula may be gradually rising from its distal to proximal portions, enabling pre-severing of the tissue prior to engagement of the beak or beaks work element. Some or all of the edges of the scoopula, including the "roof" or proximal arch of the scoopula may be sharpened, serrated or otherwise configured in order to optimize coring and/or stabilizing actions as well as to permit a variety of pathways for aiding core sample transport, such as fluid flush and vacuum. In one embodiment, a beak or beaks work element by itself may sever tissue without the need to contact any surface of the scoopula, simply by nature of the shearing action and by virtue of exceeding the elastic limit of the tissue as tissue is forced over the edges of the scoopula. With a distal scoopula acting as a stabilizer and being anchored through the lesion, the work element (single beak, multiple beaks etc.) may then be made to move axially in a distal direction and, according to one embodiment, under rotation. This effectively combines a forward cutting mechanism, with reference to a single rotating beak (or multiple beaks) acting against the sides or edges of the scoopula, as such a beak or beaks moves forward with a scissors-like action against the side of the scoopula, and a side cutting mechanism from the point of perspective of the scoopula, as the sharpened sides of the beak or beaks bear against the sides or edges of the scoopula, according to embodiments. In one embodiment, a beak or beaks work element by itself may sever tissue without the need to contact any surface of the scoopula, simply by nature of the shearing action and by virtue of exceeding the elastic limit of the tissue as tissue is forced over the edges of the scoopula. FIG. 2 shows the coring beak disposed distally almost all the way forward to its part-off point and rotated slightly as it would be seen as a snapshot of its continuous forward travel while rotating, coring, and then eventually parting off as it reaches the end of the scoopula. The coring beak may then be configured to part-off the cored sample by closing down against the inside diameter of the scoopula. Upon finishing its coring cycle, the work element may be configured to withdraw under rotation or not back to its initial position (according to one embodiment, adjacent to the proximal opening of the scoopula), thereby transferring the parted-off sample proximally to an internal transport mechanism and continuing to a transfer magazine 27 (not shown). In the embodiment illustrated in FIG. 2, such internal transport may be carried out by a rotating helix or helices 472 disposed in the central lumen of the device. It should be noted that the centrally-disposed helix 472 shown in FIG. 2 is but one possible mechanism to rotate the beak element(s) 13 and to transport parted-off cored samples in the proximal direction, and embodiments are not to be limited thereby.

Significantly, if the operator allows full forward travel of the work element(s) 13, there will be no or substantially no distal tip dead space, i.e., the device will sample (e.g., core) all the way to or substantially to the distal-most tip of the scoopula within or past the lesion, as originally placed. This lack of dead space allows optimal placement of the excisional device 10 in relation to physical structures such as the chest wall, radiology backing imaging plates or other structures associated with either the body or the supporting device, such as a stereotactic table. If the device is used with a stereotactic table, either the device itself, in one embodiment, or the outer sheath, in one embodiment, may then be rotated "around the clock" such that the open portion of the scoopula faces the next desired clock face position and coring may begin again, repeating as often as desired, selectively fully or partially. It should also be noted that, because the distal end and edges of the scoopula may be very sharp, according to one embodiment, lateral displacement of the distal end of the device 10 may be accomplished, either with or without rotation of the outer sheath, thus giving the operator greater flexibility to pursue the edges of a lesion that may not be spherical in shape. As noted above, medications and other materials may be delivered to the target site. A vacuum source connected to an aspiration/material delivery port that may be configured for aspiration may be used to collect the tissue samples, cells and fluids either originating from the site or injected to the site, for instance, as well as to aid in transporting the severed tissue specimens proximally to, in one embodiment, transfer magazine 27. Such vacuum source may be connected to a port located on, in one embodiment, the handle, for example 639, or in another embodiment, located on the scoopula.

Figure 3:
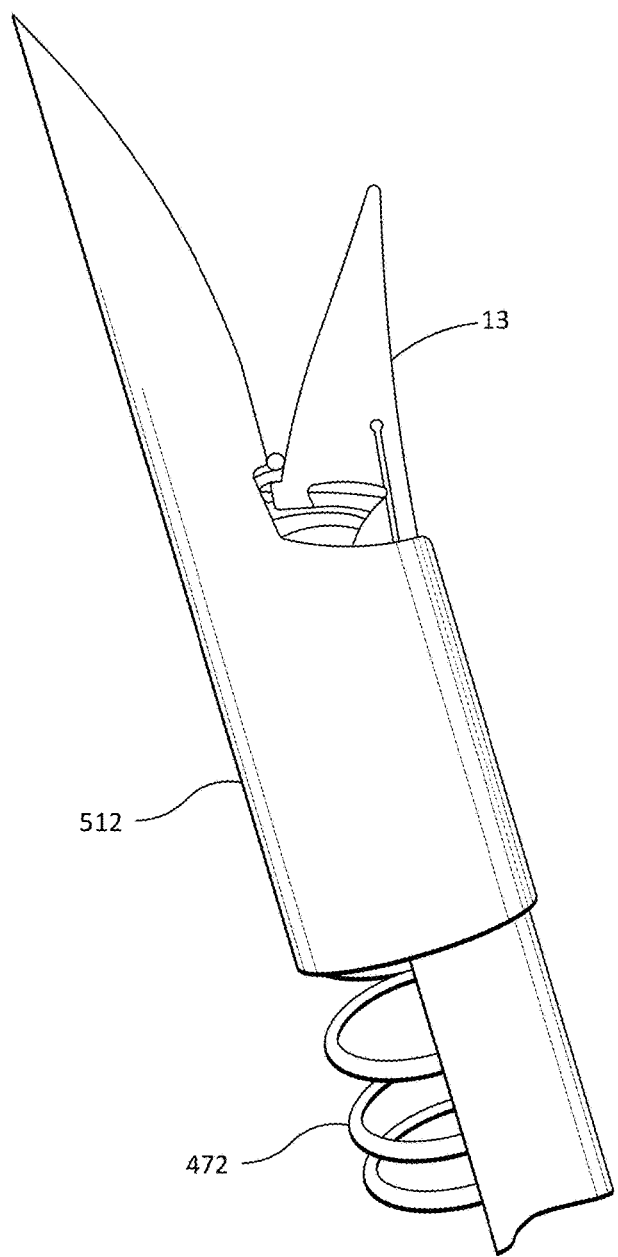
FIG. 3 is a side view of an outer sheath and articulated beak and helical element, according to one embodiment.

FIG. 3 illustrates distal details of the work element and scoopula of FIG. 2, showing an embodiment having a relatively shortened scoopula portion of the outer sheath 512. In FIG. 3, the outer sheath 512 is cut away to show the internal helix 472 (also shown as element 582 in later figures), according to one embodiment. The embodiment of FIG. 3 may find particular utility in tissue coring applications outside the breast, such as bone. The shortened scoopula portion of the outer sheath 512 may also be useful next to sensitive structures in general and in cardiovascular applications in particular. It should be noted that the scoopula and its corresponding work element may be of any length necessary to match a particular tissue, target lesion, and/or site, according to embodiments. In this figure, the beak of the work element 13 is shown opened over center, and as it rotates it is thus forced to close down slightly against the edges of the scoopula and parallel with the long axis of the helix, which supplies either some or all of the rotating force, according to one embodiment. In this view, it can easily be envisioned that much or all of the rotating force may also be supplied to the beak by an extended collar to which the beak may be attached, in one embodiment, by a living hinge 458, as will be described later in more detail in other figures. According to one embodiment, an internal helix 472 may be configured to provide the axial force that is necessary to open and close the beak(s) against the scoopula for tissue part-off and retrieval and transport.

According to one embodiment, a helical element 472 and a first articulable beak element 13 (or first and second articulable beaks in a double beak configuration, according to embodiments described herein below) may be configured to rotate at a rotation rate of between, for example, 0 to about 10,000 rpm. For example, a rotation rate of between about 3,000 and 7,000 rpm may be selected for parts of a procedure. According to one embodiment, a dither or slight jittering of the articulable beak elements may be implemented in place of or imposed on top of the rotation. One implementation calls for a rotation rate of about 5,000 rpm (plus or minus about 20%) during at least one phase of the tissue coring and excision process. According to one embodiment, a helical element 472 may define a single-coil configuration. According to embodiments, the helical element or elements may be provided with structure configured to increase its column strength and torque and to decrease the torsional deformation thereof. For example, such a first helical element 472 may comprise a two or three (or more) coil structures. Collectively, these coils may decrease the tendency of a helical element 472 to compress, may increase the torque that it may apply against the tissue through the first or first and second articulable beaks and may increase its resistance to deformation as it is rotated. Such a configuration may also spread the torque load to multiple points of attachment with the first and/or first and second or multiple articulable beaks.

Figure 4:
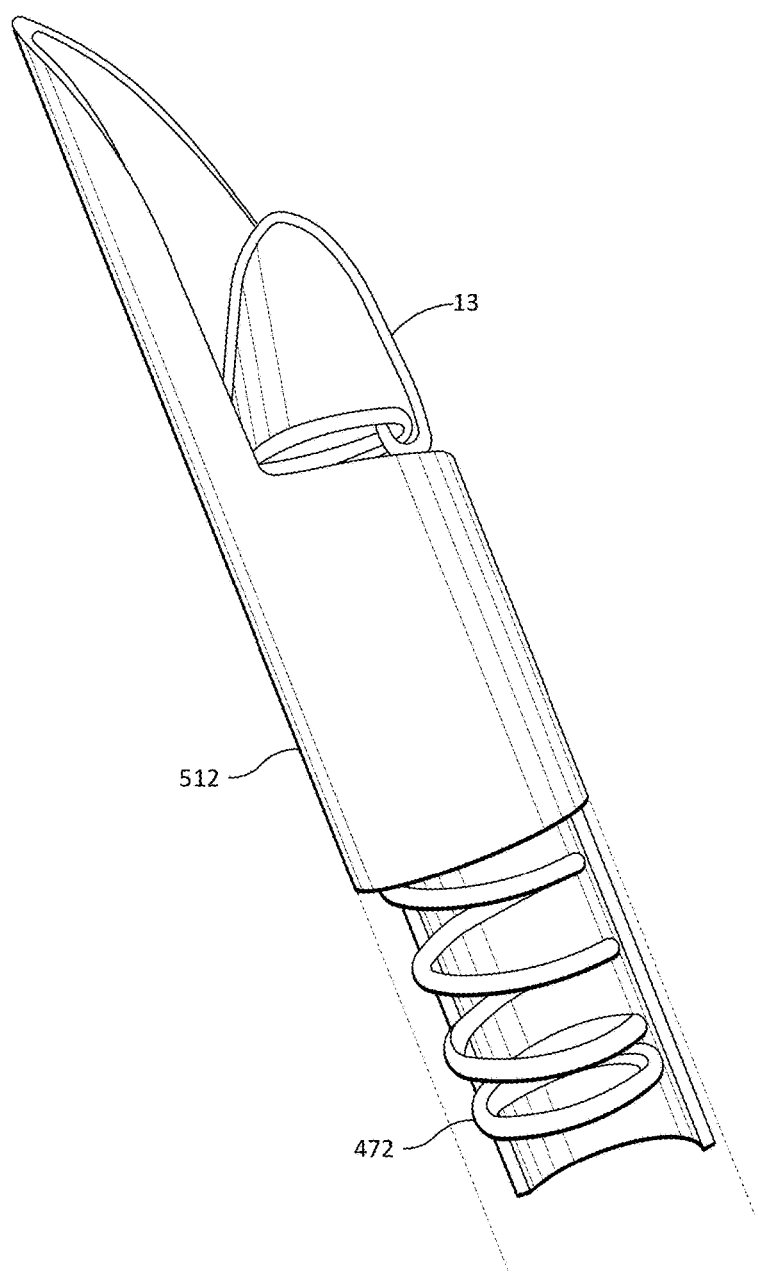
FIG. 4 is a side view of an outer sheath and a rotating inner beak and helical element, according to one embodiment.

FIG. 4 illustrates the same components of FIG. 3, but in a different snapshot of time, corresponding to a later period where the beak element 13 is shown rotating to core the tissue and nearing its final part-off point by action of a single beak closing, in this embodiment, against the end of the scoopula, which in this embodiment acts as a second, non- or differentially rotating beak in relation to the single beak 13 shown in this view. Differential rotation as used herein implies and encompasses different rotation speeds in both the same and opposite directions between individual elements.

Figure 5:
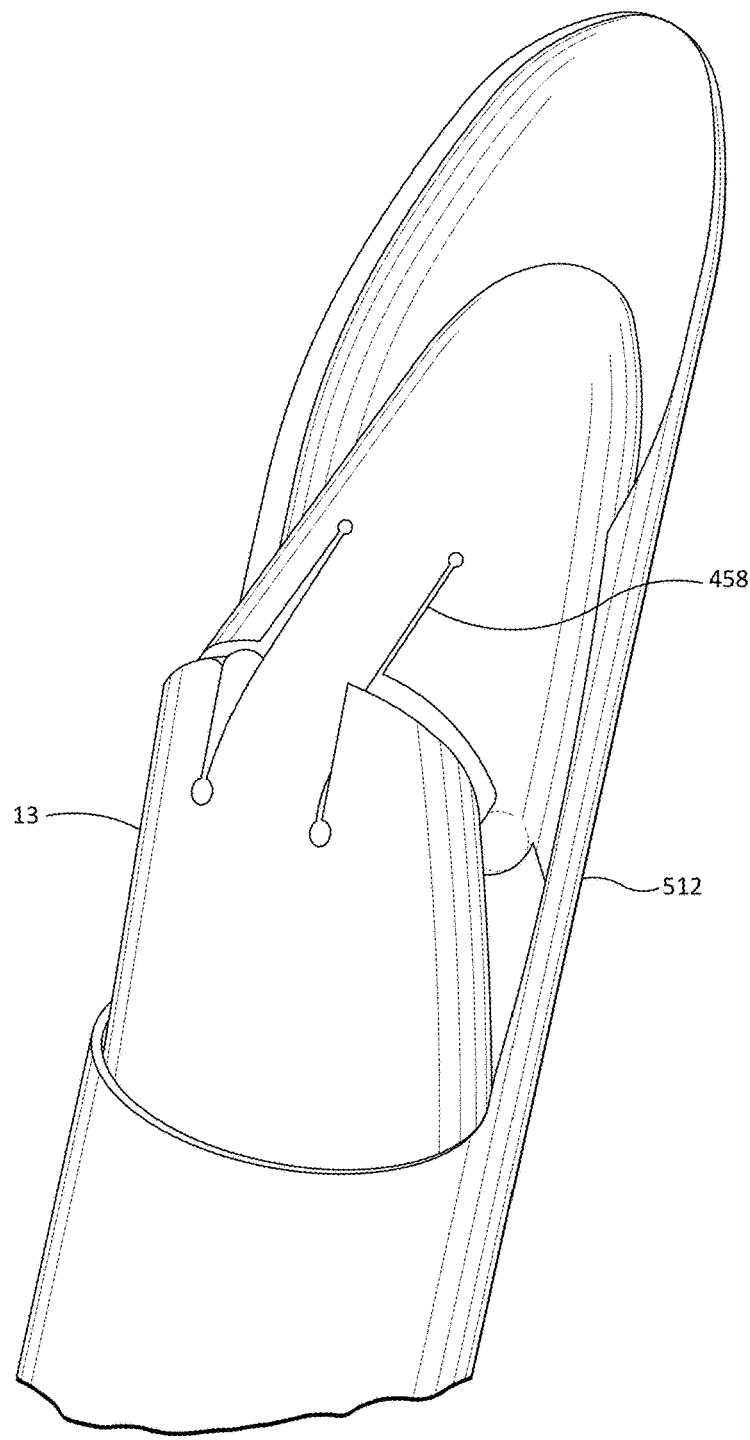
FIG. 5 is an overhead view of a beak element with living hinge closing against a scoopula-shaped outer sheath, according to one embodiment.

FIG. 5 illustrates the same components of FIGS. 2-4, but in this case, the operator has chosen to manually part-off the sample before the beak element 13 has reached the distal end of the scoopula portion of an outer sheath 512, an operation made possible by the drive mechanism of one embodiment of this device, as is described below in later figures. The beak element 13 in such an embodiment may also comprise a living hinge 458. According to one embodiment, a living hinge 458 may comprise an H-shaped series of stress-relieving kerfs and relieving features at the ends of the kerf cuts, allowing the beak element to close against any portion of the scoopula. These stress-relieving kerfs may reduce the stress induced in the living hinge 458 to a non-inclusive range, for example of 10 to 360 ksi (kips per square inch). These elements of a living hinge 458 may also, according to embodiments, serve as conduits for medications (anesthetics and epinephrine, for example) and other liquids, such as saline flushes. Such conduits enable such fluids to flow through the central lumen of the device 10 for delivery to the distal end thereof, even if the beak(s) may be closed during such an intra-operative procedure.

Figure 6:
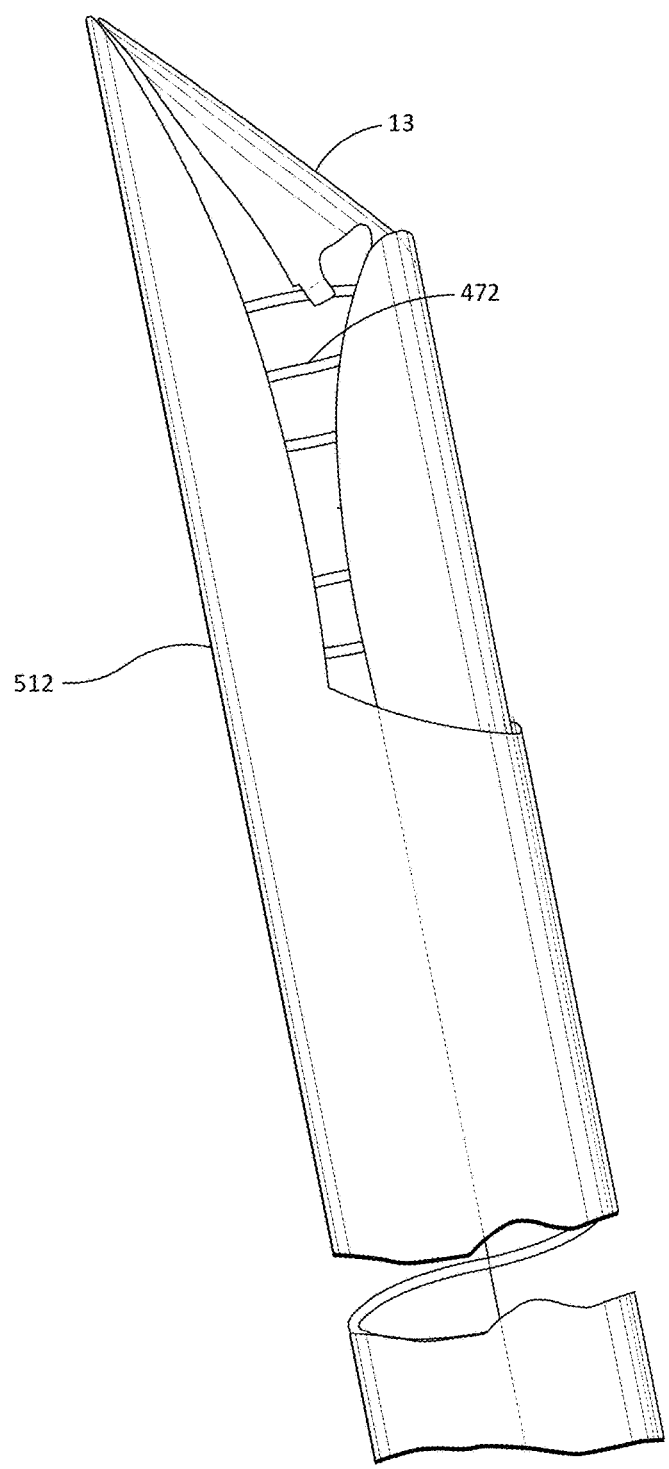
FIG. 6 is a side view of an outer sheath and inner cutting element and helical element, according to one embodiment.

FIG. 6 is a side view of the components of FIGS. 2-5. In this illustration, a more typical part-off point is shown with the forward edges of a trough-shaped scoopula beak and the active beak perfectly or near-perfectly opposed, eliminating all or substantially all dead space at the distal end of the device. One beak attachment tab is shown interacting with the distal end of a helical element 472.

Figure 7:
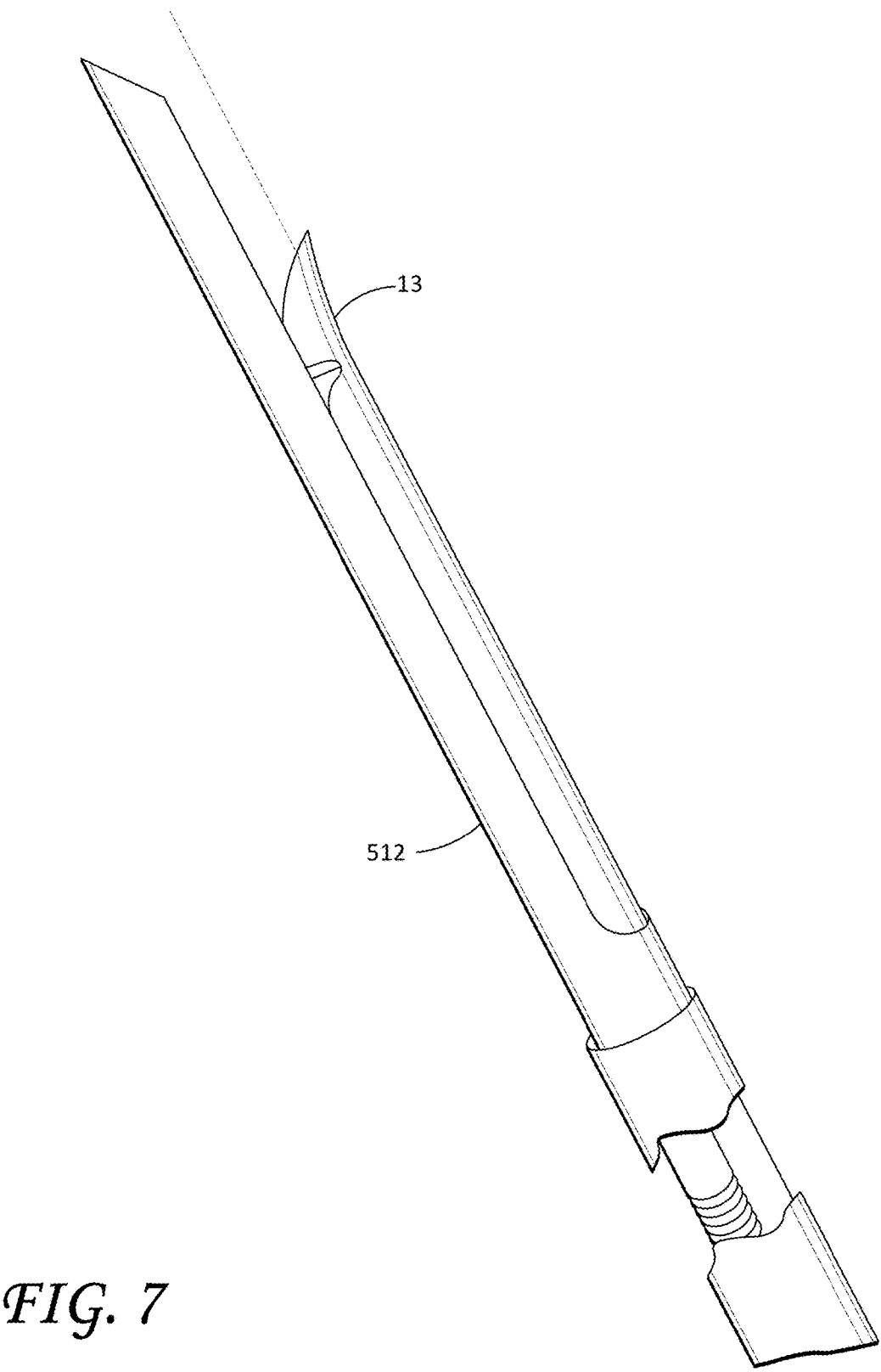
FIG. 7 is a side view of an outer sheath and cutting element, according to one embodiment.

FIG. 7 shows a view of a variant of the distal end of the device, according to one embodiment, that comprises an extended collar on a single beak assembly 13 revealed where the outer tubular element 512 is cut away to reveal the attachment point of the extended collar with a helical inner tubular element 472, as shown in FIG. 6. This variant provides greater stability in the trough-shaped scoopula sections of travel of the inner coring, cutting, transport and part-off active portion of the device and enables high-speed spinning of the active beak element during corning, while protecting the tissue sample from being exposed to high speed helical motion until it has the opportunity to move along the helical portion axially after being fully parted off from the host tissue. Details of active beak attachment are not shown in this illustration.

Figure 8:
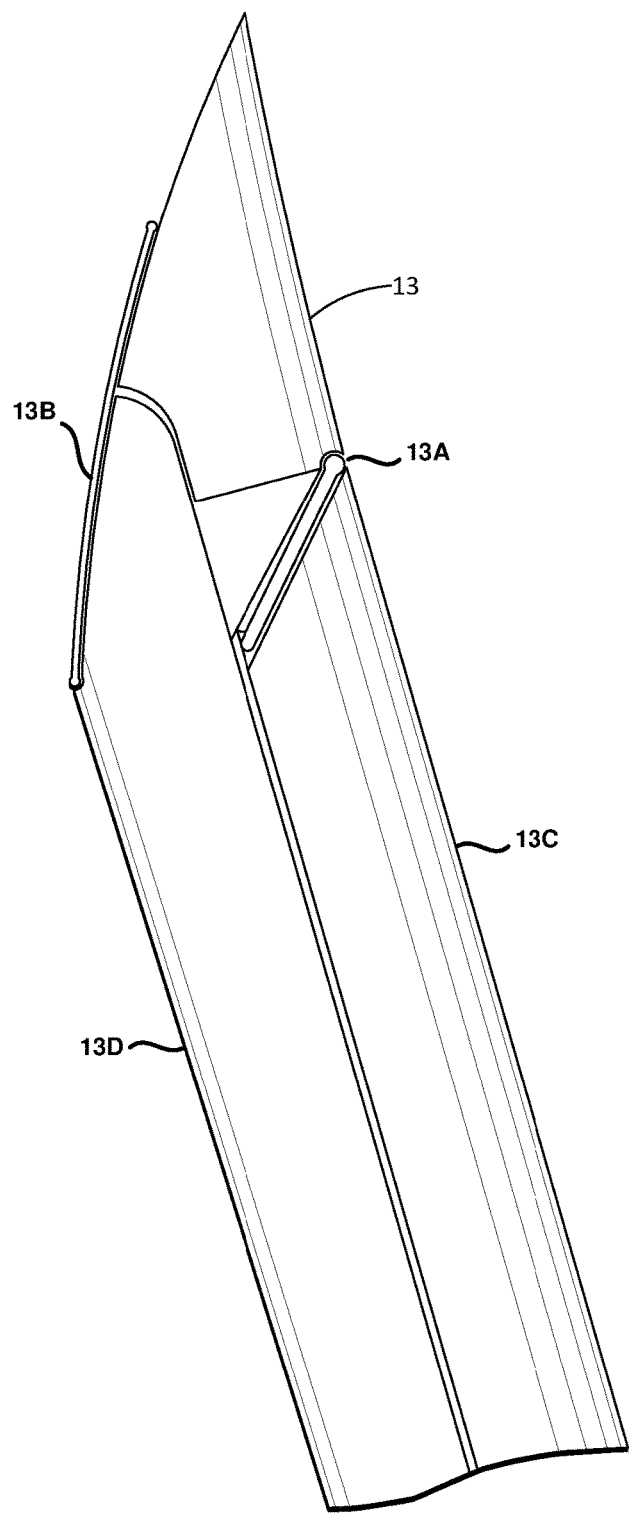
FIG. 8 is a side view of another embodiment of an articulated beak and attachment mechanism, according to one embodiment.

FIG. 8 shows details of a single distal active beak 13 attachment to elements of a split collar using torsion bar 13A and bands 13B to accommodate the transfer of forces needed to open, close, and stabilize the active beak element 13, according to one embodiment. By relative axial movement of the lower half 13D to the upper half 13C of the split collar extension of the beak 13, the bands 13B move proximally causing the beak 13 to close, as shown later in FIG. 11. In such an embodiment, such attachments may simplify the attachment and bending requirements of the active beak(s) such that they may not interfere with sample acquisition and transfer to transport components of the coring and transport assembly 11 of the device, according to this embodiment. Such split collar extension may be configured to have a straight longitudinal split, in one embodiment, or a curved split with respect to the long axis of the device, in other embodiments. Such a curved split with respect to the long axis of the device will impart twisting of the beak or beaks as they close down, which may aid in part off, particularly if the twist is in the opposite direction of the beak assembly rotation. Not shown in this view is the outer sheath 512.

Figure 9:
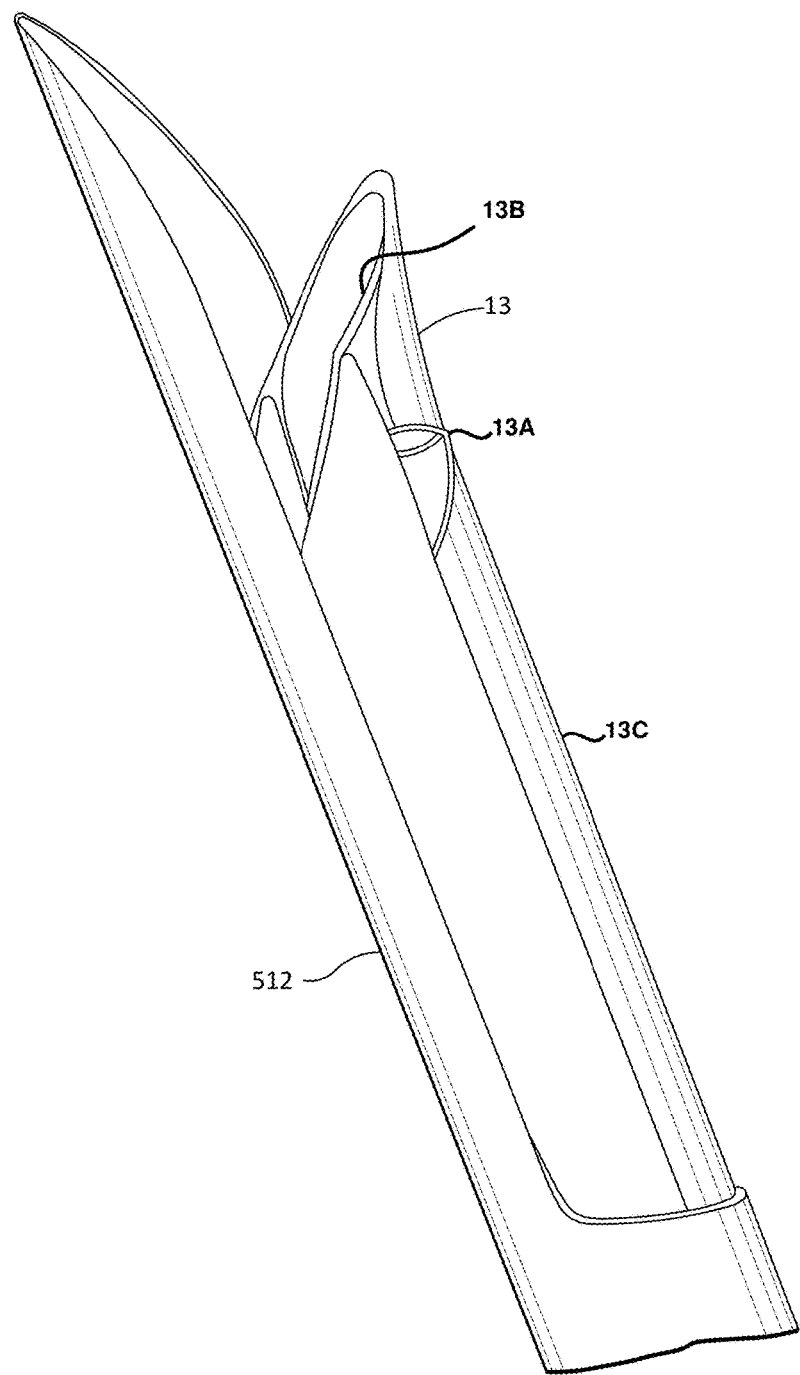
FIG. 9 is a side view of the working elements of FIG. 8, in open beak configuration, according to one embodiment.

FIG. 9 shows the same configuration as in FIG. 8 above, but in a snapshot position showing a scissors-like spring-jaws action of a beak against the scoopula portion of the outer sheath 512, which is shown in this view. Such spring-jaws action is enabled by opening the single beak, in this illustration, more than it would be if the back of the beak 13 remained parallel with the extended collar to which it is attached, or effectively over center. In this view, the torsion bar 13A attached to the proximal end of the beak and the distal end of the upper half 13C of the split collar to which the beak is attached is shown being flexed in a twisting motion to provide a force against which the beak opens. Such a configuration of being open over center causes the beak edges to come in very close proximity with the edges of the scoopula of the outer sheath 512 with every revolution. In this case, the spring action is provided proximally by a helical element and transmitted forward via the lower collar half 13D of the split collar, which is attached to the bands 13B (similar in action to beak opening and closing tendon elements 468 disclosed in further figures below). The active beak element 13 (active in that it moves from an over center open position to a parallel open position) is forced to conform to the trough dimensions of the scoopula each time it comes around in its rotation. Resisting this conformation is the axial force of a helical element acting through a lower collar half 13D and a torsion bar 13A. This results in a powerful shearing action of the active beak against the edges of the scoopula (in this illustration—an inactive or fixed structure). It may also enable a slightly larger sample to be acquired and forced into the collar section. Additionally, the conformation of an active beak relative to a trough section with each rotational cycle of the active beak creates a slight repeated back and forth motion of a lower collar half 13D as compared with an upper collar half 13C and thus an axial oscillation action between lower and upper halves of an extended collar section, which may tend to move the severed tissue specimen axially in a proximal direction. If inner elements such as scales etched or ground into the inner diameter of a split collar are added to such an embodiment to take advantage of the axial tissue specimen movement gained by this repeated back and forth action, a ratcheting mechanism to aid delivery of tissue to a transport section of the device may be created. Other inner wall treatments such as rifling, among such treatments, may also be added to aid in the transport of the cored and parted-off tissue samples in the proximal direction.

Figure 10:
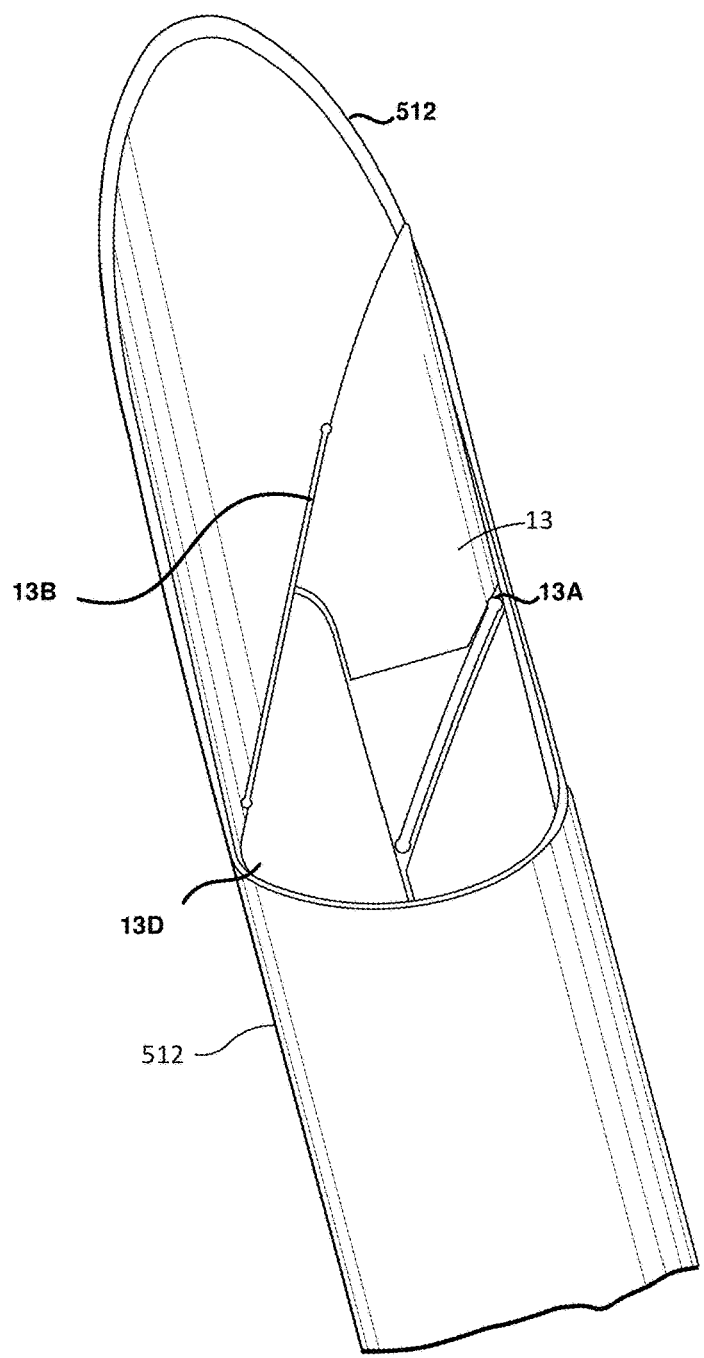
FIG. 10 is a side view of the rotating inner cutting element and outer rotatable scoopula-shaped element; according to one embodiment.
Figure 11:
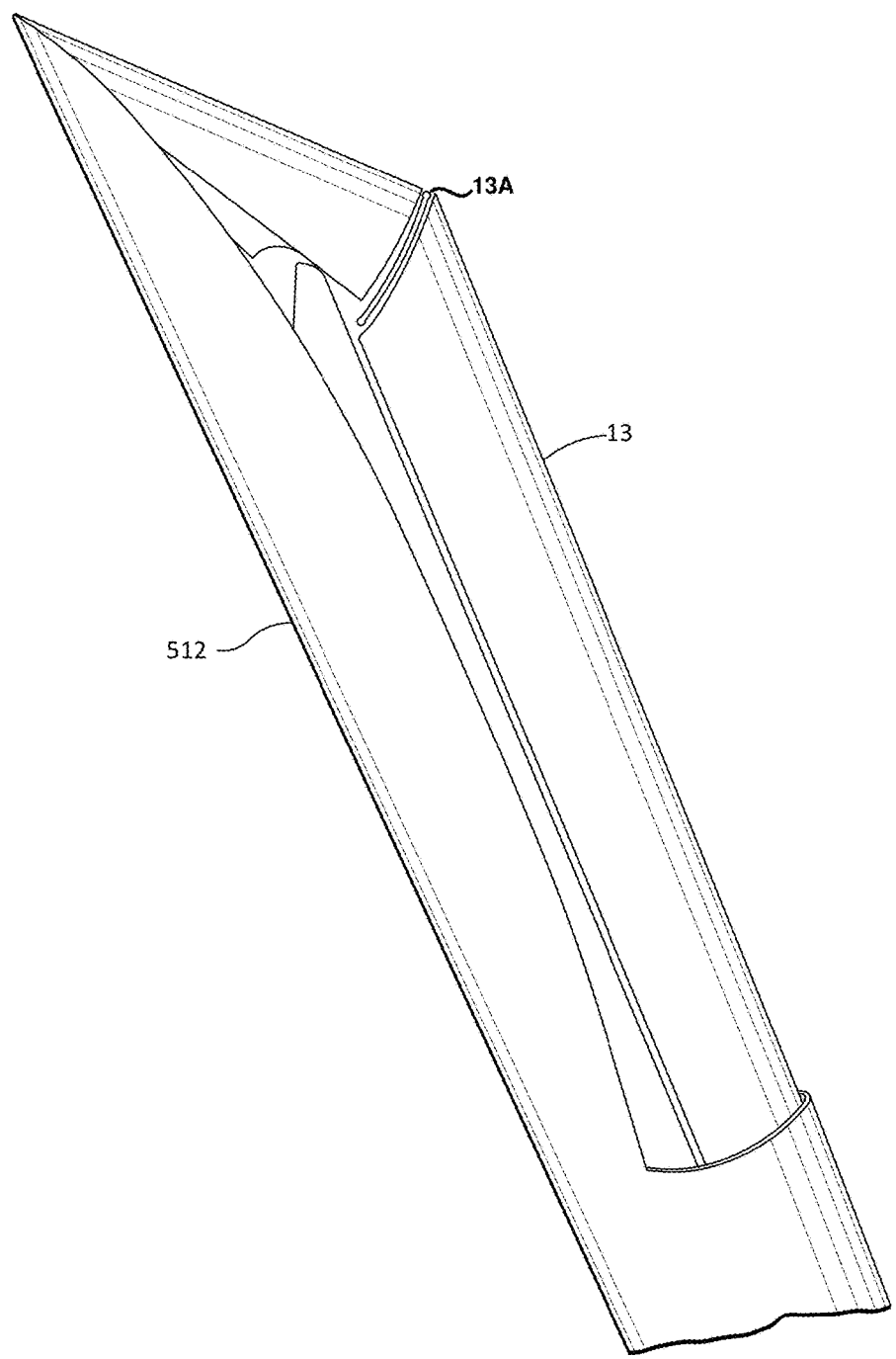
FIG. 11 is a side view of another embodiment of an outer sheath and inner cutting element.

FIG. 10, further to the points above, shows an active beak nearly completing its forced compliance with the inner diameter of a trough-shaped scoopula of an outer sheath element during a snapshot in time of its rotation/forward movement. It should be noted that sharp edges of an outer sheath scoopula 512 as shown may be beveled either externally or internally, according to embodiments. FIG. 11 shows the same components of FIGS. 9 and 10, but now showing an active single beak in close apposition with the forward edges of the scoopula section of an outer sheath 512. This illustration shows another embodiment of the shape of the edges of a trough or scoopula section, which, particularly if enabled to be oscillating, may aid in coring and thus facilitate the distal advancement of an entire distal portion of the biopsy device at the initial stages of the procedure. The edges of the scoopula may also be asymmetrical at any point relative to any other point, according to embodiments.

Figure 12:
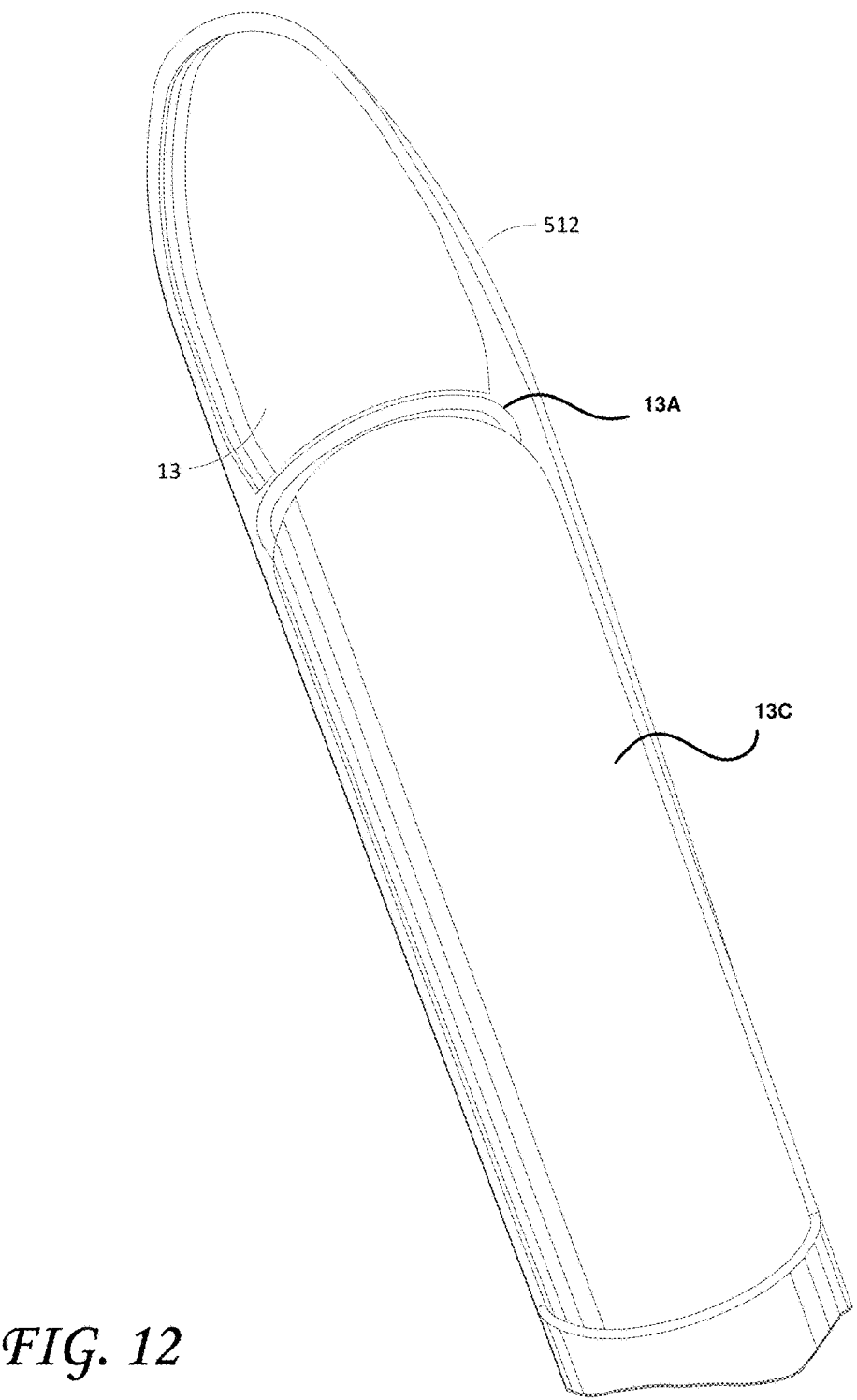
FIG. 12 is a top view of an outer sheath and cutting element aligned at its distal tip, according to one embodiment.

FIG. 12 shows the same components as are shown in FIGS. 9, 10 and 11, but from a top view perspective. This view shows a torsion bar 13A in close proximity to the proximal portion or base of an active beak 13 with respect to the upper half 13C of an extended collar portion of an active beak assembly, according to one embodiment. Various methods of attachment of a torsion bar to the base of a beak 13 may be envisioned, and are not specifically descried herein.

Figure 13:
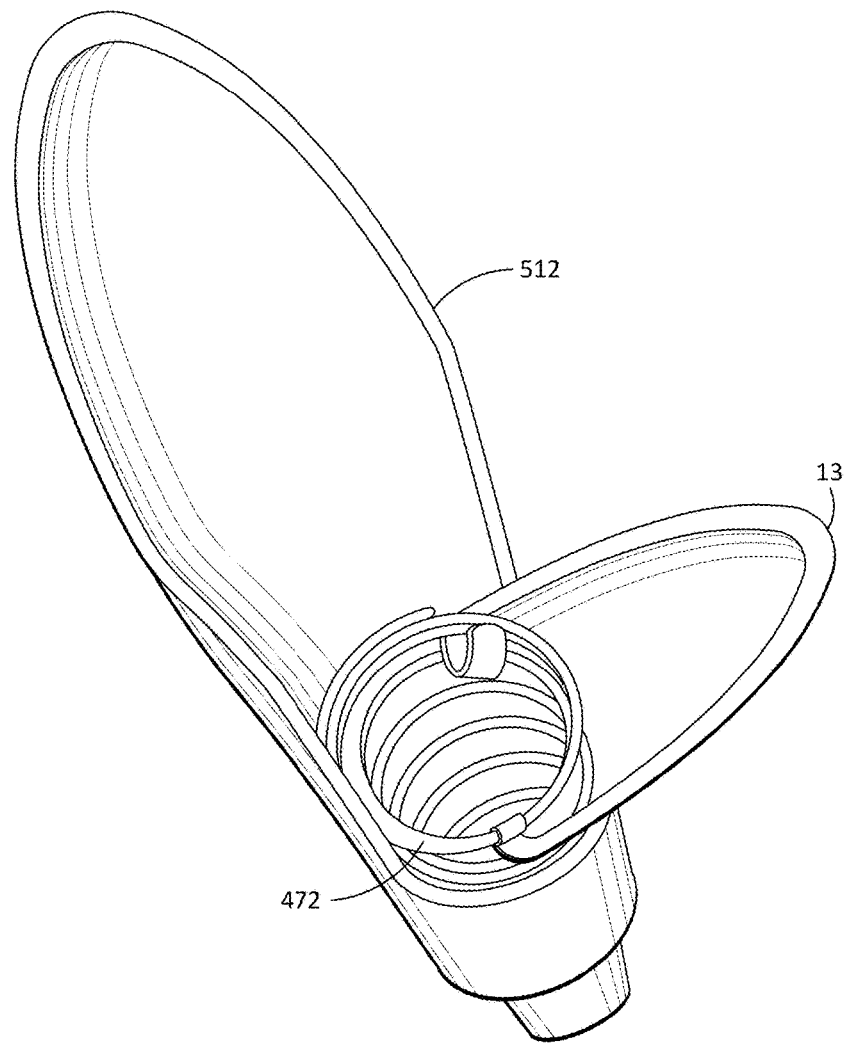
FIG. 13 is an end on perspective view of an outer sheath and inner cutting element in over center open configuration, according to one embodiment.

FIG. 13 shows the embodiment of FIG. 2, viewed facing the distal end. FIG. 13 shows an exaggerated beak opening for illustrative purposes. Couplings are shown mechanically linking a helical element 472 and the proximal portion of a moveable beak 13. Other coupling arrangements that couple a tubular coring and transport assembly (or, simply, the proximal end of the device) are possible and fall within the scope of this disclosure. Again, sharpened bevels of an outer sheath 512 and a beak 13 may be internal or external or opposite to one another.

Figure 14A:
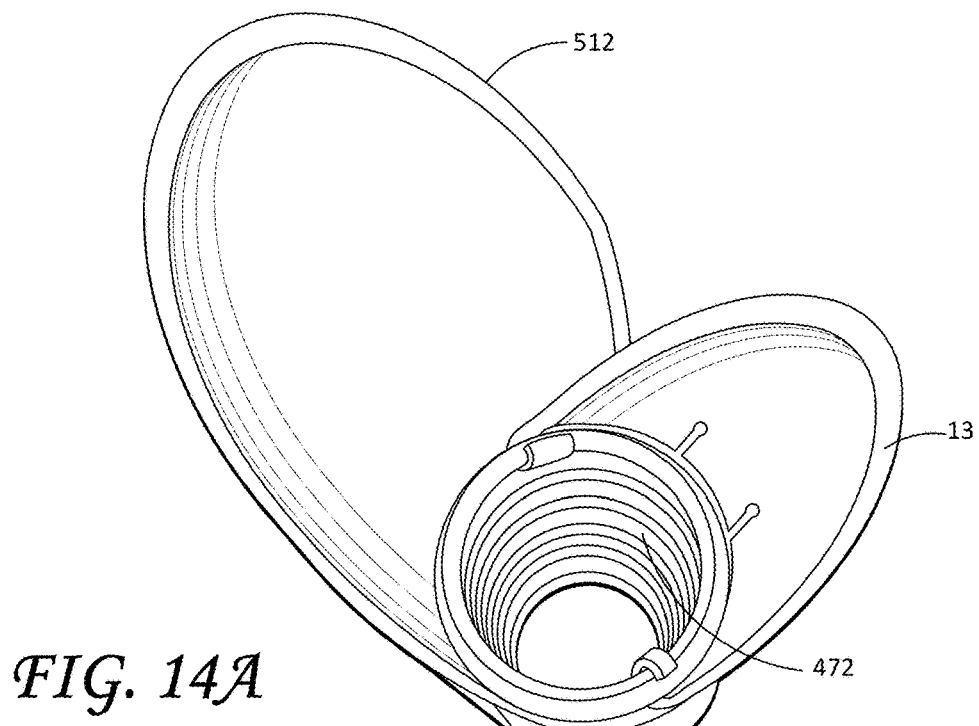
FIG. 14A is an end on perspective view of an outer sheath and inner cutting element in rotated position, according to one embodiment.

FIG. 14A shows the configuration of a tubular transport and coring assembly 11 of FIG. 13, showing forced compliance cycling of an active beak element 13 with the inside diameter of the scoopula portion of an outer sheath 512, according to one embodiment. In this case, the beak was opened over center, as in FIG. 13, and as rotation occurs, the beak must move back to a fully opened, but not over center, position, eventually as a straight extension of a helical element 472, until it moves past the opposite edge of outer sheath 512's scoopula and then can again open slightly over center.

Figure 14B:
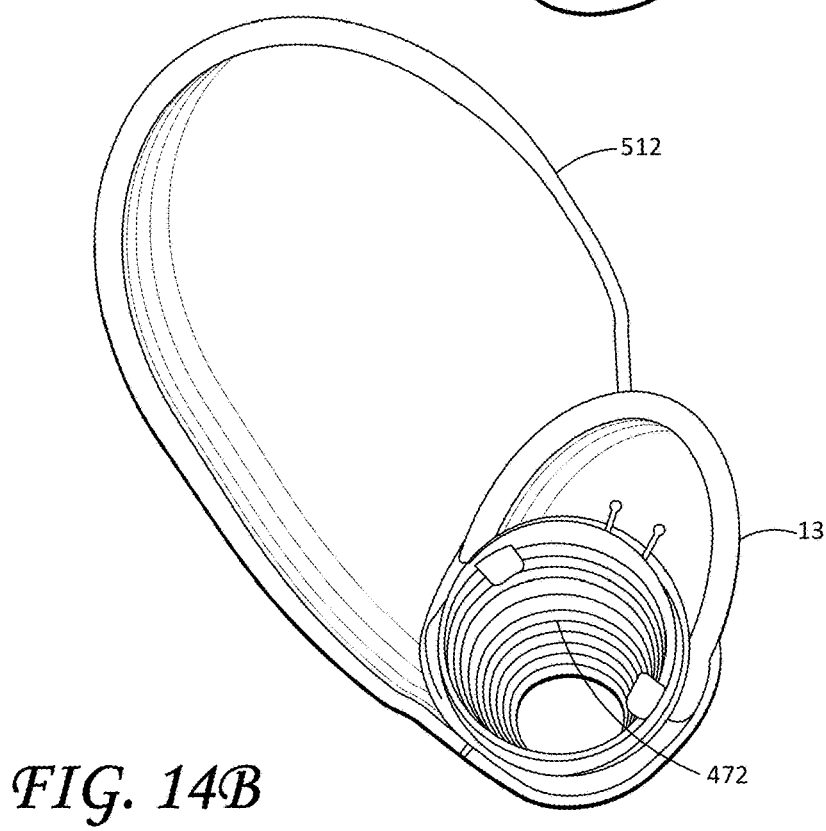
FIG. 14B is an end on perspective view of an outer sheath and inner cutting element in further rotated position, according to one embodiment.

FIG. 14B shows the features of components of FIG. 14A, according to one embodiment, but now showing nearly completed forced compliance of an active beak element 13 alignment with the inside diameter of the scoopula portion of an outer sheath 512.

Figure 15A:
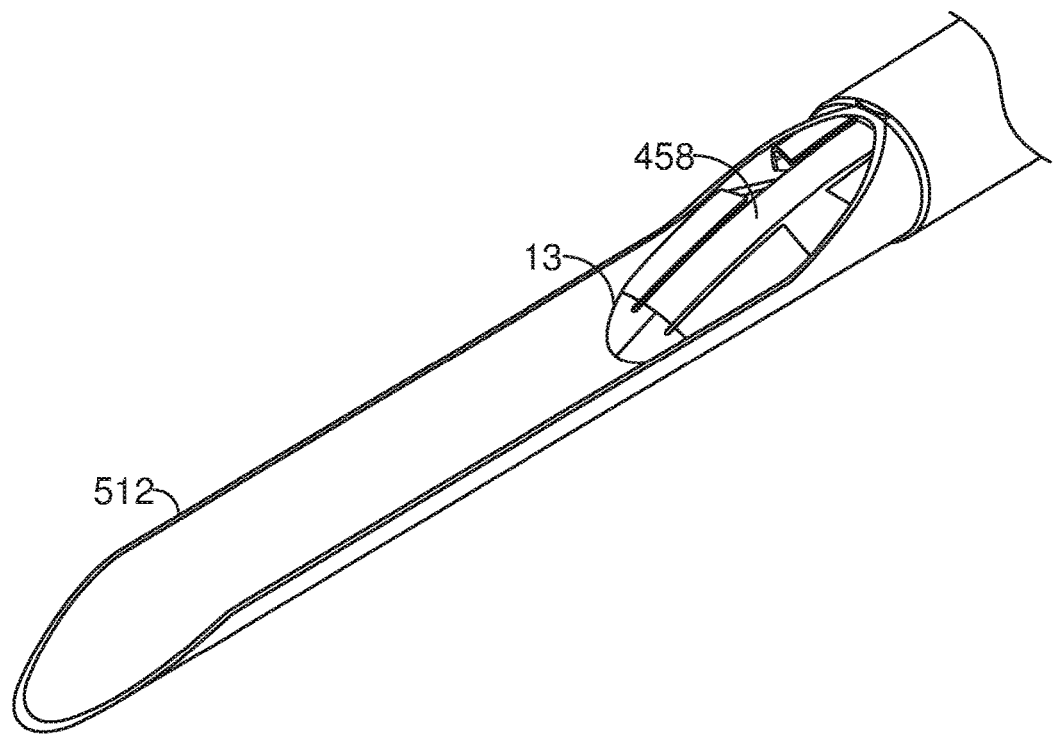
FIG. 15A is a perspective view of a split-tube single beak assembly in retracted position against an outer sheath with scoopula, according to one embodiment.

FIG. 15A is a perspective view of a split-tube single beak assembly 13 in retracted position against an outer sheath 512 that terminates in a scoopula. Shown in this view is a living hinge 458, which attaches a distal beak to an upper half 13C (FIG. 15B) of a split tube and which allows the beak 13 to close down against the inside diameter of a scoopula 512 of an outer sheath, as will be shown and described in later figures. Element 458 may be considered to be similar in function to the torsion bar 13A described relative to the previous FIG. 8 above. The action of a living hinge 458 provides positive attachment to both the distal tip of a beak assembly 13 as well as the upper half 13C of a split tube. The split tube may be similar in nature to a split collar upper half 13C and lower half 13D previously described, albeit longer than a split collar. The split tube may be of such a length as to be coupled directly to its own rotational and axial drive mechanism within a handle 12 of the biopsy device, to allow beak actuation and rotation. In the position shown in this figure, the beak 13 may not be rotating at all, in order to facilitate the forward penetration of the excisional device to a target tissue site within the body, as previously described above, according to embodiments.

Figure 15B:
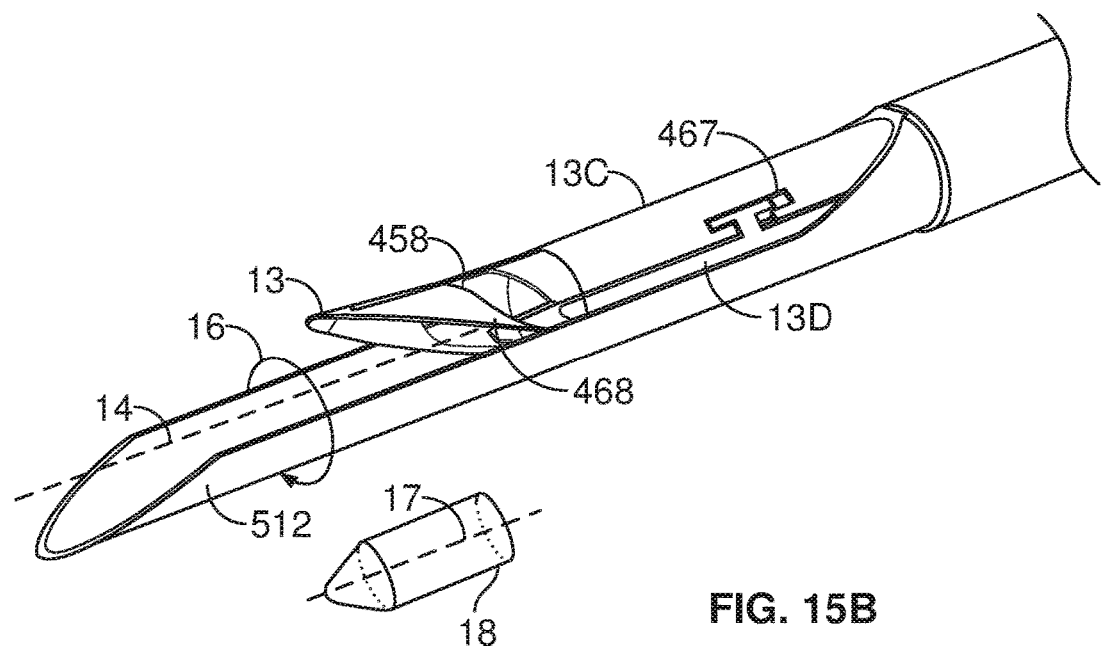
FIG. 15B is a perspective view of a split-tube single beak assembly extending part way out of an outer sheath, with the beak open over center, according to one embodiment.

FIG. 15B is a perspective view of a split-tube single beak assembly extending partly out of an outer sheath, with a beak open over-center and selectively under rotation about longitudinal axis 14 or not. According to one embodiment, the beak(s) 13 may also be configured to move substantially parallel to this longitudinal axis 14, as the beak(s) 13 move from a retracted position to a parting-off position in which the distal tip of beak 13 extends substantially to the distal tip of outer sheath 512, to thereby achieve substantially zero dead space. The over-center action of the beak is due to an attachment of two beak opening and closing tendons 468 formed with a beak (one on either side) and the lower half of a split tube, shown as element 13D in this view. The upper half of a split tube 13C may be attached to the proximal end of a living hinge 458. Relative axial movement between an upper half 13C and lower half 13D of the split tube actuates a beak 13 to open and close. Such axial movement may be limited, in embodiments, by a T-shaped or otherwise shaped tab that may be formed as part of a lower tube half 13D sliding within a travel limiting slot 467 in an upper half 13C of a split tube, according to one embodiment or opposite in other embodiments, as well as being of any shape. Several of these tabs and slots may be arranged along the length of a split tube, and the split tube, beak, living hinge and tendons may be formed of a single tube that may be, for example, laser cut. Additionally, the slot(s) 467 may be filled with a flexible substance, such as silicone, that may also be provided with a small hole that will open and close as a T-shaped tab moves axially in the slot. According to embodiments, this may allow flush fluids drawn between an outer sheath 512 and a split tube to selectively pass into the central lumen of a split tube to aid in tissue specimen transport. It should also be noted that according to one embodiment a single axially split tube may have more than one beak, configured with a movable beak attached to the upper half 13C of a split tube with a living hinge and tendons, as described above, and a fixed beak as a distal extension of the lower half 13D of the split tube, i.e., distal to the attachment points of the proximal ends of the tendons as an extension of the lower half 13D. Such a fixed beak in the lower half 13D may be thought of as a short scoopula, mimicking that of the outer sheath 512, but shorter, and in fact reaching distally only to the point where the movable beak would close down against it. In such an embodiment, the beak assembly would be capable of both coring and parting off a tissue specimen beyond the end of the outer sheath 512 scoopula, if desired. This embodiment is not illustrated, but may be easily envisioned by imagining that the split tube beak assembly of FIG. 15B had an extended fixed beak as part of the lower half 13D of the split tube. Under rotation, either a split tube single beak embodiment or a split tube double beak embodiment will part off a tissue specimen if the movable beak moves to at least the longitudinal axis 14 of FIG. 15B.

FIG. 15B also shows that at least the outer sheath 512 may be rotated, as suggested at 16. In so doing, the sharpened edge of the open scoopula-shaped distal portion of the outer sheath 512 cuts through an arc of tissue. According to one embodiment and as shown in FIG. 15B, the arc of tissue along 16 may be oriented substantially normal to the long axis 17 of the tissue specimen 18. That is, according to one embodiment, the open scoopula-shaped distal portion of the outer sheath 512 may be rotated about its longitudinal axis (e.g., 14 in FIG. 15B), which is normal to the long axis 17 of the tissue specimen 18. As also shown in FIG. 15B, the specimen 18 may (but need not) be shaped like a short segment of a tube, with tapered proximal and distal ends. After obtaining a first tissue specimen, further tissue specimens may be cut from the tissue then facing the open scoopula-shaped distal portion of the just-rotated outer sheath 512, which facing tissue may be radially separated from the tissue from which the previous, pre-rotation specimen was cut. After rotating the open scoopula-shaped distal portion of the outer sheath 512, a radially-directed force may be imparted on the biopsy device, to cause tissue to prolapse into the scoopula-shaped distal portion or to increase the amount of tissue that prolapses therein. This may increase the quality of the tissue specimen, depending upon, for example, the type and architecture of the tissue being cut.

Figure 15C:
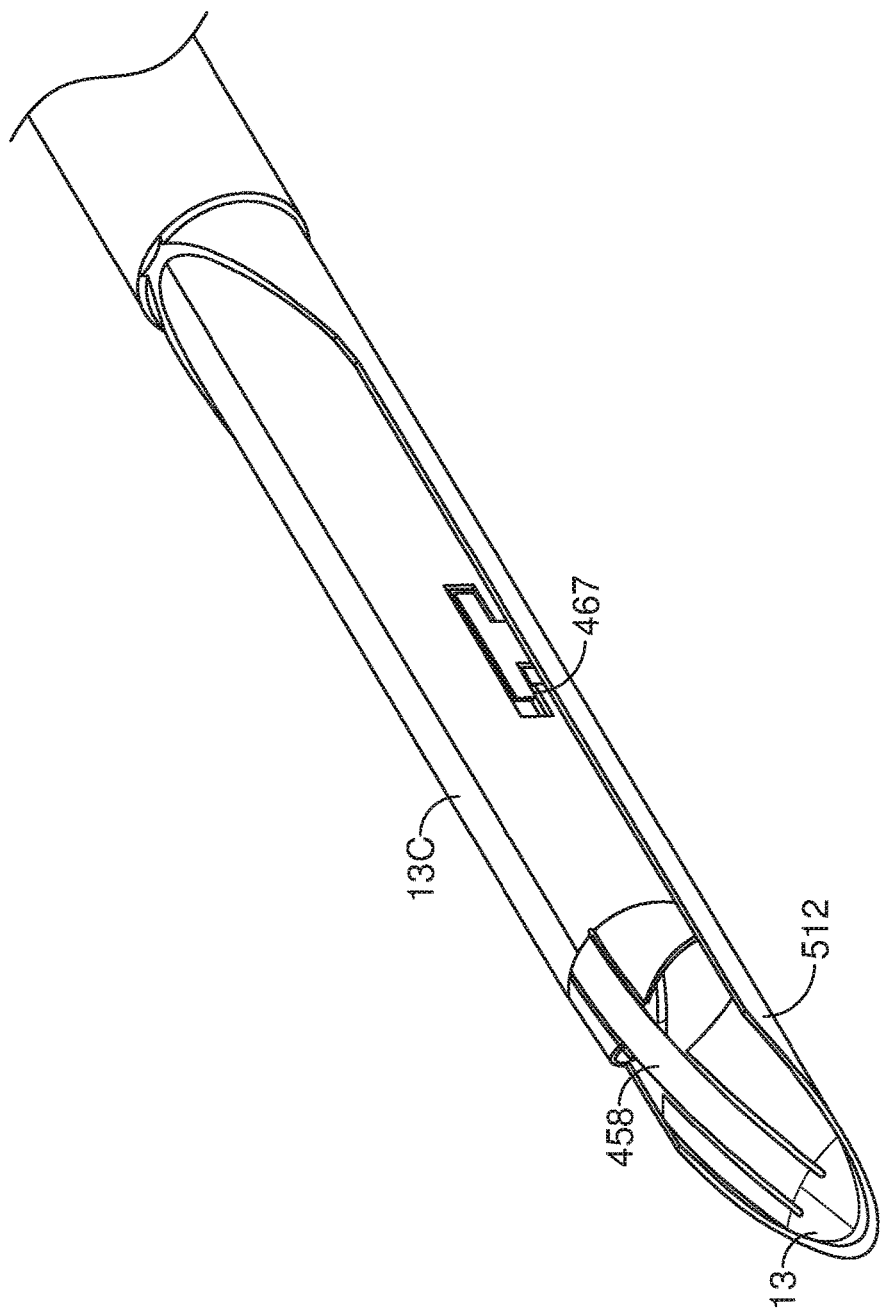
FIG. 15C is a perspective view of a split-tube single beak assembly in fully extended position at the end of the scoopula of an outer sheath for part off of a tissue specimen and for other purposes, according to one embodiment.

FIG. 15C is a perspective view of a split-tube single beak assembly in fully extended position at the end of the scoopula of an outer sheath, which position is suitable for part-off of a tissue specimen and for other purposes, including penetration to a target tissue site or repositioning to a second target site, according to embodiments. The elements of a living hinge 458, the distal tip of a beak assembly 13, an outer sheath 512, the upper half 13C of a split tube of such a monolithic beak assembly, and a slot 467 with its distance limiting tab may be seen in this view.

Turning now to further embodiments and in greater detail, the discussion that follows will focus on general features of an entire device 10 for purposes of illustrating its enabling mechanisms, which may comprise a distal end consisting of an outer sheath, an inner or distal sheath, a proximal sheath, work element or elements and such features as first, second and third helical elements, in any combination, as well as other elements such as suggested by FIG. 1 or previous figures and as detailed further below. The description below begins at the distal end and continues to the proximal end of the device 10, and embodiments may include any or all of these elements, according to individual embodiments.

Figure 16A:
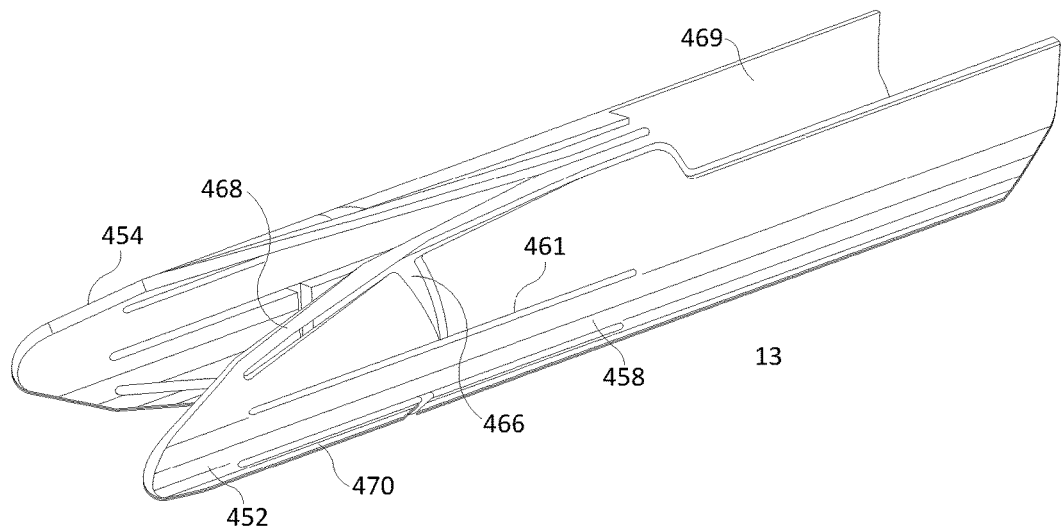
FIG. 16A shows details of a work element according to one embodiment.
Figure 16B:
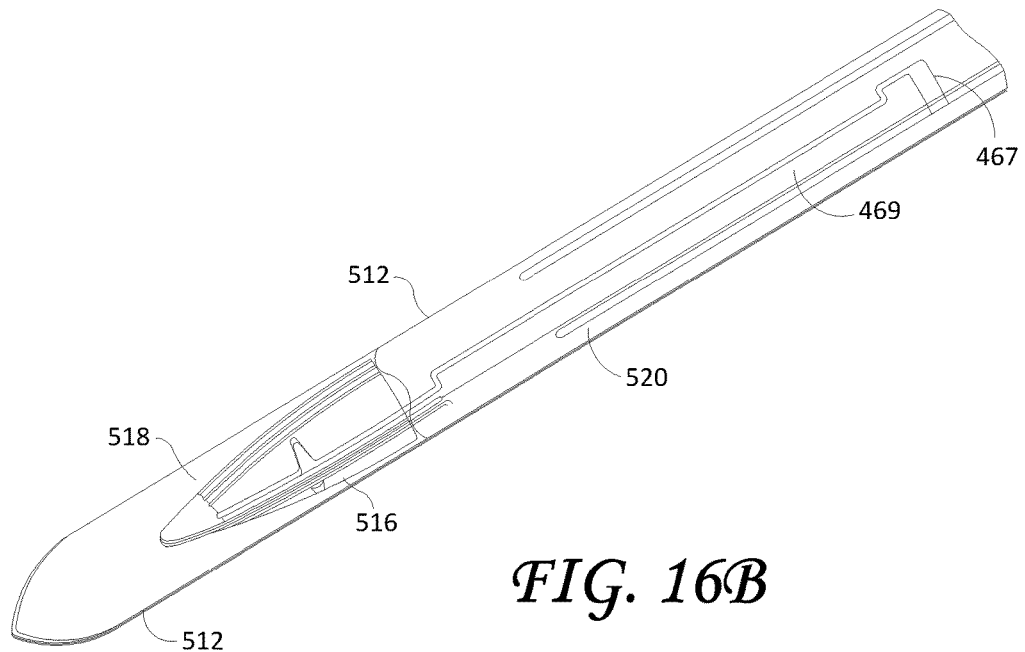
FIG. 16B show details of a work element and outer sheath of an excisional device according to one embodiment.

FIG. 16A shows details of a work element and FIG. 16B shows a work element in relation to an outer sheath 512 ending in a scoopula shape of an excisional device according to one embodiment. As shown, a first or, according to some embodiments, a first and second (or more) articulable beaks 13 may comprise one or more slot 461 defined therein to form a living hinge or hinges 458. For example slots 461 may have lengths ranging non-inclusively from 0.050 inches to 0.500 inches. The separation between adjacent slots 461 may also be in the range of 0.005 inches to 0.050 inches or up to ⅔ of the distal tube internal diameter. The thickness of living hinge 458 may be different in thickness than that of the surrounding material and may be in the range of 0.001 inches to 0.015 inches. The range of motion of the living hinges 458 may be from 5 degrees to 75 degrees with respect to the longitudinal axis of the outer sheath 512. Living hinges 458 could be fabricated from currently existing alloys such as a stainless steel, for example, 304, 316 or 440, in different tempers or work hardened states, nickel titanium alloys, maraging steel, composite materials such as made from fibers, for example, carbon fiber, and/or future high ductility alloys. Additionally, wedge-shaped (for example) cutouts 466, which may be left joined at the base of the wedge adjacent to slots 461, may be provided to define the articulable beaks of a work element 13, to improve the articulation thereof, and to provide for a great range of motion. According to embodiments, each of a first and second articulable beak tips 452, 454 may define or may be coupled to a first tendon 468 coupled to one side of the first articulable beak and a second tendon 470 coupled to the other side of the first articulable beak. Alternatively, a single tendon may be defined or multiple tendons may be defined. Additionally, these tendons may be defined at different relative angles to each other to impose an unequal or asymmetrical force to the sides of the distal end of an articulable beak tip 452 or 454, in embodiments. These first and second tendons 468, 470 may be configured to selectively apply a proximally-directed force and a distally-directed force to the distal portion of an articulable beak to cause the first and second articulable beak tips 452, 454 to assume their closed and progressively open configurations, respectively, or in the case of a single beak configuration, to open or close at some (which may be user-selectable) point along a scoopula of an outer sheath (as shown in FIG. 16B). Indeed, pulling on the first and second tendons 468, 470 by a proximal force acting on an actuating element 469 tends to close the first and second articulable beak tips 452, 454 (i.e., draw the respective distal tips closer to the longitudinal axis and closer to one another) and pushing on the first and second tendons 468, 470 tends to open the first and second articulable beak tips 452, 454 (i.e., draw the respective distal tips away from the longitudinal axis and away from one another). Tendons 468, 470 may be fabricated using the same engineering principles, concepts and material considerations as for the living hinge 458. Geometry of the tendons may be designed to ensure the full closure stress levels be kept in the 10 ksi to 360 ksi range. The width and height of the tendon element may have non-square and/or non-constant cross sections, as elliptical for example, in the range of 0.0005 inch to 0.015 inch on a side. The lengths of the tendon flexures could be in the range of 0.025 inches to 0.500 inches.

FIG. 16B shows a work element (shown as cutting elements 13 in the embodiment of FIG. 1) comprising, in one embodiment, twin articulable beaks 516 and 518 (numbered differently in this illustration to indicate that the entire beak or beaks may be comprised of many features already outlined in FIG. 16A) and outer sheath 512 of an excisional device according to one embodiment. As shown therein, an excisional device, according to one embodiment, may comprise an outer sheath 512 defining a longitudinal axis whose distal end, as shown, may comprise a scoopula (seen from the top down and shortened in this view, not necessarily to scale), trough or other leading edge shape. According to one embodiment, the distal edge or edges of such scoopula, trough or other distal feature may be sharpened at least partially around its circumference and side edges as desired. A work element may be configured to at least partially fit within an outer sheath 512 and may be configured to be withdrawn in the proximal direction into an outer sheath 512 and extend out in the distal direction at or near the end of the distal free end of a scoopula while lying within its curvature. The work element, according to one embodiment, may comprise a single beak (518, although 516 could be chosen as well since the work element rotates and such as single beak may act against the scoopula portion of the outer sheath 512 as shown in FIGS. 2-15 above). A beak 518 or 516 may be configured, including by its shape, according to one embodiment to close against the inside diameter of a scoopula at any point along its length, as shown in previous figures, as well as the distal-most edge of the scoopula, which shape may be similar to beak(s). The beak(s) may be configured to rotate within an outer sheath 512 about the longitudinal axis thereof. As shown in FIG. 16B and other figures, a first and/or first and second articulable beaks 516, 518 may define respective first and second curved distal surfaces configured to cut tissue. The work element may be further configured to be advanced distally such that at least a first and second curved distal surfaces of a beak or first and second articulable beaks 516, 518 are at least partially disposed outside of a distal outer sheath (not shown in FIG. 16B). As particularly shown in FIG. 13, a portion of both of the first and second curved surfaces of a single beak or of the first and second articulable beaks 516, 518 may be configured to rotate at least partially outside of an outer sheath 512, with the remaining portions thereof configured to rotate within an outer sheath 512.

Figure 20:
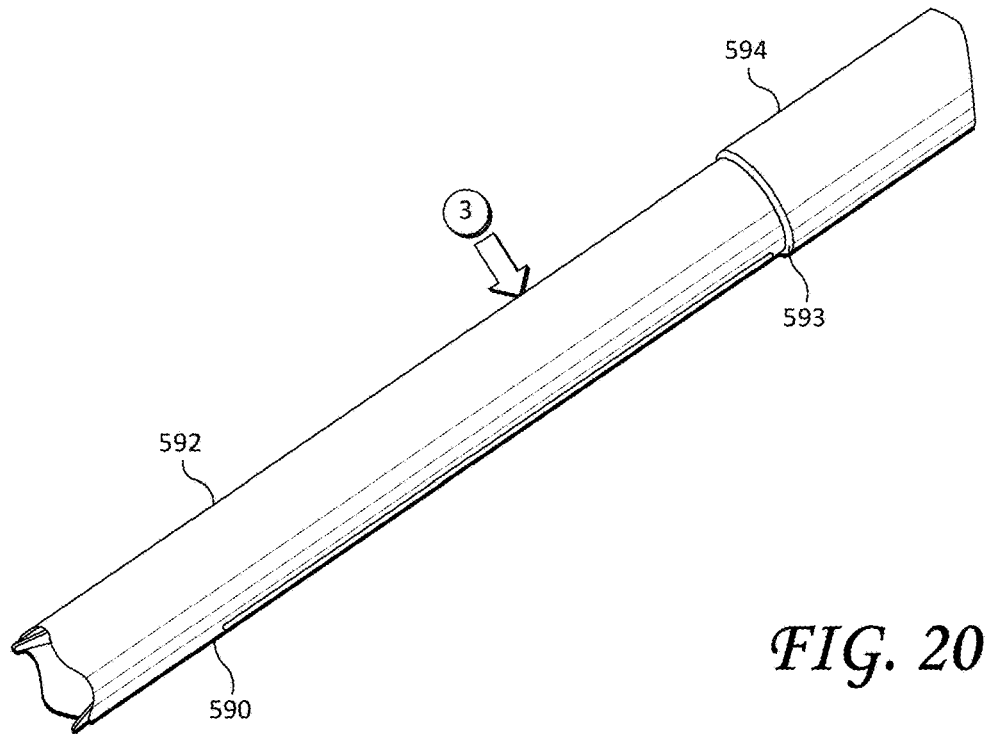
FIG. 20 shows an outer differentially rotating or rotatable outer sheath, which may function as a true outer sheath including an open but non-scoopula shaped extremity or as a distal sheath of an excisional device according to embodiments.

Indeed, in this embodiment, a substantial portion of a first and second articulable beaks 516, 518 may be configured to rotate within an outer sheath 512. This configuration radially supports a first and second articulable beaks 516, 518, and prevents them from over-extending or otherwise undesirable deforming when cutting through tough tissue. According to one embodiment, a shearing or scissors action may be imparted, as the distal tips of a first and second articulable beaks 516, 518 rotate inside the extremity of an outer sheath 512 and act with their sharpened edges against the side edges of an outer differentially or non-rotating sheath 512 as previously described. According to one embodiment, the shearing or scissors action occurs between the distal portions of a first and/or second articulable beaks 516, 518 against edges of a scoopula portion of an outer sheath 512. However, the first and second articulable beaks 516, 518 may also be configured to extend further out of an outer sheath 512, and in either a closed or open beak configuration. A closed beak configuration in which the work element extends only to the proximal opening of a scoopula of an outer sheath 512 may be well suited to advancing through tissue to the intended lesion site, with a closed first or first and second articulable beaks 516, 518 blocking tissue entry into the central lumen as a scoopula portion of an outer sheath 512 advances through the tissue. Alternatively, such extension of a first and second articulable beaks 516, 518 outside of an outer sheath 512 may constitute a phase of a combined rotational/closing and part-off action following coring of the tissue accomplished with a first and second articulable beaks 516, 518 at least partially enclosed within an outer sheath 512. Finally, extension of a first and second articulable beaks 516, 518 in either the closed or open configuration may be accomplished either by extending them in the distal direction and/or retraction of a distal sheath 592 (as shown in FIG. 20 below), in relation to cored or to-be-cored tissue. To limit the extend of force that may be applied to the first and second tendons 468, 470 and thus on the first and second articulable beaks 516, 518, the work element 13 may comprise travel limiter structures 467 (only one of which is visible in FIG. 16B, but also similar in function to that shown above in FIG. 15C, for example). Indeed, as shown in FIG. 16B and according to one embodiment, the travel in the distal and proximal directions of the beak actuating elements 469 may be limited by interlocking tab and slot features of various shapes that only allow a limited relative travel between the constituent elements thereof. Such limited travel is sufficient, according to one embodiment, to fully open and to fully close a first or a first and second articulable beaks 516, 518.

The distal free end of an outer sheath 512 may be shaped as desired and may comprise, as shown in FIG. 16B, a scoopula (or a trowel- or trough-like, for example) shape. This distal edge may be sharpened, to aid in the penetration into and coring of tissue. Vacuum slots may be provided within an outer sheath, as shown at 520. Should a vacuum be drawn within the lumen of an outer sheath 512, surrounding tissue may be drawn thereto, thereby assisting in stabilizing the distal end of the excisional device during the specimen cutting procedure. Vacuum slots 520 may also serve to collect liquids and free cells from the surrounding tissue or to deliver liquids to the surrounding tissue. They may also serve as an opening at the distal end of the device so that as vacuum is applied internally at the proximal end of an outer sheath 512 as an aid in transporting tissue specimens proximally, a corresponding vacuum is not built up behind (distally to) the tissue specimens. Avoidance of vacuum buildup distal to the tissue specimens may facilitate tissue transport in the proximal direction as well as prevent tissue specimens from acting as plugs in the work element. Slots may also be provided in the trough of a scoopula itself as an aid to imaging devices to sharpen visibility of a scoopula in relation to surrounding tissues.

The shape of the sharp cutting elements beak (or work) assembly 13, such as the embodiment thereof shown in FIGS. 1 and 16A and 16B, for example, provides substantial support for all movements required of the cutting beaks during rotation, opening/closing and axial motions (not shown). Using the nomenclature of FIG. 1 in particular, this embodiment enables the sharp cutting elements of beak assembly 13 to be made extremely thin, which fulfills a requirement that for any given outer radial dimension of a tubular coring and transport assembly (including the cutting beak assembly) 11 see also FIG. 1), the caliber of the core sample retrieved from the patient will be as large as possible. The shape(s) of the sharp cutting elements of beak assembly 13 specified for use in coring and part-off according to embodiments enable the biopsy device 10 to core a full diameter, and in fact larger than full diameter with respect to the dimensions of the coring and transport assembly 11, of which slightly larger caliber (e.g., diameter) may be desirable in order to compress, "stuff", or pack in as much tissue sample into the tubular coring and transport assembly 11 as possible, which may prove advantageous from several standpoints (including diagnostic, clinical standpoints) or provide more sample (not shown) for analysis.

According to one embodiment and as described herein, a work element 13 of FIG. 1, including articulable beak(s) 516 and 518, or 516 or 518 alone of FIG. 16B, may be configured for rotation within an outer non- or differentially-rotating outer sheath(s), such as 512 of FIG. 16B. Moreover, the articulable beak(s), according to one embodiment, may comprise a surface having substantially the same curvature as the body portion of the work element 13. The body portion of the work element may be that portion thereof that is proximal to the articulable beak or beaks. According to one embodiment, the articulable beak(s) may be generally described as being or comprising one or more hyperbolic segments of one or more sections of a hollow cylinder, such as a hypo tube. Variations including complex curves may be incorporated into the shape of articulable beak(s) to optimize function in different sections of, for example, the edges of the articulable beaks. Moreover, first and second articulable beaks, according to embodiments, may have slightly different shapes from one another. The angle formed by the distal portion of first and second articulable beaks or between a single articulable beak and scoopula may be, for example, from about 5 to 75 degrees. According to one embodiment, the angle may be between about 10 and 30 degrees. According to another embodiment, the angle formed by the distal portion of first and second articulable beaks or first beak and a scoopula may be about 18 degrees.

Note that, according to one embodiment, the entire work element, including a first or first and second articulable beaks 516 and 518 of beak assembly 13 along with first and second tendons, beak actuation mechanisms such as 469, living hinges 458 (as best shown in FIGS. 15C and 16A) connecting a single or first and second articulable beaks to the body portion of the work element, travel limiter structures and, as described below, a first helical element may all together comprise a single monolithic structure formed of a same material that may be (e.g., laser-) cut from, for example, a single solid hypo tube. That is, these structures may be formed together of a same piece of unbroken homogeneous material whether a single split tube is selected or whether a non-split tube is selected, according to embodiments. Such a monolithic structure may be considered to be a monolithic work assembly, and may take the form of a monolithic beak assembly, which is but one embodiment thereof.

Figure 17A:
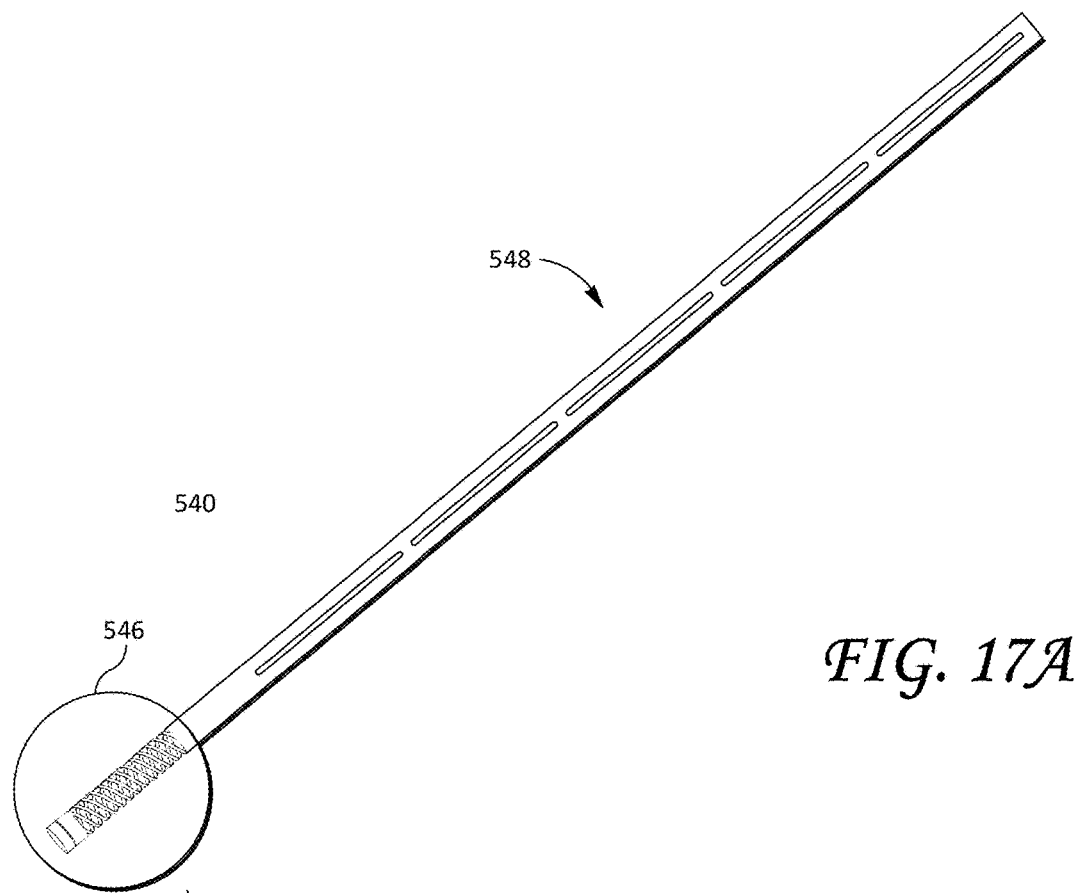
FIG. 17A shows an element of an excisional device according to one embodiment.
Figure 17B:
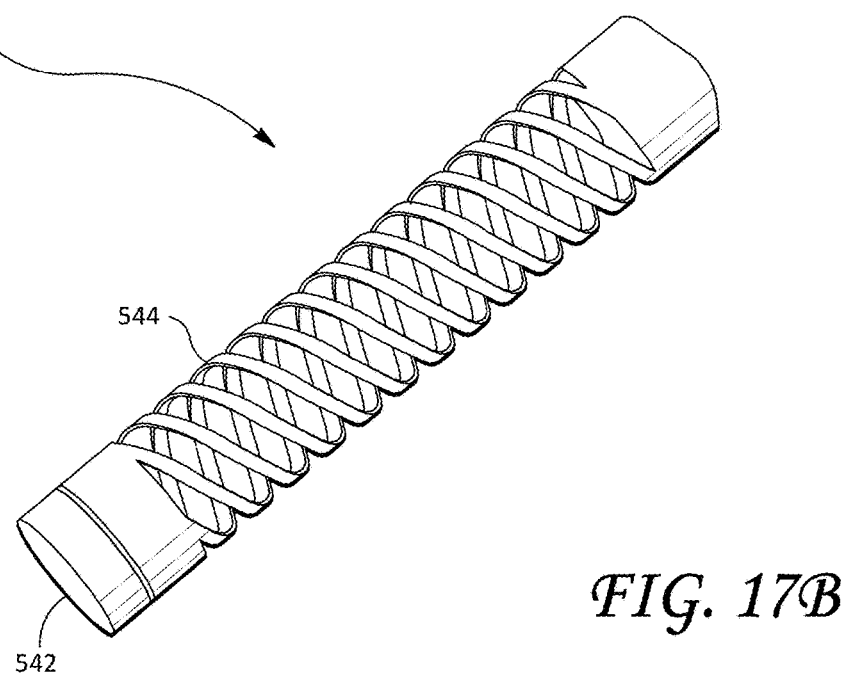
FIG. 17B shows a detail of an element of an excisional device, according to one embodiment.
Figure 19:
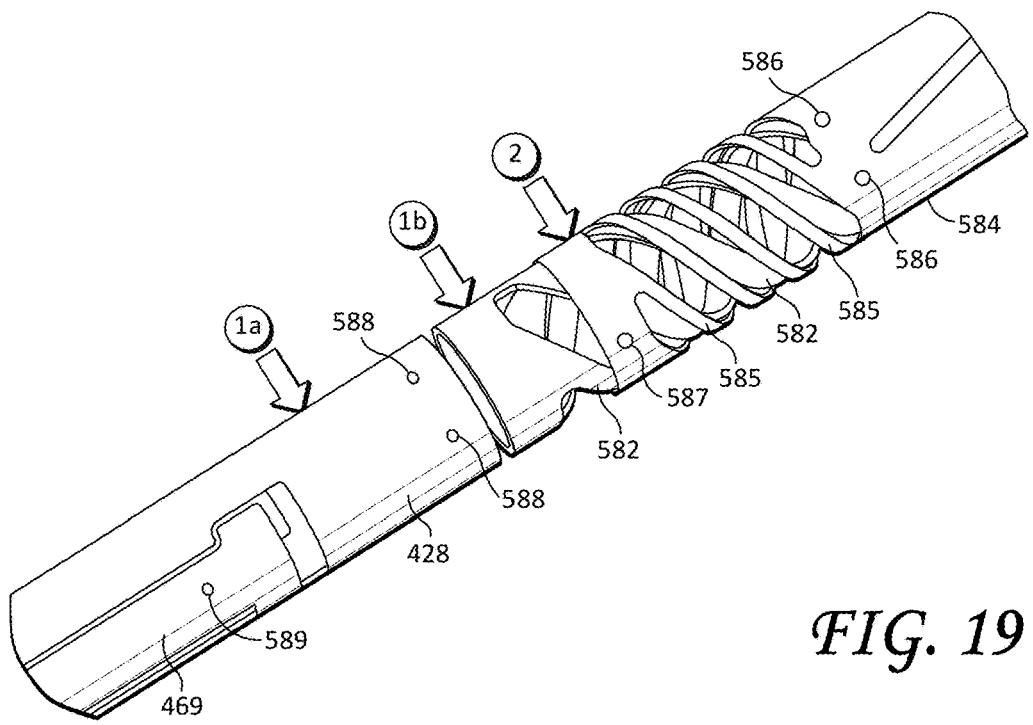
FIG. 19 shows details of a proximal sheath, beak actuation elements and inner helical element of an excisional device according to one embodiment.
Figure 21:
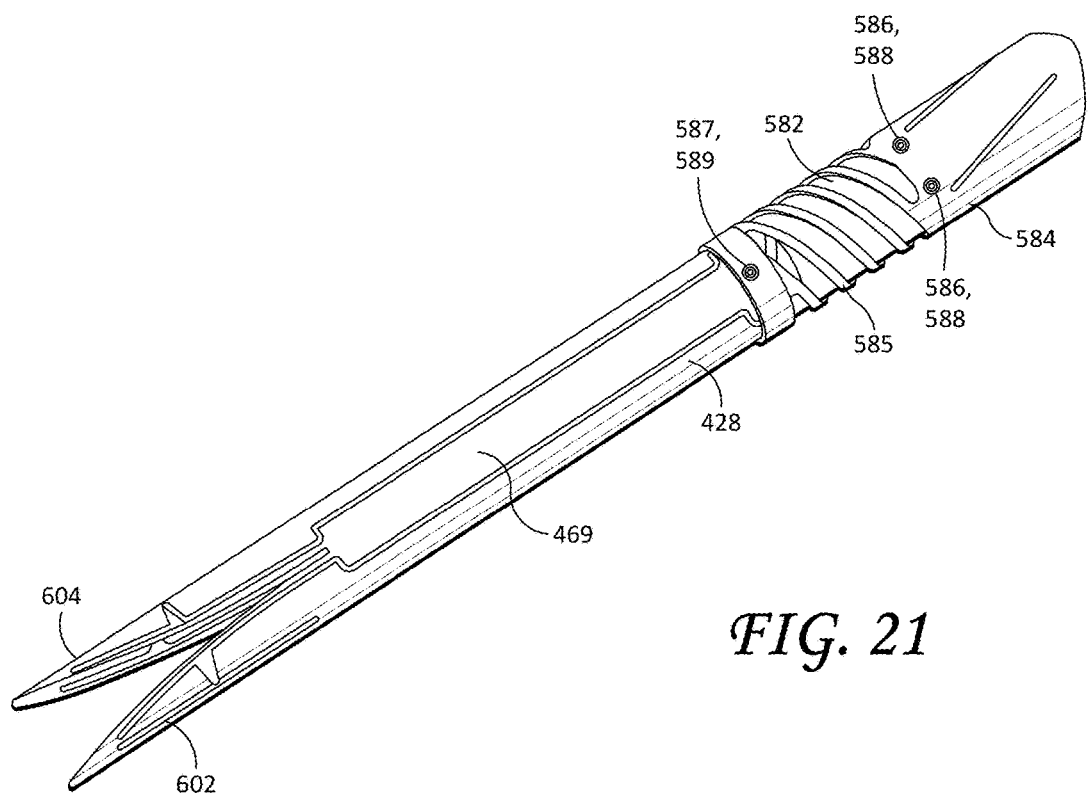
FIG. 21 is a view of a twin beak work assembly of an excisional device with the distal sheath and outer sheath removed, according to one embodiment.

Continuing to describe additional elements of a tubular transport and coring assembly 11 of FIG. 1, according to embodiments, FIGS. 17A and 17B show an intermediate, proximal sheath 540 of an excisional device 10, according to one embodiment, without showing any additional non- or differentially-rotating distal and outer sheaths. According to one embodiment, a proximal sheath 540 may be configured to fit over at least a portion of a work element 13 (as shown later in FIG. 21) and abut collar 542, which collar may be nothing more than an internal shoulder within a distal sheath 590, such as shoulder 593 in FIG. 20 below. According to one embodiment, a proximal sheath 540 may be configured to resiliently bias a first and second articulable beak 518 or beaks 516 and 518, if twin (or multiple) beaks are used, in the open position. According to one embodiment, a proximal sheath 540 may be slid over the proximal portion of a work element 13 and then further advanced over the work element 13 until the distal end of the proximal sheath 540 abuts against a collar 542 (or shoulder 593 of FIG. 20). Therefore, as will be described below relative to FIG. 21, selectively acting upon (e.g., exerting a proximally-directed or distally-directed force on) the proximal portion 548 of a proximal sheath 540 causes a first and second articulable beaks 516, 518 to open and close. If only one beak is present, that beak may be configured to open and close against, for example, an otherwise immobile scoopula-shaped portion of an outer sheath 512, as previously described above. According to one embodiment, a proximal sheath 540 may itself be enclosed by an outer non- or differentially rotating distal sheath 590, which effectively captures the distal portion 546 of a proximal sheath against an outer sheath 512, as shown in FIGS. 20 and 21 further on. Thus, a proximal sheath may act in concert with a distal sheath 590, as shown in FIG. 20, over at least a portion of the work element 13 to cause a first and second articulable beaks 516, 518 to open and close. According to one embodiment, the proximal sheath 540 may be either free floating or driven in rotation, and may be non- or differentially rotating with respect to any outer sheaths as described further on. According to another embodiment further detailed below, collar 542, which is primarily shown for illustrative purposes, may be eliminated and a beak actuating portion 469, as shown in FIG. 16A, and a body portion 428, as shown in FIG. 19, of the working element 13 may be directly attached to a proximal sheath 540 at the distal and proximal ends of a helical portion 544 of the proximal sheath. In such an embodiment, the work element 13 may be attached to a proximal end of such a second helical element 544 to rotate the work element 13, including a first and second articulable beaks. In this manner, a proximal sheath 540 may be configured to entrain the work element 13 in rotation as well as to open and close articulable beaks. In such an embodiment, a first helical element 472, such as previously shown in FIGS. 2-6, may be decoupled from the work element 13, thereby enabling a first helical element 472 to be driven at a rotational speed that is independent of the rotation speed of a connected proximal sheath 540 and a first or a first and second articulable beaks 518 or 516, 518, as is shown and discussed in greater detail below. According to one embodiment, to bias a first and second articulable beaks 516, 518 in the open position, at least partially within an outer sheath 512, according to one embodiment, a proximal sheath 540 may comprise such a second helical element 544. In this manner, according to one embodiment, not only may the present biopsy device comprises a first or a first and second helical elements, but such helical elements may be co-axially arranged within the device, one over the other. According to one embodiment, at least a portion of a second helical element may fit over a first helical element within the biopsy device to effectively define a structure comprising a coil-within-a-coil, as shown in FIG. 19.

According to one embodiment, a proximal sheath 540 may comprise a proximal region 548 and a distal region 546 comprising a second helical element 544. The proximal region 548 may be generally co-extensive with at least a portion of a first helical element 472, if included in such embodiment, of the work element and may comprise structure configured to aid in the proximal transport of a severed tissue specimen. Indeed, after being severed from surrounding tissue, the cored specimen will be urged in the proximal direction within the body portion of the work element 13 and eventually engage such a rotating first helical element, if used, or engage a flush conduit that aids tissue transport. A first helical element, if present according to embodiments, may assist in the transport of the cored specimen to, e.g., a tissue collection transfer magazine 27 coupled to the present biopsy device. Surface features may be provided on the inner lumen of a proximal sheath 540 which, however configured, may aid in the transport of cored specimen by providing some measure of friction between the cored specimen and a rotating first helical element 472, if used, to enable the cored specimen to move in a proximal direction through the device. According to one embodiment and as shown in FIGS. 19 and 21 further on, when a proximal sheath 540 is filled over the work element 13, tissue entrained by a first helical element, illustrated by 582 of FIGS. 19 and 22, will also be drawn against the inner lumen of a proximal sheath 540. According to embodiments, a flush and a vacuum may be drawn within at least a proximal sheath 540. In this manner, cored tissue specimen(s) may be drawn through the coils of a first helical element, if present, to come into intimate contact with the (e.g., patterned, or slotted) surface of a proximal sheath's inner lumen. Alternatively, in other embodiments, only the flush fluid and vacuum, acting in concert but without a first helical element, may suffice to ensure tissue specimen transport to a transfer magazine. The flush may be provided with flow rates ranging from 0 to 100 cubic centimeters per minute. The vacuum may be provided with a pressure range from atmospheric to 0.001 Torr and may have flow rates ranging from 0 to 200 cubic centimeters per minute.

Figure 18:
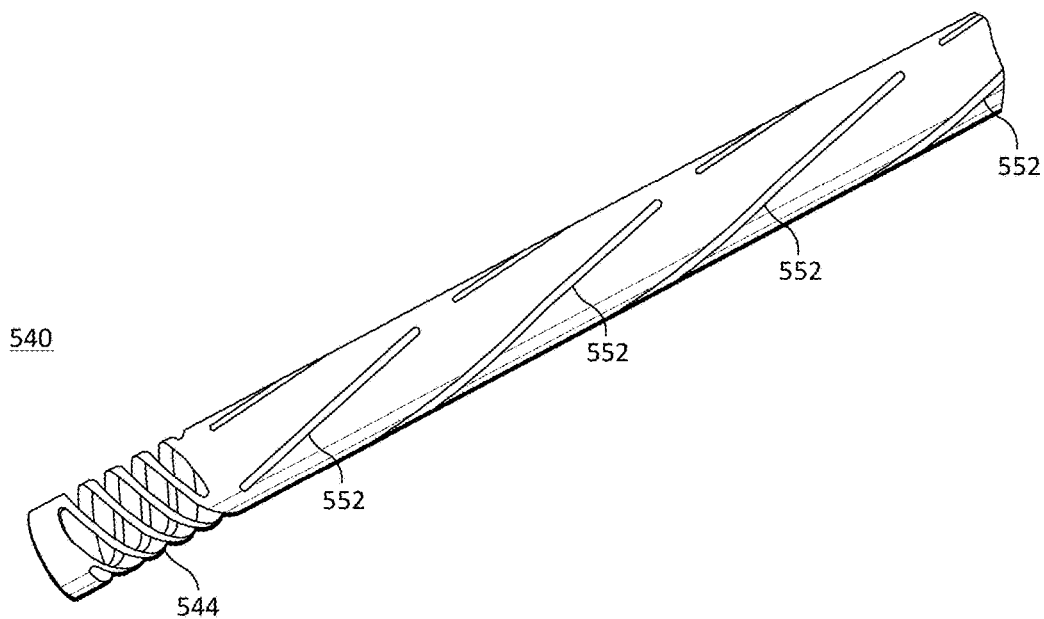
FIG. 18 shows a proximal sheath comprising a plurality of elongated slots disposed in a spiral pattern around a longitudinal axis, according to one embodiment.

As shown in FIG. 17A, and according to one embodiment, a proximal sheath 540 may define one or more elongated slots 552 therein. FIG. 18 shows a proximal sheath 540 comprising a plurality of elongated slots 552 disposed in a spiral pattern around a longitudinal axis and serving as a helical element, according to one embodiment. Such slots 552 may allow fluid communication with the interior lumen of a proximal sheath 540. In other words, a slot or slots 552 may go all of the way through the wall thickness of a proximal sheath 540. For example, when vacuum is drawn within a proximal sheath, cored tissue specimens being transported by a first rotating helical element 582, if used, may be drawn to slots 552, and partially invaginated therein, providing some resistance to the cored tissue specimen, thereby preventing them from simply rotating in place within a first helical element without moving. Slots 552 may also serve as conduits for flushing liquids used to aid transport in concert with aspiration applied from a vacuum source within or external to the device 10. According to one embodiment, slots 552 may be serially disposed end-to-end substantially parallel to the longitudinal axis of a proximal sheath 540, as shown in FIG. 17A, may be offset relative to one another, or may be disposed in a spiral pattern, whether non-overlapping or overlapping, as shown in FIG. 18, thus effectively acting as an elongated co-axially disposed third helical element of similar or different pitch than a second helical element similar to that discussed under FIG. 17B above.

FIG. 18 shows one embodiment where a proximal sheath 540 includes slots 552, as previously shown in FIG. 17A, in an overlapping spiral pattern, which slots 552 may effectively function as a third helical element co-axially disposed relative to a first helical element 582 and second helical element 544. The slots 552, according to one embodiment, may be configured to provide resistance to the cored tissue specimen to enable a first helical element to transport the tissue specimen in the proximal direction. It is recalled that a first helical element may be decoupled from the work element 13 (including the first and second articulable beaks), and that a proximal sheath 540 may be mechanically coupled to tendon actuating elements 469 (and, also, to a first or first and second articulable beaks) to provide both rotational force and beak opening and closing actuation, as described relative to FIGS. 19 and 21. In such an embodiment, therefore, the relative speeds of rotation of a first or first and second articulable beaks and a first helical element may be driven independently and differentially tuned to optimize both tissue coring and tissue specimen axial transport in a proximal direction (e.g. to a transfer magazine 27 of a device 10).

FIG. 19 shows details of a proximal sheath, beak actuation elements and an inner first helical element, according to embodiments. It is to be noted that the figures herein are not to scale and the relative dimensions of the constituent elements of the biopsy device 10 may vary from figure to figure. According to one embodiment, the working end (e.g., substantially all structures distal to the handle 12) of the biopsy device 10 may be essentially composed or formed of two or more separate elements that are disposed substantially concentrically or co-axially relative to one another. This results in a mechanically robust working end of the excisional device that is economical to manufacture and to assemble.

As shown in the exploded view of FIG. 19, one embodiment comprises a work element that comprises a body portion 428 and tendon actuating elements 469 (only one of which is shown in this view), and may be terminated by a first and/or second articulable beaks (not shown in this view). A first helical element 582 may be formed of the same material as the work element 13. According to one embodiment, the work element 13 (i.e., a body portion 428, a tendon actuation element 469 and a first or first and second articulable beaks) and a first helical element may be cut or formed from a single piece of material such as a hypo tube. For example, the hypo tube may be suitably (e.g., laser) cut to form the body portion 428, the tendon actuation elements 469, the first and second articulable beaks as well as a first, helical element 582. A first helical element 582 may then be mechanically decoupled from the work element 13 by cutting the two structures apart. These two structures are, therefore, labeled (1a) and (1b) in FIG. 19, to suggest that they may have been originally formed of a single piece of material. That a first helical element is mechanically decoupled from the work element 13 enables the rotation of a first helical element 582 to be independent of the rotation of the work element 13. For example, a first helical element 582 may rotate at a comparatively slower rate than the rate of rotation of the work element 13, as transport of a severed tissue specimen may not require the same rate of rotation as may be advisable for the work element 13. According to further embodiments, a first helical element 582 may be deleted, leaving an expansion chamber in its place, relative to the central lumen inside a proximal sheath 540 (not shown in this figure), since the diameter of a proximal sheath 540 is greater than the diameter of the beak assembly 13 to which it may be fixed, thus providing an expansion chamber proximal to the proximal end of the beak assembly 13. In such embodiment, a proximal sheath could extend proximally to a transfer magazine 27 at a vacuum tight junction.

The second of the three main separate elements of the working end of the biopsy device, in one embodiment, is a proximal sheath 584, as shown at (2) in FIG. 19. A proximal sheath 584 may comprise, near its distal end, a second helical element 585 (similar to 544 of FIG. 18). As shown in FIG. 19, a second helical element 585 may be disposed concentrically over a portion of a first helical element 582. According to one embodiment, a proximal sheath 584 may comprise one or more proximal locations 586 and one or more distal locations 587. The proximal and distal locations 586, 587 may define, for example, indentations, obrounds or through holes and may indicate the position of, for example, spot welds (or other attachment modalities) that are configured to mechanically couple a proximal sheath 584 with the west element of the biopsy device. When assembled, a proximal sheath 584 may be concentrically disposed over a first helical element 582, if present in such embodiment, and advanced such that the one or more proximal locations 586 on a proximal sheath 584 are aligned with corresponding one or more proximal attachment locations 588, if present, on the work element 13 and such that one or more distal location 587 on a proximal sheath 584 is aligned with corresponding one or more distal attachment location 589 on a tendon actuating element 469. The corresponding locations 586, 588 and 587, 589 may then be attached to one another. For example, one or more proximal locations 586 on the proximal sheath 584 may be spot-welded to corresponding one or more proximal attachment locations 588 on the work element 13 and one or more distal location 587 on the proximal sheath 584 may be spot-welded to corresponding one or more distal attachment location 589 on a tendon actuating elements 469.

It is to be noted that locations 586, 587, 588 and 589 are only shown in the figures as illustrative and exemplary only, as there are many ways of mechanically coupling or attaching a proximal sheath 584 to the work element 13, as those of skill may recognize. According to one embodiment, a proximal sheath 584 may be attached such that movement of a second helical element 585 (e.g., extension and concession) corresponding actuates a first beak (and, if present, a second articulable beak) between a first (e.g., open) configuration and a second (e.g., closed) configuration. Indeed, a proximal sheath 584 may be mechanically coupled to the work element of the biopsy device such that, for example, a proximal portion thereof (e.g., at or in the vicinity of proximal locations 586) is attached to a body portion 428 of the work element 13 and such that a distal portion thereof (e.g., at or in the vicinity of distal location 587) may be attached to a tendon actuating elements 469. In this manner, compression and extension of the second helical element 585 may cause a relative displacement of a tendon actuation elements 469 and a body portion 428 (i.e., one may move while the other is immobile or substantially so, or both may move relative to one another), thereby causing the actuation of a first or first and second articulable beaks.

FIG. 20 shows a non-, differentially, or same-speed rotating distal sheath 590, (which may also serve as an outer sheath 512, wherein a scoopula of such structure may extend from about 1 millimeter to more than 200 millimeters, according to embodiment) which may or may not, according to embodiments, extend over a first or first and second articulable beaks. It should be noted that differential rotation may also imply not only a difference in relative speeds between two elements, such as a proximal and distal sheath, but also that the direction of rotation may be different, according to embodiments. Such opposite rotation serves to increase the relative concentric rotational speed between the two elements, while allowing simplification of the corresponding drive mechanisms, which may thus not have to be rotated at the high speeds necessary to achieve a certain relative speed differential between two such elements. The third (labeled as 3 in this figure as its proximal end is of greater diameter than 1 and 2 of FIG. 19) of the three or four coring and transport assembly 11 elements, according to certain embodiments, is a distal sheath 590 which may be configured to fit over the work element 13 as shown in FIG. 19 comprising a body portion 428, a tendon actuating element 469 and at least a portion of a first or first and second articulable beaks. A distal sheath 590 may also be configured to slide and fit over a proximal sheath 584 that is mechanically coupled to the work element 13. When the distal sheath 590 is combined with a proximal sheath 584 and work element 13, it may be referred to as an inner assembly, which may be fitted into an outer sheath. A distal sheath 590, according to one embodiment, may comprise a distal portion 592 (shown extended to the tips of the beaks within, but which may be shortened all the way to just distal of shoulder 593) having a first diameter, and a proximal portion 594 having a second diameter. The second diameter may be larger than the first diameter. To accommodate the differences in diameters of the first and second portions 592, 594, a distal sheath may comprise a shoulder 593 comprising a surface that transitions between the distal and proximal portions 592, 594 of differing diameters and against which the distal portion of a second helical element 585 of FIG. 19 may act, in one embodiment. Furthermore, a distal sheath such as shown in this figure extended nearly to the tips of the beaks or only partway along the beak assembly 13 may be configured to core forward along the length of the scoopula of an outer sheath, such as 512 of FIG. 16B, while lying in the trough of the scoopula, which may be useful in measuring that any tissue encountered would not slide away from the scoopula by combining a forward cutting and side cutting mechanism as previously discussed herein. The scoopula side cuts as it is rotated about the clock face in sampling or is moved laterally to a new target tissue site, and the beak or beaks forward cut as they core within the trough of the scoopula. Furthermore, as the beaks act against the sides of the scoopula, there exists a scissors action between the edge of the scoopula and the beak or beak edges combine forward and side cutting by combined application of their individual cutting surfaces.

According to embodiments, not only a distal sheath, but a proximal sheath and any outer sheaths as well may have shoulders similar to shoulder element 593 of FIG. 20. Such first and second diameter portions of each of these sheaths may be incorporated to accommodate each other in configuration, but also to establish a further expanded expansion chamber portion of a proximal sheath 584 proximal to its attachment to a monolithic beak assembly 13. Such an expansion chamber, which may be even greater than the inner diameter expansion that is simply due to a proximal sheath's greater inside diameter than that of a monolithic beak assembly 13, may similarly serve to allow tissue sample expansion once clear of the coring and severing beak(s), which may further aid tissue transport, with or without a first helical element, and in the presence of active or passive flush fluids and/or aspiration as primary or secondary transport aids. Such an expansion chamber may reduce inner wall friction between the tissue sample and the inner lumen of the device 10, as well as providing space for flush fluids, either passive or active in motion, as will be shown in a further illustration below, to aid tissue transport to a transfer magazine 27 of the device, as shown in FIG. 1.

FIG. 21 is a view of a two-beak assembly with both a distal sheath 590 and the outer sheath 512 removed, according to embodiments. FIG. 21 shows components of the work element 13 (comprising, e.g., a body portion 428, one of a tendon actuation elements 469 and a first and second articulable beaks 602, 604) mechanically coupled to a proximal sheath 584. To show interior structures, a distal sheath 590 is omitted in this view. As suggested at 586, 588 and at 587, 589, a proximal sheath 584 may be spot-welded to the work element 13 in such a manner as to enable differential motion of a body portion 428 of the work element 13 relative to tendon actuating elements 469 thereof when a second helical element 585 compresses and extends, which differential motion actuates (e.g., opens and closes) a first and second articulable beaks 602, 604. Significantly, the attachment of a proximal sheath 584 to both a body portion 428 and to a tendon actuating elements 469 of the work element 13 results in substantially equal torque being imposed on the constituent elements of the work element, thereby maintaining the structural integrity of the work element as it is spun up to speed (by rotating a proximal sheath 584 in this embodiment) and as a first and second articulable beaks 602, 604 cut through variably dense, fibrous and vascularized tissues.

Figure 22:
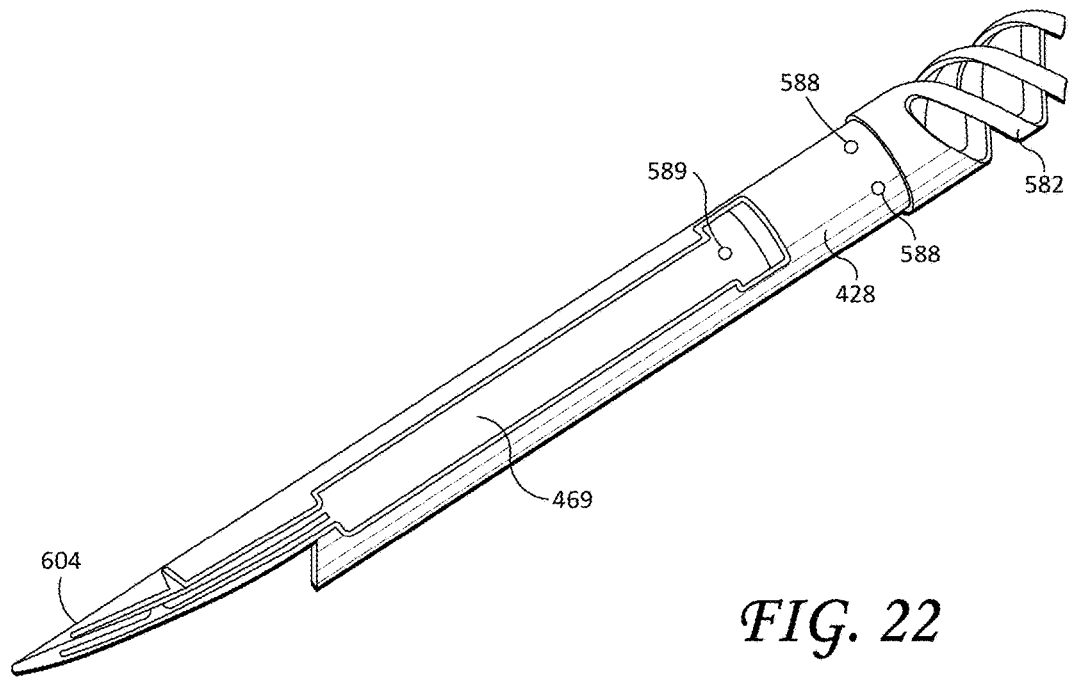
FIG. 22 is a view of a single beak work assembly of an excisional device with the outer sheath, distal sheath and proximal sheath removed, according to one embodiment.

FIG. 22 is a view of a configuration of a short monolithic (to distinguish over the split tube long monolithic single beak configuration of FIG. 15C, for example) single-beak 604 assembly, according to embodiments. FIG. 22 shows a body portion 428, a tendon actuation element 469 and a first articulable beak 604 of the work element 13 together with a first helical element 582. A proximal sheath 584, a distal sheath 590 and an outer sheath 512 are not visible in this view. As shown, a first helical element may be co-axially disposed relative to a body portion 428 of the work element 13 and may be of the same or substantially the same diameter. As noted above, the two may be formed of or cut from a single piece of material such as, for example, a stainless steel hypo tube. According to another embodiment, a first helical member may be of a different diameter than a body portion 428. However, such an embodiment may require corresponding changes to the diameters of a proximal sheath 584 and the proximal portion 594 of a distal sheath 590 and a change to a shoulder 593, if present. In one embodiment, such a single beak 604 may act against the side and forward edges of an outer sheath 512 (not shown in this figure) as illustrated by FIGS. 2-15, according to embodiments. For example, a single beak 604 may act against a scoopula-shaped distal end portion of an outer sheath as previously described.

Based upon the principles of distal work element (beaks) operations from the previous descriptions associated with FIGS. 16-22, it may be seen that, according to embodiments, a totaling proximal sheath 584 may serve to both rotate a single or multiple beaks as well as provide the mechanism for opening and closing a beak or beaks by being itself moved axially distally such that its distal end pushes up against a non- or differentially or same speed rotating distal sheath 590, or a rotating proximal sheath 584 may serve to rotate a single or multiple beaks of the work element 13 being attached to a proximal portion of a monolithic work element while an identically rotating distal sheath 590 may be attached to a beak tendon actuation elements 469, whereby the relative axial movement of proximal and distal sheaths allows for beak actuation. These structures may be further enclosed by a non- or different sally rotating or rotatable and removable outer sheath 512 that may terminate, according to one embodiment, in a trough or scoopula shape, all of which for this device 10 are referred to as the tubular coring and transport assembly 11 in FIG. 1. In the inner lumen of this coring and transport assembly 11, a first helical element 582 may be provided to transport cored and severed specimen in the proximal direction, which may be further aided or replaced by liquid flush induced into the central lumen at the distal end or along the length of the assembly 11 and/or a vacuum aspiration introduced at the proximal end of device 10. If provided, a first helical element 582 may rotate at a different speed than that of a proximal sheath 584 and the beak element(s) 13. With these principles in mind, the following set of figures addresses the mechanical means of providing such actions to the distal end of device 10 of FIG. 1, according to embodiments. It may also be seen that the mechanical arrangements described herein are not the only arrangements that may accomplish some or all of these desired actions on the tubular coring and transport assembly 11, and other arrangements that may be envisioned by a person skilled in the art are considered within the scope of this invention.

Figure 23:
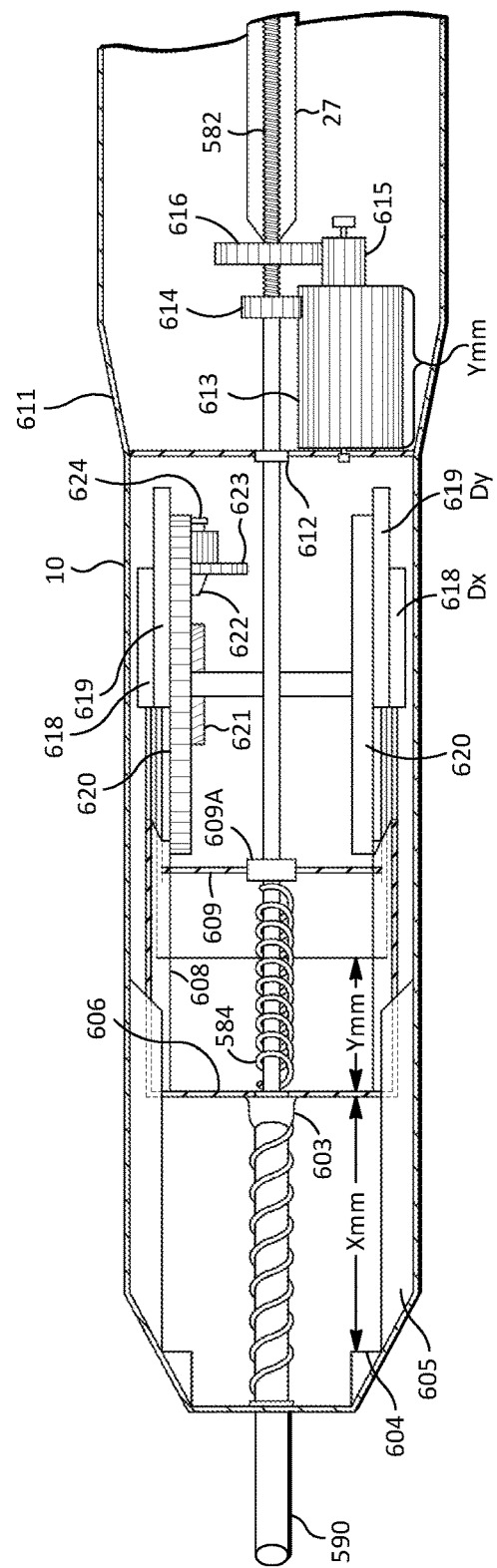
FIG. 23 shows a top view of a mechanical arrangement for cutting element rotation and actuation, according to one embodiment.
Figures 26A, 26B:
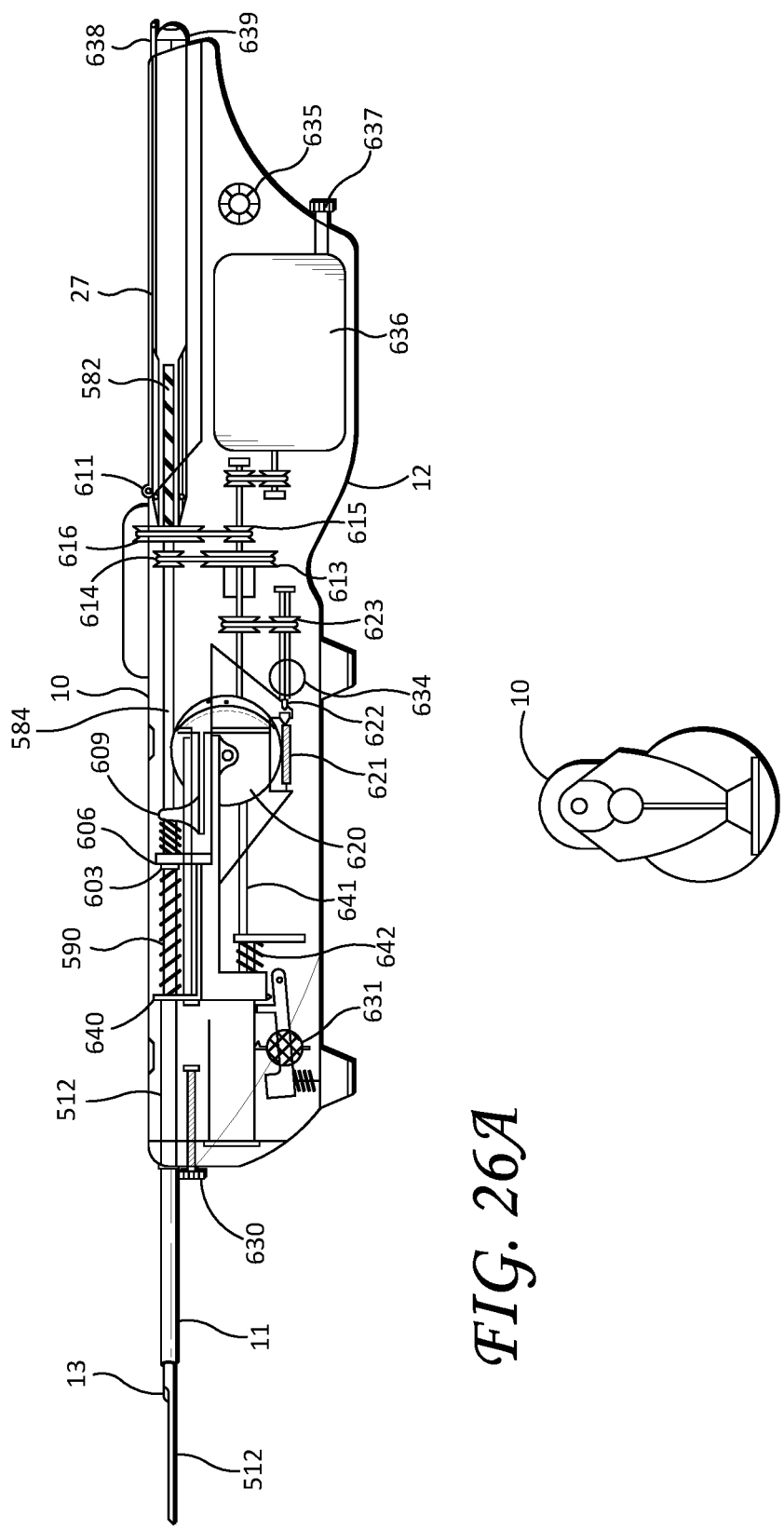
FIG. 26A is a side view of the internal and external features of a biopsy device according to one embodiment.
FIG. 26B is a front end-on view of the shape of a biopsy device, according to one embodiment.

FIG. 23 shows a top view of a mechanical arrangement for tubular coring and transport assembly 11 rotation and actuation, according to one embodiment. In this view, an outer sheath 512 is not shown for ease of illustration, but is shown in FIG. 26A, which illustrates the entire device 10, according to one embodiment. From the left or distal side, a proximal end of a distal sheath 590 passes through a front seal, which in this view is at the distal end of a housing of device 10. A distal sheath 590 is free to move against an internal spring, axially forward and back. According to one embodiment, the total distance of such movement may be about equal to a maximum sample tissue length (not to scale, all relative distances such as Xmm, Ymm and corresponding Dx and Dy (D for distance) are shown for illustrative purposes only). At its proximal end, a distal sheath 590 may be embedded into a tube socket/seal 603, which is itself coupled to the forward wall of a distal sheath carrier 606, which may be configured to slide back and forth within a slide 605 a maximum distance defined by a carrier stop 604, both of which are formed in the outer housing of device 10 in this embodiment. Continuing to the right of the illustration, a proximal sheath 584, contained within a distal sheath 590 and rotating independently thereof, in this embodiment, may be seen passing through a thrust bearing 609A in the forward wall of a proximal sheath carrier 609. A proximal sheath carrier 609 may be configured to slide axially inside a distal sheath carrier on slide 608, which is furnished with its own spring to effectively allow a return force to separate the two (distal and proximal) carriers if they are pushed together, which causes a proximal sheath 584 to move backward or forward, respectively, in relation to a distal sheath 590. Recalling that it is the differential axial movement between a distal sheath 590 and a proximal sheath 584 that activates beak opening and closing, it may be seen that in such embodiment, such axial movement may be accomplished by the action of the two carriers in relation to one another. The total distance travelled by a proximal sheath carrier 609 therefore relates to the axial distance travelled between proximal and distal sheaths to open or close the beak or beaks 13 at the distal end of device 10 according to embodiments.

A proximal sheath 584 is also free to move axially in the distal and proximal directions, under rotation as a result of a thrust bearing 609A described above. A proximal sheath 584 continues proximally in this illustration through a vacuum seal 612 at forward bulkhead of vacuum chamber 611, which serves to capture any stray fluids that may not have been aspirated through the central lumen of the whole tubular coring and transport assembly 11 and through a transfer magazine 27. Rotational force for a proximal sheath 584 is provided by its gear 614 (which may, according to embodiments, be extended to also rotate a distal sheath 590 at the same speed if they rotate together as described in FIG. 22 above), in this illustration, which is driven by a proximal sheath pinion gear 613. A first helical element 582 may also be seen in this figure, which first helical element 582, if present, may be driven at a different rotational speed than that of a proximal sheath by its own gear 616 and pinion gear 615, which may also drive a flush pump or vacuum system of the device (not shown). If such is provided, a first helical element may terminate within a transfer magazine 27 in which tissue samples may be deposited serially.

FIG. 23 also shows that, according to one embodiment, distal and proximal sheath carriers may terminate proximally by vertical side walls of any shape, and upon which a rotating dual cam gear 620, with individual cams such as a distal sheath cam 618 and a proximal sheath cam 619, act upon the vertical side walls of the two carriers. The inner side walls and cam 619 correspond to the proximal sheath carrier 609 and the outer side walls and cam 618 correspond to the distal sheath carrier 606. It may be envisioned, depending on the side profile of each cam, as well as the side profiles of the two vertical side walls, that many different fine-tuned configurations may actuate the same or differential movement, acceleration and timing of differential movement of the two carriers relative to each other, and thus to the combined and coordinated action of the distal work element of device 10, according to embodiments. For instance, the beginning of the rotation of twin gear cams 620 with their individual cams 618 and 619 may actuate the carriers equally, corresponding to distal-directed movement of distal and proximal sheaths, thus coring tissue with the beaks open and rotating. Upon reaching a certain axial distance, a cam 619 may continue forward, closing the beaks and keeping them closed while both distal and proximal sheaths retreat proximally carrying the tissue sample backwards and delivering it to a transport mechanism for eventual delivery to a transfer magazine 27. In such an embodiment, gentle traction would be applied to the tissue sample taken at the end of the part off stage of the biopsy device 10's action for that sample, finite ensuring a positive part-off from surrounding tissue. Many different cam/cam follower (vertical rear walls of the carriers) configuration or shapes may be envisioned to provide forward and backward axial movement combined with differential acceleration of the individual sheaths to allow the device 10 to accomplish its desired operations at different pre-, intra-, and post-operative stages of penetration, coring, part-off, retrieval and storage of sequential samples, as well as material collection from or delivery to the target site as described previously. For instance, a simple in the center vertical section of a vertical rear wall of an inner carrier would result in a double closing of the beaks after a short time interval, which may result in further aiding positive part off of the tissue sample. The vertical walls of each carrier may be asymmetrical to each other or in their upper or lower sections, depending on the mechanical effect desired. The cams themselves may be asymmetrical in their individual side shapes which, combined with special shapes imparted to the vertical rear walls of the carriers, may enable or result in extremely fine tuning of the carrier axial movements at any desired point in time, defined by the revolutionary speed and instantaneous radial angle during revolution of twin cam gears at any time. The twin cam gears of this embodiment may be powered by a worm gear 621, which may allow for movement of the two carriers to be frozen in position at any desired stage. The worm gear 621 may itself be driven by a pinion gear 623 movable on its pilot shaft 624 operating through a simple clutch mechanism 622. It should also be noted that at any time, carrier 609 and carrier 606 may be manually squeezed together through a simple mechanical linkage (not shown), which may cause the beaks to close and part off or remain closed at an operator's choice. It should also be noted that rotation and axial movement are independent of one another with such an arrangement, and thus may be controlled with different actuation mechanisms to allow the device 10 to accomplish all of its intended functions. Again, this illustration is only one of many different mechanical arrangements that may be envisioned by one of skill in the art, all of which are considered to be within the scope of this disclosure, and that may be selected to enable the device to accomplish any or all of the following actions considered characteristic of device 10, according to embodiment:

Penetration to the target tissue site or withdrawal from the site:
  Beak(s) closed and withdrawn, no rotation, scoopula in pre-firing or extended mode;
  Beak(s) closed and extended, no rotation, scoopula in pre-firing or extended mode;
  Beak(s) closed and withdrawn, with rotation, scoopula in pre-firing or extended mode;
  Beak(s) closed and extended, with rotation, scoopula to pre-firing or extended mode;
  Beak(s) open, either withdrawn or extended, no rotation, scoopula in pre-firing or extended mode;
  Beak(s) open, either withdrawn or extended, with rotation, scoopula in pre-firing or extended mode;
  Semi-automatic tissue sampling (gear cams stop after one rotation);
  Automatic tissue sampling (gear cams continue to rotate until interrupted);
  Short core sampling (using the manual part off function described above); and
  Continuous core sampling of any sample length, terminating in manual part off.

Figure 24:
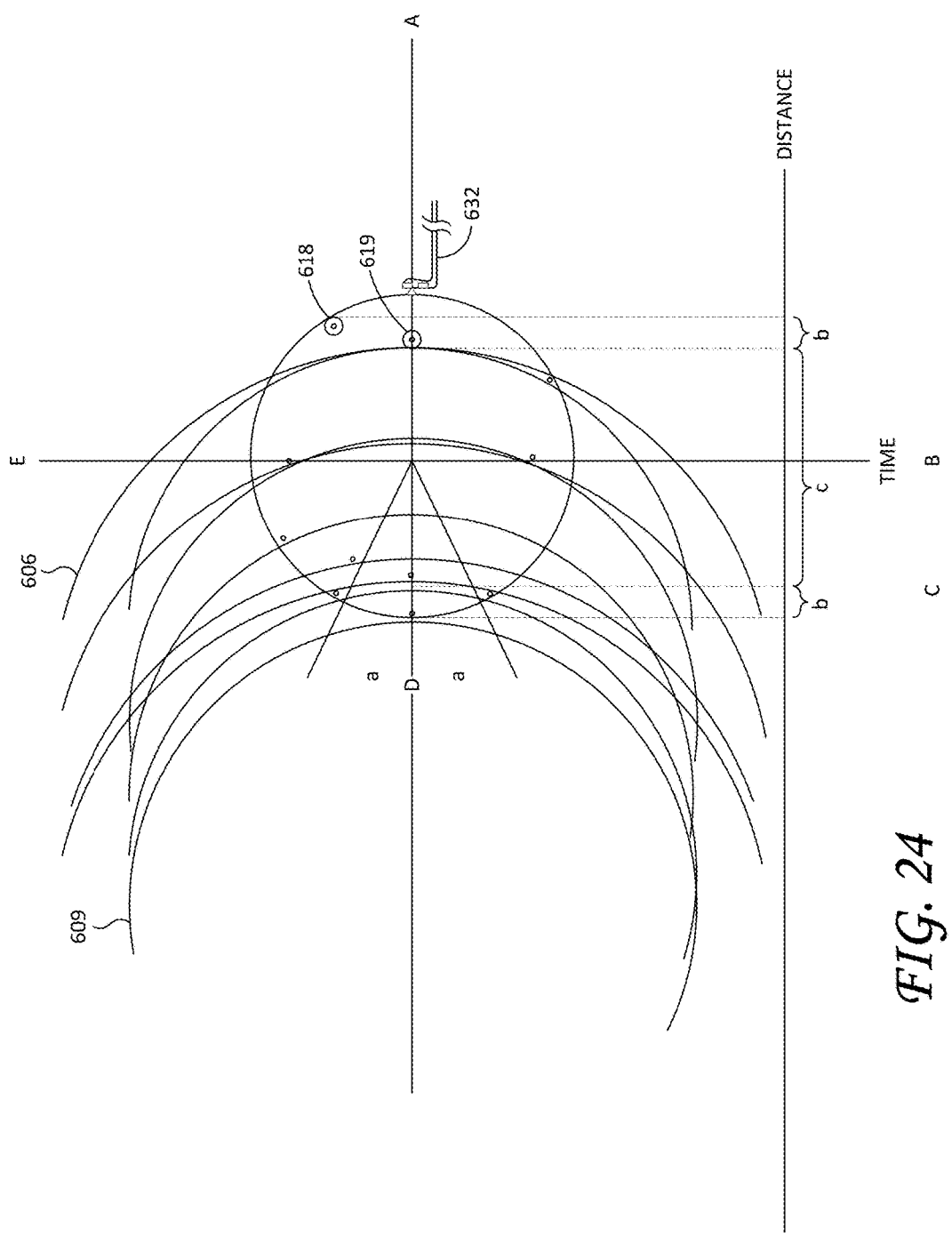
FIG. 24 is an illustration of a cam and cam follower arrangement, according to one embodiment.

FIG. 24 is an illustration of principles of a different arrangement of a cam gear and cam follower arrangement, according to embodiments. This figure specifically looks at the time-based action of geared cam 620 (shown as the central circle in this figure) but configured with two pins surrounded by bushings that act in a similar manner to cams 618 and 619 from FIG. 23, and are thus labeled as such in this figure. In this embodiment, the geared cam wheel 620 is assumed to rotate in a clockwise direction, with pin 618 (analogous in function to cam 618 of FIG. 23) being a short pin that acts only on the inside proximal sheath carrier's vertical rear wall, and pin 619 (analogous in function to cam 619 of FIG. 23), which is a longer pin that is capable at times of effectively acting on both the proximal sheath carrier 609 and the distal sheath carrier 606 vertical rear walls simultaneously. The arc distance between the two pins on the inner surface of the gear cam wheel shown by the two angles "a", using the analogy from FIG. 23, determines which of the two pins is acting on which carrier at any given point in time, either together or in a lead-lag relationship depending on the revolutionary position in time of the gear wheel as it rotates. For purposes of illustration, the larger arcs scribed in this figure correspond to the vertical rear wall surface of the distal sheath carrier 606, and the smaller scribed arcs correspond to the vertical rear wall of the proximal sheath carrier 609. The pins 618 and 619 are shown with their bushings only at the start of the cycle, for purposes of illustration, and are shown as dots at various other locations which correspond to their movement at various time intervals with gear cam wheel 620. The gear cam wheel 620 is shown to the right of the figure, with the arcs of the carriers extending to the left to correspond with the independent carrier movement outlined in the previous FIG. 23. It can be seen that the longer pin 619 is a shorter radial distance from the center of the gear cam wheel 620 than the short pin 618, which pin 618 acts only on the proximal sheath carrier 609. The short pin 618 is also lagging the long pin 619 in revolutionary time, which implies that it comes into play only at a certain point in the clockwise movement of the gear cam wheel 620. Recalling that if the proximal sheath is pressed farther distally than the distal sheath carrier at any time (even manually by the operator) with such an embodiment, the beak(s) will tend to close, following the principles outlined in previous figures, that at a certain point in time (at approximately the 8 o'clock position in this figure) the short pin will begin to act independently on the proximal sheath carrier and extend it differentially farther distally than the distal sheath carrier, closing the beak(s) and keeping them closed until that point in time (at approximately the 2 o'clock position in this illustration) when the beak(s) will again open in anticipation of another forward excursion of both proximal and distal sheaths for coring and sampling.

For purposes of illustration, it is assumed that the rest position of the two carriers is when the long pin 619 is in the 3 o'clock position (beak(s) are open (labeled as "A" or zero time in terms of rotation time), both distil and proximal sheath are at their closest proximal point to the housing of biopsy device 10). The figure includes a small microswitch 632 with a pointer on the gear wheel whose function could be to stop/restart gear wheel 620 revolution when the long pin 619 is in its starting 3 o'clock position, which action may correspond to the difference between semi-automatic (one revolution and microswitch stops revolution until re-enabled) and fully automatic (microswitch disabled altogether and thus rotation and sampling continues until operator interruption of the process) sampling action of the device 10, according to embodiments. The total excursion time of the distal end of the device 10 (coring forward, part off, sample retrieval and transfer to the transport mechanism, return to starting position) occurs in a single revolution of the gear cam 620, and the individual actions of the pins on the individual sheath carriers 606 and 609 are as described herein. Such total sample (excursion) time may vary from as little as about 2 seconds to as long as about 12 seconds, depending on embodiments, with a nominally designated time of 4 seconds, in one embodiment. If the total time for rotation is assumed to be about 4 seconds, then rotational position "A" corresponds to zero, position "B" corresponds to one second elapsed time, position "C" to that interval when the short pin takes over and the beak(s) begin to close, position "D" to two seconds elapsed time (and wherein the beak(s) have closed completely as the short pin 618 reaches that position), position E to three seconds elapsed time and the return to position A corresponds to four seconds total rotation time, assuming constant speed of gear cam wheel 620, which may also be variable, according to embodiments. With the long pin at the 3 o'clock position, it is acting on the vertical rear wall edges of both carriers simultaneously, which continues to be the case until the long pin 619 has reached approximately the 9 o'clock position, at which time the short pin 618, lagging behind at a calculated arc distance a and further radially than the long pin, will start to engage only the inner proximal sheath carrier vertical rear wall, continuing its forward travers at the moment when the distal sheath carrier has ceased its maximum forward or distal movement.

The result is that the beak(s) will close, and remain closed until the long pin reaches approximately the 1 o'clock position, thus withdrawing the sample under either continuing proximal sheath rotation or not, as desired and according to embodiments (since rotation action of the proximal sheath, which rotates the beak(s) and forward/rearward excursion of the carriers are independent of one another, as illustrated in FIG. 23). As the long pin 619 reaches the 3 o'clock position, the beak(s) are fully open and ready for coring forward again and parting off and transferring another sample to the transport mechanism and ultimately to transfer magazine 27. Of note is that according to embodiments, sampling cycle time is a function of the time of one revolution of the gear cam wheel 620, and that the timing for beak actuation is a function of the placement of short pin 618 in relation to long pin 619. The arched (in one embodiment) configuration of the carrier vertical rear walls is only one configuration, but different profile shapes of each vertical rear wall will tend to accelerate or decelerate the actions of the pins on those surfaces, and many different vertical rear wall profile shapes are possible, depending on embodiments. Additionally, the profile shapes of the vertical rear walls of the carriers may differ from top to bottom to impose time-based factors on the action (axial movement, with implied beak actions associated with such excursions of the two carriers, in relation to one another) of each individual carrier 606 or 609, according to embodiments. Finally, in this illustrated embodiment, the axial distance horizontally between the short pin 618 and long pin 619 corresponds to the axial relative distance (and, therefore, time) necessary for travel of the proximal sheath carrier 609 compared to the distal sheath carrier 606 in order to accomplish beak(s) closure (or opening, both shown as "b" in this figure and as shown and discussed in FIGS. 19, 21 and 22 above.) Total excursion distance of the distal end of device 10 is shown as "c" in this figure, and is a function of the placement of pins 618 and 619 and the diameter of the gear cam wheel 620, in one embodiment. Such total excursion distance may be of any length desired, according to embodiments, and for one embodiment, such distance is nominally 1 inch or 2.54 centimeters, corresponding to maximum automatic sample length. Again, it should be noted that samples of any length may be obtained by the operator with device 10, as will be discussed further below.

Figure 25:
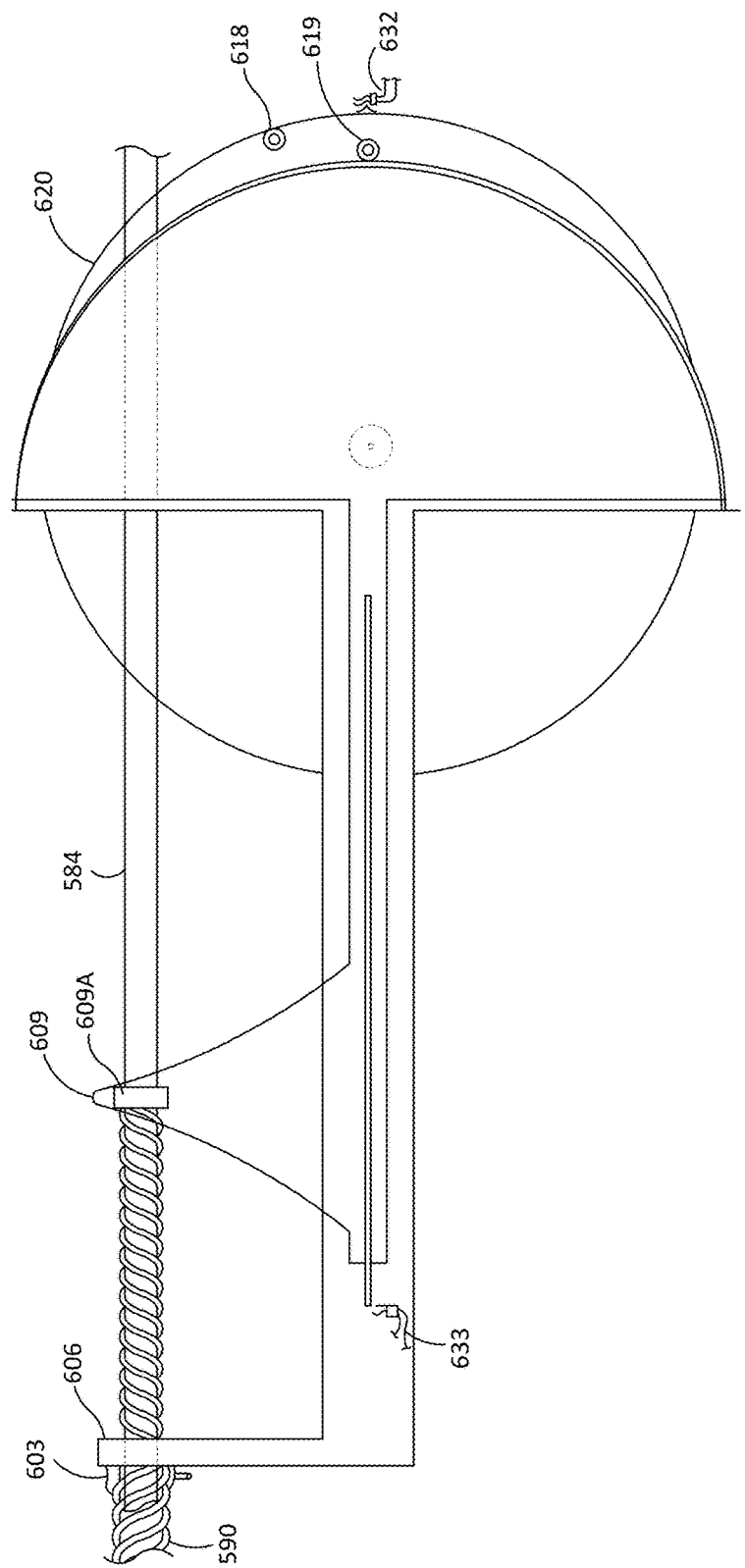
FIG. 25 is a side view of a cutting element actuation mechanism, according to one embodiment.

FIG. 25 is a side view of a cutting element actuation mechanism consisting of twin inner and outer sheath carriers, such as 606 and 609 of FIG. 23, according to embodiments. From the preceding FIGS. 23 and 24, it may be seen that rotation of gear cam wheel 620 will slide both carriers axially distally and proximally, in differential movement to each other, as previously described. Also shown in this figure is the distal sheath 590 with its external return spring, a distal sheath socket and optional flush port 603, the proximal sheath 584, the proximal sheath thrust bearing 609A, the gear cam wheel 620 with its short bushed pin 618 and its long bushed pin 619, the gear cam wheel microswitch 632 and the maximum forward travel proximal sheath carrier microswitch 633. In the embodiment shown in this figure, the vertical rear walls of each carrier 606 and 609 are profile shaped as hemi-circular in form, and of nearly the same size, although other embodiments may alter the shapes of either carrier rear vertical wall to be of any shape desired, which will affect the action of the two carriers' axial movements, according to embodiments and as described under FIG. 24. The rear walls may have special features, such as elliptical shapes in their upper or lower halves, dimples, wavy shapes or any other shape desired, and one skilled in the art will recognize that such profile features will act with the pins of the gear cam wheel to accelerate or decelerate the individual axial movements of the two carriers in relation to each other, all such designs and corresponding movements of which are considered to be within the scope of this invention. Further, the profile shape of each of the two carriers may differ from each other, and the rear walls may be lowered in relation to the long horizontal axis of each of the carriers, resulting in a cantilevered action on the carriers as imparted by the gear cam wheel 620. This may be especially important for embodiments of device 10 specifically designed for stereotactic table use, where keeping the coring and transport assembly 11 of FIGS. 1 and 26 as near as possible to the upper end of the device as possible may be of benefit in allowing a "down the barrel" view of the device in action, as well as for imagining mechanisms where such a benefit has use in being placed as closely as possible to the long axis of the working end (distal end) of the biopsy device, according to embodiments.

FIG. 26A is a side view of internal and external features and elements of a biopsy device 10, and FIG. 26B is a front end-on view of a shape of a biopsy device 10, according to embodiments. In this figure, the mechanism of a distal sheath carrier 606 and a proximal sheath carrier 609 with their elements of FIGS. 23, 24 and 25 are shown in near scale size, according to embodiments, and are themselves carried by and slide axially within drive mechanism carrier 640. An outer sheath 512 may be held to the forward bulkhead of drive mechanism carrier 640 in a manner similar to the way that distal sheath 590 is socketed to distal sheath carrier 606, but is also easily removable from the device 10 by the operator if desired prior to, during or at the end of a procedure, thus being placed or left in situ for the purposes of pre or post-procedure cavity (target tissue site) access for such purposes as the introduction of markers, medication or filler materials as well as drainage or as an introducer for additional devices. If it is placed pre-procedurally, it may be placed over a locating wire and serve itself as a locating tube for device 10 or other devices. It may also have external features to support an extendable locating wire or other structure designed to improve visibility of the tip of the device, immobilize a target tissue or measure its extent, among other functions. An outer sheath 512 may be easily coupled to a handle 12 or housing of device 10 by a Luer lock system, for instance and in one embodiment, which would allow for easy assembly and dis-assembly, as well as for the connection of additional devices for fluid or solid delivery systems, drainage systems and other devices. Other elements also shown in various previous figures herein include a tubular coring and transport assembly 11, a non- or differentially rotating or rotatable outer sheath 512, a work element with its beak(s) 13, a distal sheath 590, a proximal sheath 584, a distal sheath carrier 606, a proximal sheath carrier 609, a proximal sheath thrust bearing 609A, a distal sheath socket/flush port 603, a proximal sheath pulley 614 (analogous to gear 614 of FIG. 23), a first helical element pulley 616, a vacuum chamber 611, a first helical element or transport helix 582, if present according to embodiments, a transfer magazine 27, a flush port 638, an aspiration/material delivery port 639, a power switch/indicator 635, a DC adapter port 637, a DC motor 636, a transport helix pinion pulley 615, a proximal sheath pinion pulley and clutch mechanism (magnetic or otherwise) 613, a worm gear clutch pinion pulley 623, a worm gear clutch 622, a worm gear clutch (gear cam wheel clutch) button 634, a worm gear pinion 624, a gear cam wheel 620, a drive mechanism carrier common driveline 641, a return spring 642, a forward firing mechanism trigger and lever 631, and a depth stop adjustment mechanism 630. It should be noted that, according to embodiments, many other substitutions for any or all of the elements noted herein that accomplish the same function or fractions may be devised by one skilled in the art, and all such substitutions are considered within the scope of this disclosure. The drive mechanism carrier may be used to slide nearly all of the internal drive components illustrated in this figure forward against a stop at the distal end of the handle 12 of device 10, which may correspond to an internal forward firing mechanism for placement of an outer sheath and scoopula portion of an outer sheath 512 in proximity to or through a lesion, as desired by the operator, and at described for such a procedure in FIG. 1 above. Alternatively, only the outer sheath itself may be forward fired without carrying the internal drive mechanism with it, according to embodiments. This outer sheath may be manually, or in other embodiments, automatically rotated to various "o'clock" positions by the operator through a simple manual or driven wheel or ratchet mechanism attached to an outer sheath 512 (not shown). It should be noted that according to embodiments, rotation of a proximal sheath, a first helical element, if present, and a distal sheath (if rotated) are independent of the distal and proximal axial movement of the tubular coring and transport assembly 11, and because of that feature, according to embodiments, the operator may select various functions of the device 10 at any time, as described previously under FIG. 23 above.

FIG. 26B is an end on view of a biopsy device 10, according to one embodiment. Various other end profile shapes are possible, and are considered within the scope of this disclosure. Of particular note with this view and this embodiment, the device 10's tubular coring and transport assembly 11 is located near the very top of the device, which may thus allow a better viewpoint for both the operator and the imaging devices used with device 10.

Figure 26C:
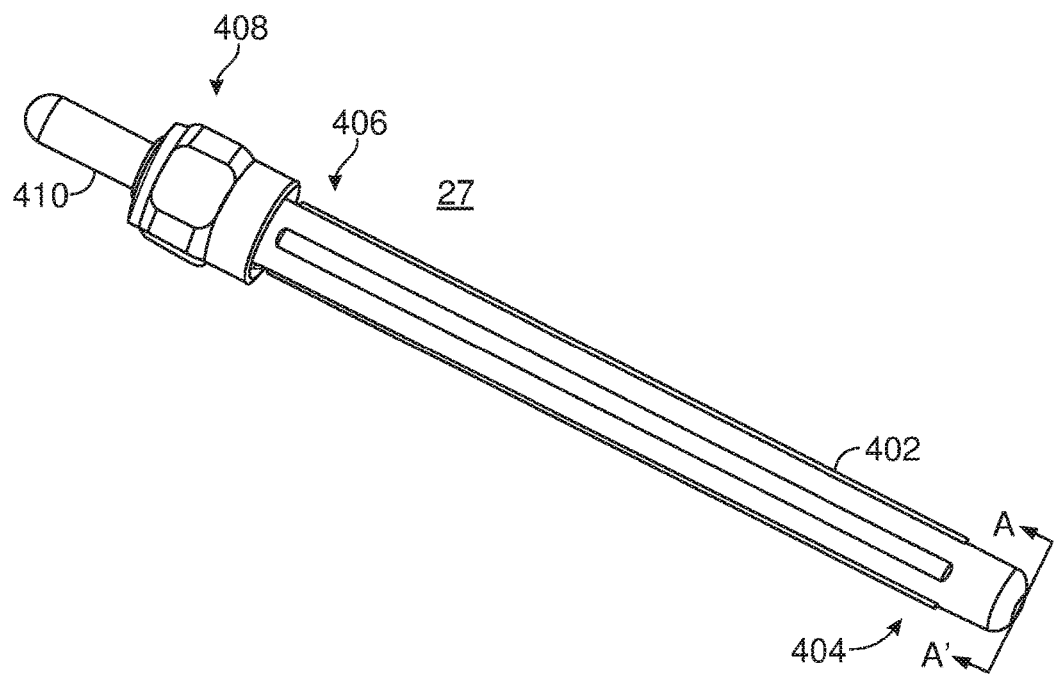
FIG. 26C is a perspective view of a transfer magazine, according to one embodiment.
Figure 26D:
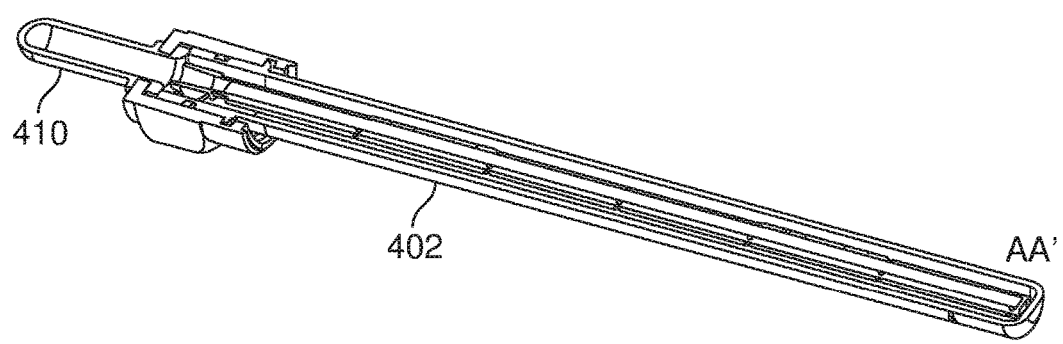
FIG. 26D is a cross sectional view of a transfer magazine according to one embodiment, taken along line AA' of FIG. 26C.
Figure 26E:
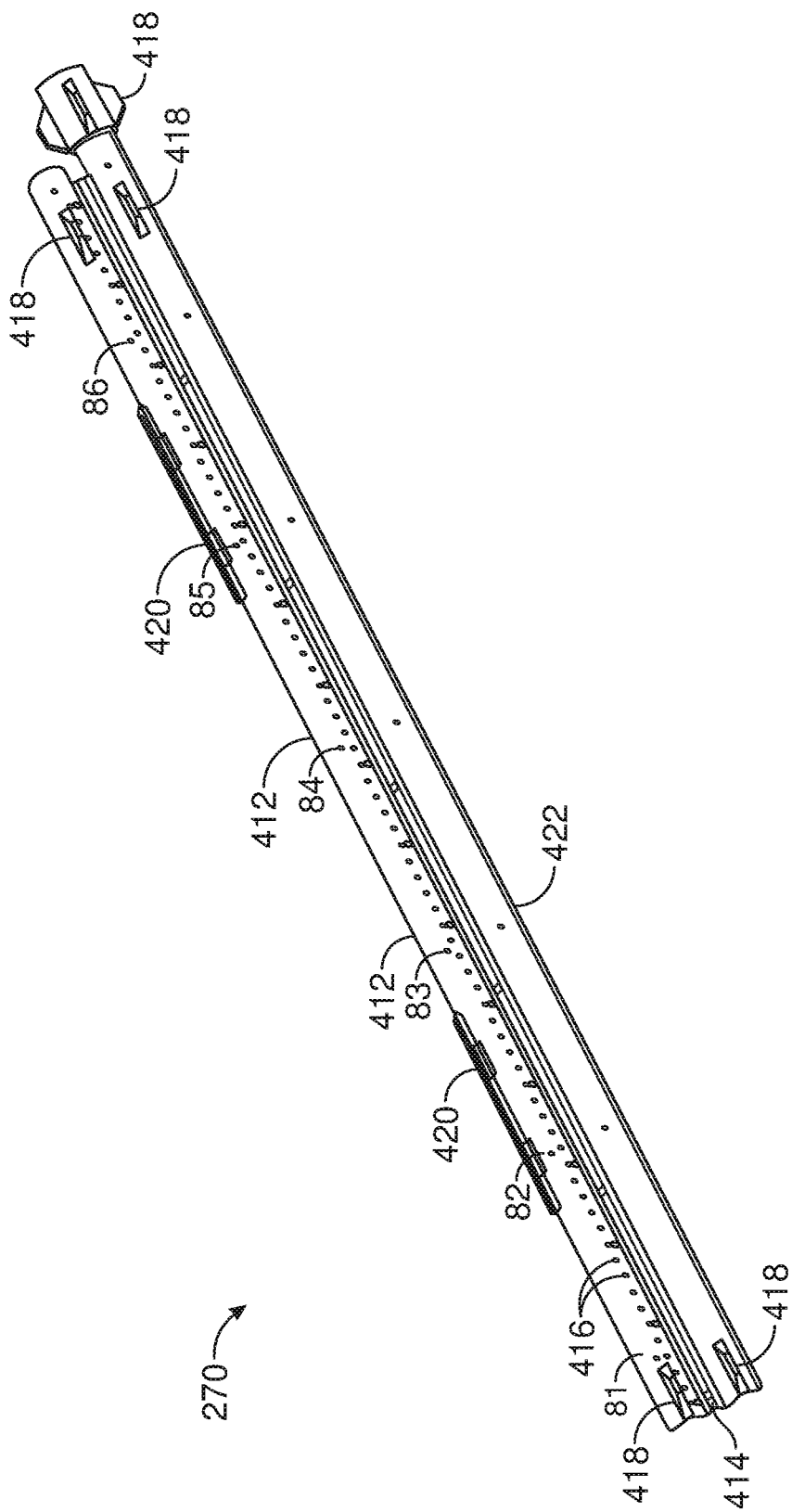
FIG. 26E is a perspective view of a hinged, clamshell embodiment of a transfer magazine, according to one embodiment.

FIG. 26C shows a transfer magazine 27, according to one embodiment. FIG. 26D is a cross-sectional view of a transfer magazine 27 of FIG. 26C, taken along cross-sectional line AA', and FIG. 26E shows a view of an internal collection tube that may be split open as shown therein. Considering now FIGS. 26C, 26D and 26E collectively, a transfer magazine 27 may contain an internal elongated tube 422 (as shown in FIG. 26E) configured to receive cored and severed tissue specimens. In particular, a transfer magazine 27 may be configured to receive and (e.g., temporarily) store cored tissue specimens or samples, and to preserve the order in which the samples were acquired. Specifically, a transfer magazine 27, according to one embodiment, may be configured to store a serial train of tissue samples, from a first sample at one end of the serial train of samples to the last sample acquired at the opposite end of the serial train of samples. For example, the first sample taken may be urged within an elongated tube 422 to be closest to the distal end of a transfer magazine, wherein proximal and distal qualifiers are defined relative to the biopsy device. As shown in FIG. 26A, the distal end 406 of a transfer magazine 27 is closest to the beak assembly 13 and the proximal end 404 of a transfer magazine 27 may form one of the proximal-most structures of the present biopsy device.

A transfer magazine 27 may address various clinical needs by enabling the operator of the present biopsy device to inspect the core samples more closely, and in some cases tactilely, without destroying the record-keeping function of transfer magazine 27. A transfer magazine 27 is referred to as such, as the storage of the cored and severed tissue samples may be short term. Since transfer magazines 27, according to embodiments, may be configured to be removable and/or replaceable at any time(s) during the procedure, the present biopsy device enables a variety of procedural methods to be carried out, which methods would not be possible, or at least would be impractical without the structures disclosed herein. For example, using the present biopsy device, a clinician may segregate the contents of one transfer magazine 27 from the contents of another, additional transfer magazine 27. The operator of the present biopsy device may also have the ability to interrupt coring/transport/ storage with another function of biopsy device, all the while, at the operator's discretion, keeping the present biopsy device's tubular coring and transport assembly 11 in place, or alternatively elements of such assembly 11, such as a removable outer sheath 512, thus minimizing trauma associated with repeated removal and insertion of the present biopsy device.

According to embodiments, a transfer magazine 27 may comprise a single or multiple piece assembly which may include a tube or tubes 422 extending forward inside the device all the way distally to monolithic beak assembly 13, in place of a first helical element 582, or alternatively may extend only to the proximal end of either a proximal sheath 584 as shown in FIG. 26A or to the proximal end of a split tube long monolithic beak assembly such as shown in FIG. 15B, and may also contain slots arranged to allow for flush systems to direct fluids in such a manner as to aid transport of the tissue specimen and also collect body fluids for subsequent analysis. In such embodiments, flush fluids and aspiration by vacuum would enable continuous transport of specimens from the distal end of the device to the main body of a transfer magazine 27, and a transfer magazine 27 may either be separated from its distal transport tube, if present, according to embodiments, or removed from the device with its integral transport tube. Such a system would maintain vacuum integrity within such simple mechanisms from the distal end of the device to its most proximal end.

An elongated tube 422, according to one embodiment, may also comprise a central track or inner transfer magazine track, such as shown in FIG. 26E below, configured to receive the serial tissue specimen, and, according to embodiments, may be fitted with Luer-lock type fitting for easy attachment to the device. Vacuum may be provided via an axial vacuum port, for instance in the expanded region of FIG. 26C at the distal end of the magazine, which may allow for only one vacuum connection to be required by the device, according to embodiments. At regular intervals (on the order of the length of tissue samples acquired by the excisional device, for example) along the length of an inner transfer magazine track, the present transfer magazine 27 may define vacuum holes through which a vacuum may be drawn between the outer tube 402 and the inner tube 422, which receives the samples in serial order. According to embodiments, these vacuum holes may be lined with a filter element, such as sterile filter paper or other filter media, to catch and filter cells and other materials from any fluids that accompany a tissue sample to the transfer magazine. This vacuum, optionally along with flush, may urge the cored and severed tissue specimen in the proximal direction, towards the proximal end 404 of a transfer magazine 27. Having reached the proximal end of the interior track, the cored and severed tissue specimen may come to rest and may, according to one embodiment, block or occlude one or more vacuum holes disposed along the length of an elongated inner tube 422. In this manner, no further vacuum will be drawn through such blocked vacuum hole(s). This blocked vacuum hole or holes, however, keeps the just-obtained tissue specimen in place (at the proximal-most available slot along the interior track of the magazine 27) while allowing more distally-disposed vacuum holes to continue to draw the vacuum therethrough and to continue to urge later-obtained samples to the next-distal position within the magazine. According to one embodiment, when the last vacuum hole disposed along the length of the elongated tube 422 has bee blocked by an obtained sample, a transfer magazine 27 may be considered to be full. A full transfer magazine 27 may then be withdrawn from the biopsy device. A new transfer magazine 27 may then be provided and inserted into the biopsy device to continue the procedure, if desired. Note that a transfer magazine 27 may be withdrawn from and replaced back into, the biopsy device, without interrupting the procedure and without withdrawing the work element 13 from the tissue. Moreover, withdrawing a transfer magazine 27 allows access to the interior lumen of the beak assembly, which in turn allows any number of imagine materials or devices, cosmetic materials or therapeutically-beneficial substances to be delivered, or fluids and/or cells to be evacuated from the target site.

Once a magazine 27 is withdrawn from the biopsy device, a magazine capping and sealing element 408 may be coupled to the distal end of the magazine 27. A capping and sealing element 408 may be configured to seal the collected samples, cells and any fluids collected from the outside, to enable ready transport, imaging, direct visual observation or even tactile manipulation. A capping and sealing element 408 may comprise a fluid release element 410. A fluid release element 410 may comprise, for example, an ampule of fluid surrounded and seated within a soft covering of, for example, rubber or vinyl. The soft covering may be squeezed between the user's fingers to crush the ampule of fluid, which fluid may then be released to permeate the interior of a transfer magazine 27. For example, the fluid released may comprise a preservative configured to preserve the tissue architecture and prevent degradation of the collected tissue samples. Other fluids (e.g., stains) may be added thereto or used in place of the preservative.

According to one embodiment shown in FIG. 26E, a transfer magazine 27 inner track, as described in the previous paragraph, may comprise a clam-shell structure. Indeed, a transfer magazine 27 inner track may comprise a (living, for example) hinge 414 so as to enable the transfer magazine 27 to be opened along its longitudinal axis and its contents directly viewed by the user or pathologist. In such an opened state, a transfer magazine enables any one or all of the samples to be withdrawn from a transfer magazine 27 for close examination and, if desired, replaced therein, without disturbing the sequential order in which the samples were stored. According to embodiments, a transfer magazine 27 may comprise visible markings and/or radio opaque markings 412, to assist the user in determining the order in which the samples were obtained. Such markings may, for example, comprise numbers or identifying features appearing on the elongated tube 422. For example, the number "1" may be visible in the proximal-most position of a sample with a transfer magazine, followed by "2" for the location of the next specimen, and so on. It is then easy to correlate the specimen with the location from which the specimen was taken. For example, if 12 specimens were taken "around the clock", the first specimen will correspond to the 12:00 o'clock position, and the 7$^{th}$ sequentially disposed specimen within a transfer magazine 27 will correspond to the 6:00 o'clock location with the body. Alternatively or additionally, visible markings 412 may consist of metric or imperial ruled markings for ease of sample length measurement, and may also be radio-opaque or embossed with individual transfer magazine numbers to distinguish multiple magazines from each other. Part or all of a transfer magazine 27 may comprise or be formed of transparent material, so as to enable direct visualization by the user of the obtained specimen. A transfer magazine 27, according to embodiments, may be lucent to other imaging modalities, such as MRI, for example. The vacuum holes disposed along the length of the elongated tube 422 are visible in this view at 416. In an embodiment, features may be included within a transfer magazine 27, for example on outer tube 402, that could be configured to magnify and/or illuminate the acquired specimens. Fin-like extensions 418 may be provided, to enable an opened transfer magazine 27 to lie in a stable manner against a flat surface. Such fins may be asymmetric relative to each other to aid in stability of the device when placed upon an unstable or irregular surface. A transfer magazine may be provided with snap or interference fittings 420 to enable a magazine 27 to be manually opened and closed and reopened/reclosed.

According to one embodiment, a tissue biopsy method may comprise performing coring/biopsy/transport cycles as described above. Thereafter, removing a transfer magazine and/or proceeding to marking and/or treatment phases may complete the procedure. A transfer magazine may then be removed and, if desired, placed under X-Ray, magnetic resonance imaging and/or ultrasound transducer or high-resolution digital camera if a transfer magazine is made of a transparent material. The core tissue specimens may then be imaged/recorded. The magazine may then be placed in a delivery receptacle, sealed and delivered to a lab for further analysis, making note of core lengths and correlating with imaging record(s) in-situ and ex-vivo. Upon removal of transfer magazine 27 from the present biopsy device, the collected cores may then be visually inspected through the transparent walls of a magazine. The magazine may then be split open to manually handle and analyze the tissue specimens as desired as well as to collect any fluids or cells for cytologic analysis. The magazine may then be closed again, with the specimen therein.

A transfer magazine 27 may then be replaced with additional empty transfer magazine(s) as needed to complete the biopsy procedure. Alternatively, other cartridges/magazines may be fitted to the present biopsy device to deliver medications, markers and/or tracer elements, therapeutic agents, or therapeutic and/or cosmetic implants to the biopsy site. Still other devices for imaging or therapeutic purposes may also be placed into the device in place of a transfer magazine, as desired and according to embodiments. The procedure may then be terminated or continued, such as would be the case should the practitioner desire to biopsy/core other nearby areas as deemed clinically useful.

As shown, a device 10 with an outer sheath 512 with a scalpel-like distal end may be gently placed in proximity to or through a lesion, or may be forward-fired through the lesion using the internal mechanism of device 10, according to embodiments. Clinically and procedurally, the ability of a biopsy device to advance gently towards a target lesion provides several advantages. Indeed, when a biopsy device does not advance gently toward a target lesion or does not smoothly core through dense target tissue, the operator may be led to exert excessive force onto the biopsy device, thereby potentially forcing the biopsy device into and even through adjacent structures. There have been instances of biopsy device components being broken off, requiring surgical removal thereof from the biopsy site when excessive force was needed in attempts to obtain core samples from tissues such as dense breast tissue. The present method of introducing a sharpened scalpel-like scoopula, with the withdrawn and closed beak(s) configured in a penetration mode according to one embodiment herein and provided for with a specific cycle stage in the biopsy device 10 of FIG. 1, enables an operator to gently and smoothly approach a target lesion without requiring excessive manual axially-directed force to be exerted on the present biopsy device, by the operator or by the stereotactic table itself, if used. It is to be noted that when excessive force must be exerted to advance conventional coring devices through dense tissue, the resultant image provided by guidance modalities may be significantly distorted by the effects of the applied force onto the conventional cording device and transferred to the surrounding tissue, which may cause the resultant image to be less distinct or blurred, which, in turn, makes the biopsy procedure less accurate and much more difficult technically. This excessive force may also damage tissue, resulting in loss of tissue architecture and production of the aforementioned biopsy artifact. It is an important goal of all core biopsy procedures to firmly establish that the core sample is taken from the highly specific image area, notwithstanding the constraints imposed by the small dimensions of the target tissue. Such small dimensions, therefore, require clear views of sharp margins to attain the kind of accuracy desired.

Flush and liquid/solid materials delivery mechanisms may be incorporated into the biopsy device 10, according to embodiments, to aid in tissue specimen transport to the transfer magazine 27. Such mechanisms may consist of the distal tube socket/flush port 603 of FIG. 23, which may deliver flush fluids to the distal end of the device between the distal and proximal sheaths, or similarly with another analogous port between the distal sheath and outer sheath 512, with flush fluids being connected to the device through port 638 of FIG. 26A, for example. Flush fluids and other materials may also be delivered to the tissue site through the central lumen of the device, with beak(s) closed (as described for liquids under FIG. 5 above through the living hinge slots) or open, using the aspiration port 639 shown in FIG. 26A or through a transfer magazine 27 of FIG. 1 above, according to embodiments. Flush fluids may also be delivered to the distal tip through ports in the collar 593 of the distal sheath shown in FIG. 20 above. As previously described, fluids, solids and other materials may be delivered to the tissue site through the central lumen of the device and various slots and mechanisms such as the open beak(s) may be used in conjunction with flush fluids to gather and transport cells and liquids from the tissue site for later cytological analysis.

Figure 27A:
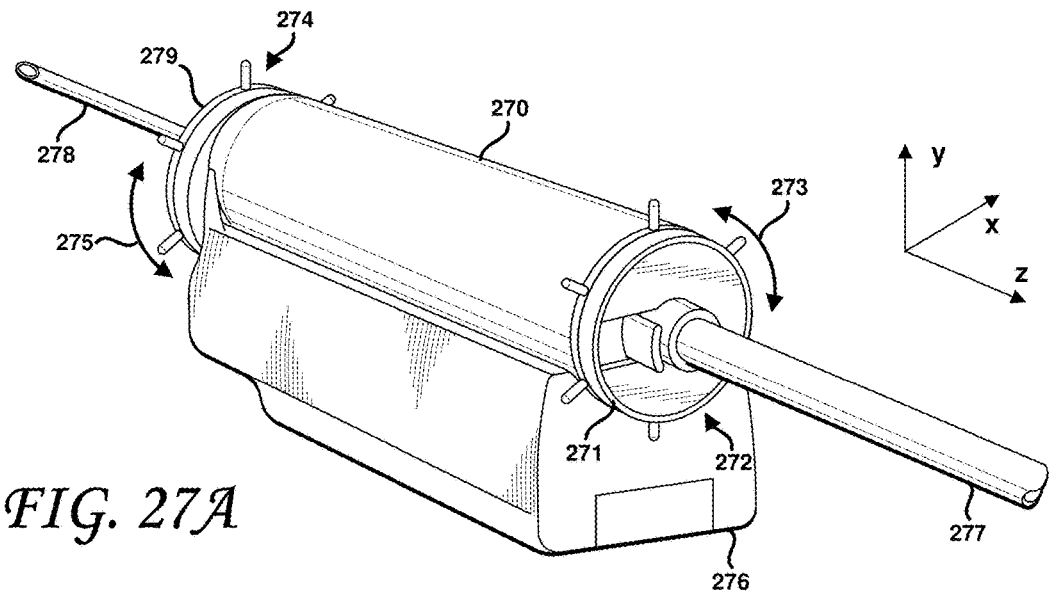
FIG. 27A is a first view of a stereotactic table adapter for a biopsy device, according to one embodiment.
Figure 27B:
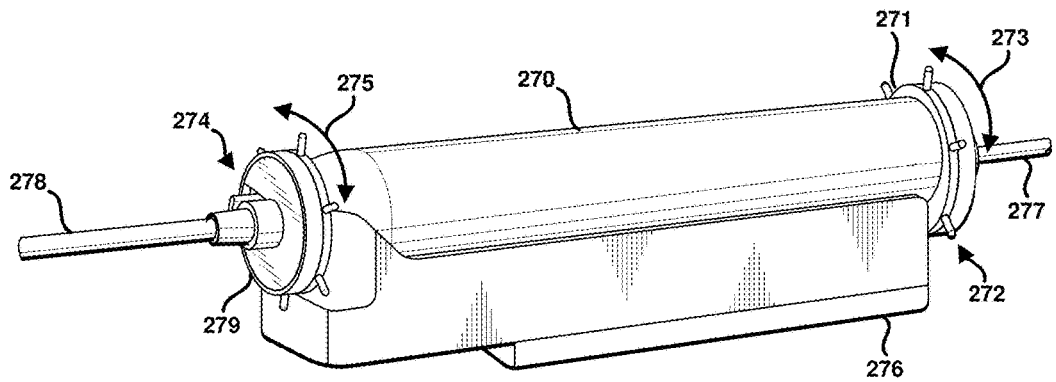
FIG. 27B is a second view of a stereotactic adapter for a biopsy device, according to one embodiment.

FIG. 27A is a first view of a stereotactic table adapter for a biopsy device, according to one embodiment. FIG. 27B is a second view of a stereotactic adapter for a biopsy device, according to one embodiment. In FIGS. 27A and 27B, reference 270 denotes some type of generic interventional device. Reference numeral 278 represents the distal end of the excisional device, whereas numeral 277 represents the proximal end of the generic device 270. For example, 277 may represent a source of vacuum. The distal tip of 278 may be provided, for example, with a monolithic beak assembly, as described and shown herein. The excisional device 270 may rest upon stereotactic platform 276, which may be coupled to the stereotactic table stage. According to one embodiment, an excisional device according to one embodiment or most any excisional device may be coupled to the stereotactic platform 276 through one or more capstan assemblies 272, 274. One of more of the capstan assemblies 272, 274 (or windlass assemblies, by virtue of their horizontal axes), may be provided to enable the user to change the orientation or angle of attack of the excisional device 270 relative to the platform 276 and thus relative to the stereotactic table stage as well. The capstan assemblies 272, 274 may be, according to one embodiment, secured to both the excisional device 270 and to the platform 276. That is, depending upon the orientation of the constituent elements thereof, the capstan assemblies 272, 274 may enable one or both ends of the excisional device 270 to be moved along the x-y plane (e.g., up and/or over a device penetration axis along z). In so doing, the proximal end of the excisional device may be raised and/or moved off-center relative to the platform 276, by manipulating the capstan assembly 272. Similarly, the distal end of the excisional device may be raised and/or moved off-center relative to the platform 276 by manipulating the distal capstan assembly 274. Both the proximal and the distal ends of the excisional device 270 may be raised or moved off center, either in the same or different manners. This enables flexibility and fine-grained control of the orientation of the excisional device 270 independently to the orientation of the stereotactic table stage, or in conjunction with it, as small adjustments in the orientation of the proximal end of the device have a correspondingly larger effect at the distal end (i.e., working end) of the device 270. In turn, this may enable the user to exert great control of the location within the body from which the samples are cored and severed (or ablated, dissected, etc., depending upon the nature of the excisional device 270).

During operation, the user may adjust the orientation of the device 270 by turning an actuator such as ship's wheel 271 of the capstan assembly 272 in either of the directions indicated at 273 and/or by turning ship's wheel 279 of capstan assembly 274 in either of the directions indicated at 275. The capstan assembly 272 may be operated using other forms of actuators. Moreover, such an actuator need not be operated by rotation, as is the ship's wheel 279 shown and described herein, as those of skill in this art may realize. By turning the ship's wheel 279 in this manner, the user may selectively move the proximal end of the device and/or the distal end thereof up and off-center (relative to its initial centered position shown in FIGS. 27A and 27B.

Figure 27C:
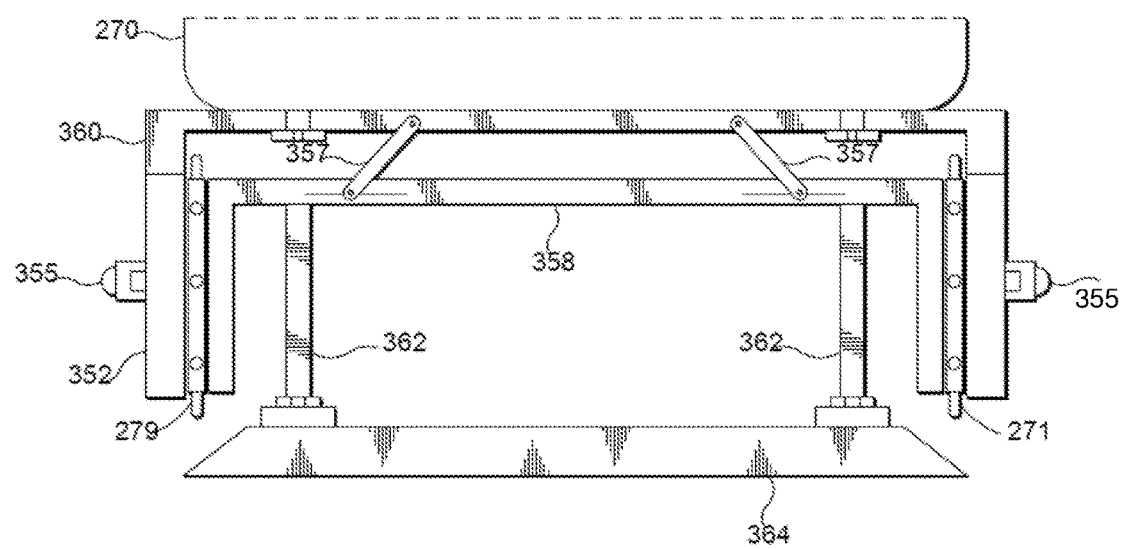
FIG. 27C is a side view of an adapter platform, suitable for a stereotactic table stage, and on which an excisional device may coupled, according to one embodiment.

FIG. 27C is a side cutaway view of a platform, suitable for a stereotactic table stage, on which an excisional device 270 may be coupled according to one embodiment. As shown, the platform, similar in function to element 276 of FIGS. 27A and 27B may comprise an upper adapter plate 360 and a lower adapter plate 358. The lower adapter plate 358 may be coupled, at 362, to the stereotactic table stage 364. The lower adapter plate 358, therefore, may be held immobile with respect to the stereotactic table stage 364. The upper adapter plate 360 may be movably coupled to the fixed lower adapter plate 358 through, for example, two or more pivot arms 357. Therefore, the upper plat 360, to which the excisional device 270 is fixed, may move relative to the lower adapter plate 358. As shown, each end of the upper adapter plate 360 (and thus the excisional device 270) may move somewhat independently of the other end of the upper adapter plate.

As shown in FIG. 27C, each of the upper and lower adapter plates comprise descending extensions with the lower adapter plate 358 comprising the inner descending extensions and the upper adapter plate 360 comprising the outer descending extensions that are generally parallel to the descending extensions of the lower adapter plate 358. According to one embodiment, the capstan assemblies 272, 274 of FIGS. 27A and 27C may be fitted in the space between the descending extensions of the upper adapter plate 360 and the descending extensions of the lower adapter plate 358. According to one embodiment, the capstan assemblies 272, 274 may be fitted over respective central pins of the lower plate 358 such that the ship's wheels 271, 279 are coupled to the descending extensions of the lower adapter plate 358. According to one embodiment, and as is described further relative to FIGS. 28A-D, rotation of the ship wheel 271, 279 thus moves the upper plate 360 (and thus the excisional device coupled thereto) through its full range of motion as the fixed central pin 355 of the lower plate 358 is acted upon by an outer wheel of the capstan assembly 271, 279. In such an embodiment, the ship wheels 271, 279 are placed well below the biopsy device 270, and thus such a system of upper and lower adapter plates may be fitted to and used with any existing stereotactic biopsy device since this embodiment merely fits between and mates to both a biopsy device 270 and a stereotactic table stage 364, as well as with the biopsy device of the present disclosure.

The stereotactic devices commonly encountered today take a series of biopsy samples starting with an initial sample, with subsequent samples being taken by manually rotating the outer sheath of the distal end of such devices in a manner so as to sample "around the clock." The capstan assemblies 272, 274 allow for additional movement of any stereotactic biopsy device in a greater range of motion than is currently available through the use of the stereotactic table stage controls for x, y and z placement of the device. Of note also is that the proximal and distal capstan assemblies 272, 274 may not only be rotated in synchronism with one another but also may be rotated differentially relative to one another, such that angles can be obtained in addition to displacement. Such movements may be accomplished by manual manipulation but may also be directed by software executing within a stereotactic biopsy device controller. The ability to rotate the two capstans 272, 274 independently or in synchronicity enables an interventional radiologist to gain access to otherwise difficult anatomical locations without repositioning the breast, for example. In effect, the addition of one or more capstan assemblies 272, 274 add polar coordinate orientation capability to an otherwise Cartesian-restricted machine, and vice versa.

Figure 28A:
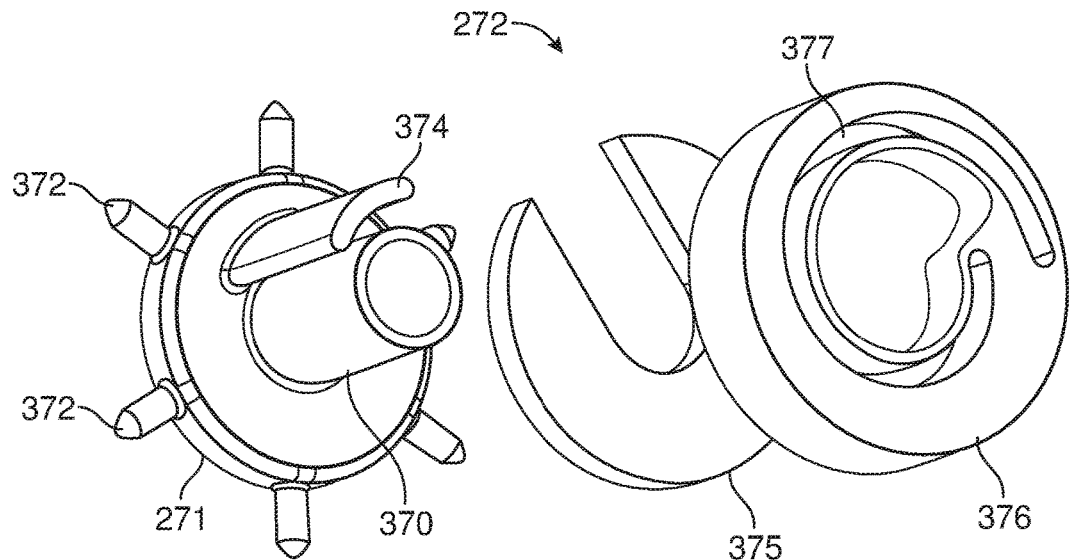
FIG. 28A is a perspective exploded view of a capstan assembly, according to one embodiment.
Figure 28B:
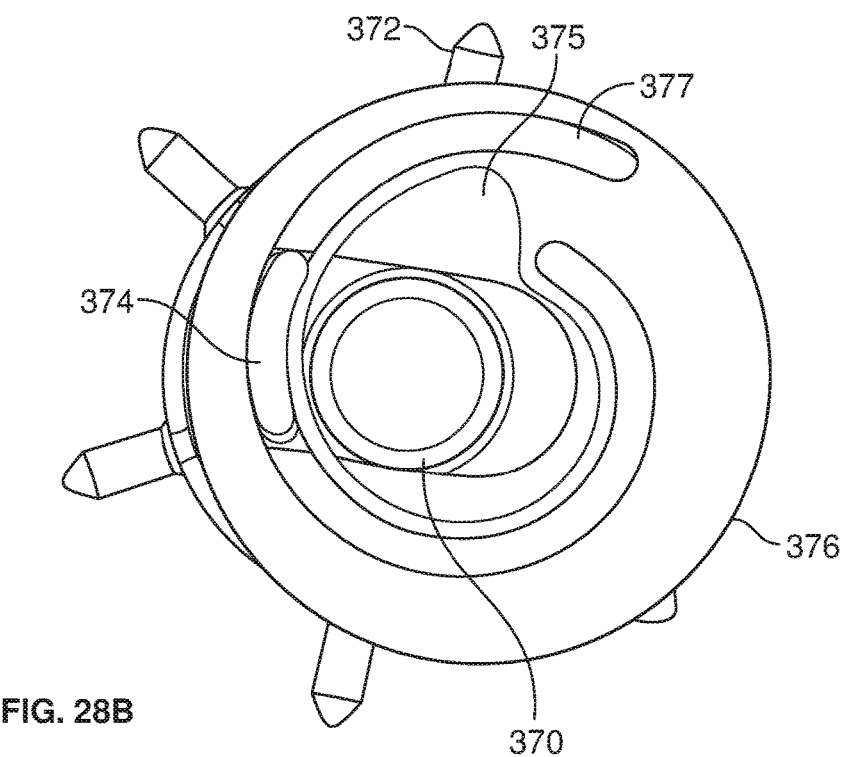
FIG. 28B is a top view of a capstan assembly, according to one embodiment.

FIGS. 28A through 28D show one embodiment of a capstan assembly, such as shown at 272 and 274 in FIGS. 27A-C. As shown in FIG. 28A, a capstan assembly 272 may comprise a ship's wheel 271 fitted with extending prehensile features 372 around the circumference thereof, to enable the user to easily turn the ship's wheel 271 about a central pin of the lower adapter plate 358 of FIG. 27C, for example, which is configured to fit within central well 370, to enable the ship's wheel 271 to rotate thereabout. The ship's wheel 271 may comprise a wheel guide extension 374, disposed between the central well 370 and the outer circumference and substantially parallel to the wheel central well 370. A notched inner washer 375 may fit over the wheel well 370, such that the wheel guide extension 374 fits within the notch of the inner notched wheel 375. A spiral path element 376 may then be disposed over the wheel guide extension 374 such that the wheel guide extension 374 fits within the spiral pathway 377 disposed within the spiral guide element 376, as shown in the top view of FIG. 28B.

Figure 28C:
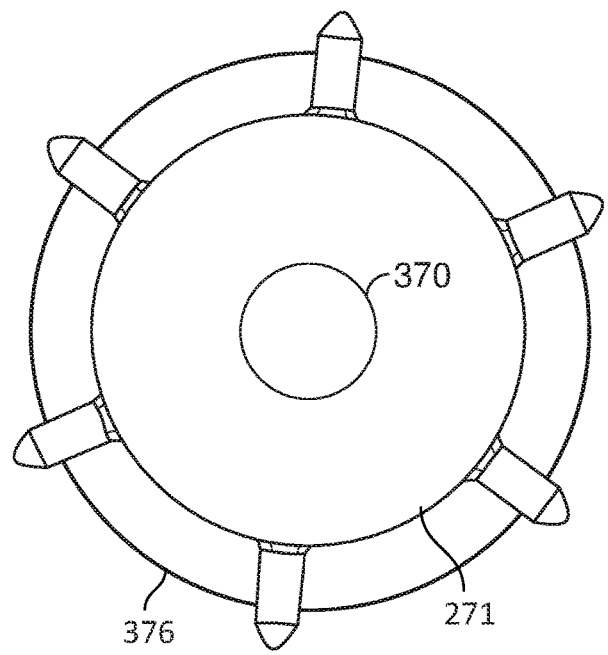
FIG. 28C is a top view of a capstan assembly in a first configuration, according to one embodiment.
Figure 28D:
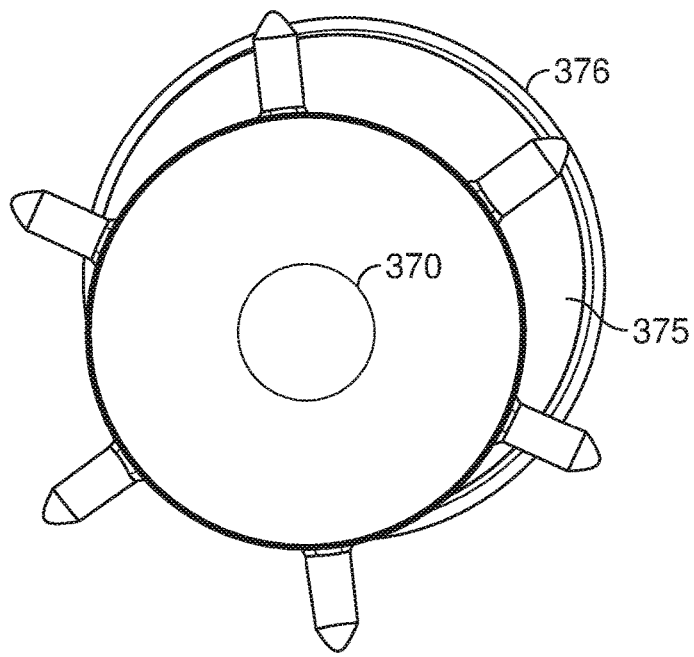
FIG. 28D is a top view of a capstan assembly in a second configuration, according to one embodiment.

As shown in FIG. 28C, when the ship's wheel 271 is rotated relative to the spiral guide element 376, the wheel guide extension 374 travels within the spiral pathway 377 defined within the spiral path element 376, which may be coupled to the upper adapter place 360 of FIG. 27C, for example. In so doing, the spiral guide element 376 is shifted away from the substantially centered configuration shown in FIG. 28C to the more eccentrically-disposed configuration shown in FIG. 28D. That is, when the wheel guide extension 374 is disposed within the spiral pathway 377 closest to the central well 370, the spiral path element 376 is substantially centered on the ship's wheel 370, as shown in FIG. 28C. In this configuration, the upper adapter plate 360 is in a first, initial configuration. As the ship's wheel 271 is turned and as the wheel guide extension 374 travels within the spiral pathway 377, the spiral path element 376 deviates more and more from its initial centered position to an eccentric position relative to the wheel well 370, as shown at FIG. 28D. At its outermost position within spiral pathway 377, the wheel guide extension 374 forces the spiral path element 376 some distance in the x-y plane (see FIG. 27A), to thereby force the upper adapter plate 360 to correspondingly move the same amount along the x-y plane. The amount of eccentricity of the spiral path element (and thus movement of the upper plate 360 relative to the lower plate 358) may be readily adjusted by the user by fine-tuning the turning of the ship's wheel 271, as well as by simultaneously manipulating either or both capstan assemblies with the stereotactic table stage, x, y, z controls as described above in paragraph 62.

Turning now back to embodiments of the present excisional device, it is to be notes that, herein, the phrase "helical element" and the terms "helix" or "helices" are intended to encompass a broad spectrum of structures. Indeed, the structures shown herein are but possible implementations of a helical element, helix or helices. According to other embodiments, "helical element", "helix" or "helices" and equivalent expressions may be implemented as tubes having one or more slot-shaped openings or fenestrations along at least a portion of length thereof. Such fenestrations may be substantially parallel to the longitudinal axis of the tube or may be disposed, for example, in a spiral configuration. The fenestrations may be continuous along at least a portion of the length of the tube or may be discontinuous, such as to result in a plurality of such parallel or spirally wound fenestrations. The fenestrations may be very wide such that the resultant structure resembles a spring, or more narrow, such that the resulting structure more closely resembles a tube having narrow, slot-shaped openings therein. The continuous or discontinuous fenestrations may be caused to assume other configurations along at least a portion of the tubes in which they are formed. For example, the fenestrations may be caused to form a zigzag pattern such as "NNNN . . . ", "/VVVVV" or "VVVV . . . " or a cross-shaped pattern, such as "XXXXX". Significantly, the terms "helical element", "helix" or "helices" should be understood to cover a spectrum of structures, from a spring-like structure as shown in FIGS. 2-14, to tubes having selected slot-shaped openings, examples of which are shown in FIGS. 17A-22.

FIGS. 29A-29D show structure of another embodiment of an excisional device according to one embodiment. As shown, the structure referenced by numeral 280 of FIG. 29A may replace the first helical element described above and may discharge, together with the proximal sheath shown at 284 in FIG. 29B, the tissue transport functionality. That is, the helical element 280, which may rotate independently of the work element(s), urges the cored and severed specimen from the distal portion thereof to the transfer magazine 27. As shown, the helical element 280 may be formed of a hollow tube in which one or more slot-shaped openings or fenestrations 282 may be defined. Such fenestrations 282 may be continuous or discontinuous, non-overlapping or overlapping. In the implementation shown in FIG. 29A, a plurality of fenestrations 282 (which may be laser-cut from the tube forming the proximal sheath), are disposed in a generally spiral configuration. Other configurations are possible.

Figure 29A:
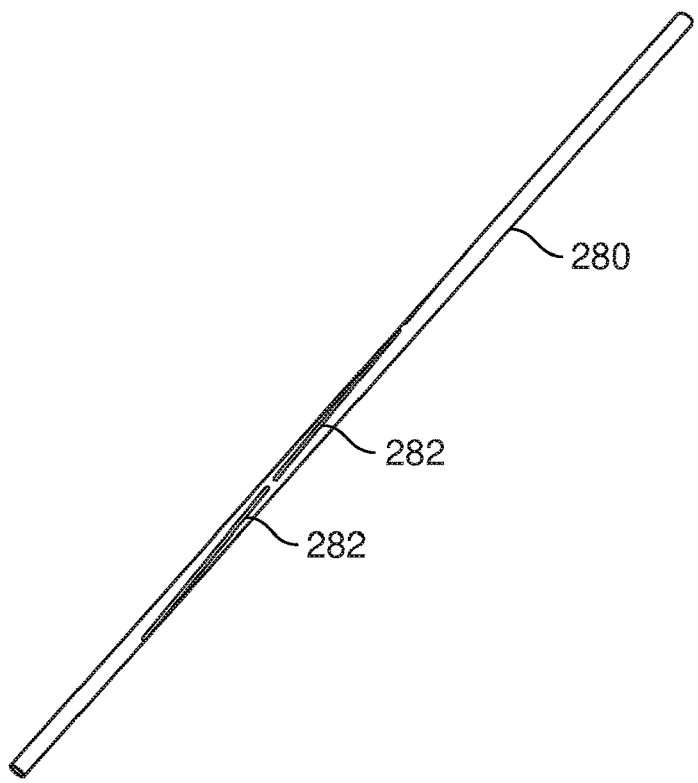
FIG. 29A shows structure of an element of an excisional device according to one embodiment.
Figure 29B:
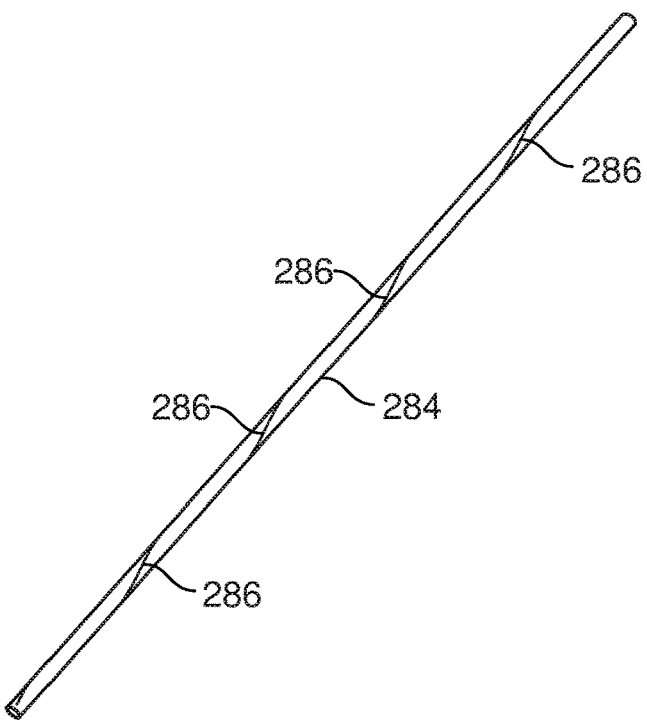
FIG. 29B shows structure of an additional element of an excisional device according to one embodiment.
Figure 29C:
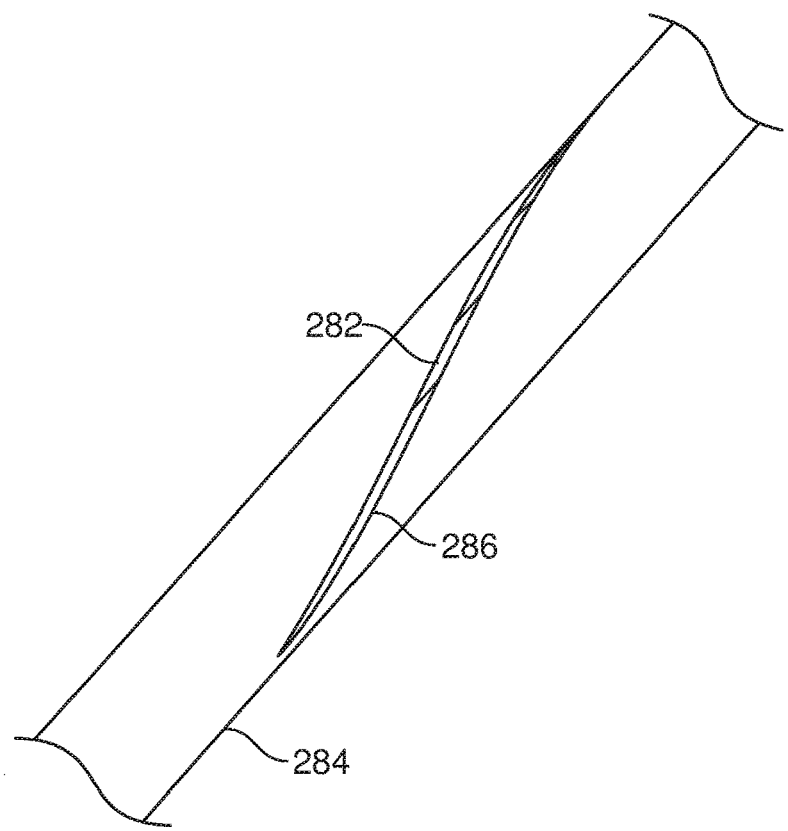
FIG. 29C shows still more structure of an element of an excisional device according to one embodiment.

FIG. 29B shows one embodiment of a proximal sheath 284 of an excisional device according to one embodiment. The proximal sheath may discharge a dual function of actuating the tendon actuating element 469 (if configured as in FIG. 19) through differential motion thereof with the body portion 428 (FIG. 19), as well as working in concert with the helical element 280 to transport the cored and severed tissue samples proximally toward the storage or transfer magazine 27. The proximal sheath 284 may be coupled to the body portion 428 and to the actuation element 469 of the work element as shown, for example, in FIGS. 21 and 22. As shown in FIG. 29B, the proximal sheath 284 may comprise one or more slot-shaped (for example) fenestrations 286. In the implementation of FIG. 29B, the fenestrations are narrow slots that are disposed in a spiral pattern. These slots may be continuous or discontinuous overlapping or non-overlapping, of uniform or non-uniform width. Fenestrations, slots or openings of different shapes are expressly encompassed herein. As shown in FIG. 29B, the fenestrations 286 may be spirally-wound around the tube, and the direction of the resulting spiral pattern may be the same as that of the helical element 280. However, when the proximal sheath 284 is fitted over at least a portion of the helical element 280, the respective spiral (or other) fenestration patterns may be crossed such that the fenestration pattern in the helical element 280 cross the fenestration pattern in the proximal sheath 284 or not, depending on the relative axial position between these two helical elements at any given time, as shown in FIG. 29C.

Figure 29D:
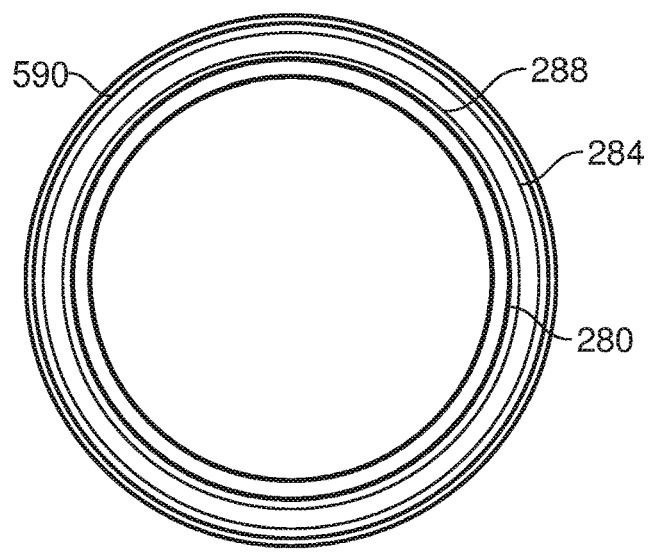
FIG. 29D shows further structure of an excisional device according to one embodiment.

According to one embodiment, effective tissue transport may be achieved when the right balance is achieved between the resistance to tissue advancement as between the helical element 280 and inner wall of the proximal sheath 284. In order to promote the longitudinal (axial) movement of the cored and severed tissue sample within the helical element, stopping or greatly reducing the rotation of the sample may be beneficial. As noted above, the proximal sheath 284, according to one embodiment, is fitted over at least a portion of the helical element 280, as shown end-on in FIG. 29D. FIG. 29D shows the annular space 288 formed between the outer wall of the helical element 280 and the inner wall of the proximal sheath 284. According to one embodiment, a flush may be incorporated in the annular space 288, or between the outer sheath (which may actually take the form of either a distal sheath 590 or an outer sheath 512 previously referred to in other figures, but referred to collectively as 590, according to embodiments and as shown in this figure for simplicity) and inner sheaths, to further facilitate tissue transport. Moreover, a vacuum may be drawn within at least the helical element, which may further facilitate tissue transport. This enables the user to collect any fluids to enhance cleanliness during the procedure, to help with visualization and to collect cells for cytology. Moreover, according to one embodiment, such a flush pathway enables the delivery of, for example, biologically active substances and/or markers. It should be noted that, according to embodiments, an inner helical element 280 may not be present, while other embodiments, such as those using a split tube long monolithic beak assembly, such as previously described in FIGS. 15A, 15B and 15C above, may only have two concentric tubes, which may be considered to be an outer sheath and the inner long beak assembly.

Coupled with flush and vacuum, the fenestrations defined in the proximal sheath 284 and in the helical element 280 may enable a helical "pumping" feature and to create a reservoir of fluids surrounding the tissue, which may enable a swirling wave action to interact with the cored and severed tissue samples to gently push them in the proximal direction. The fenestrations in both the helical element 280 and the proximal sheath 284, as examples of such fenestrations or features, lessen the respective wall surface areas of these structures and thus decrease the surface friction experienced by the cored and severed tissue sample both of which (wall surface area and friction) impede transport. Such structures also exhibit a favorable "sealing" effect surrounding the tissues, particularly where irregular tissues might, based on their own surface architecture, engender vacuum leaks. Indeed, the gentle urging of the cored and several tissue samples preserves the underlying tissue architecture and delivers a clinically-useful sample (e.g., one whose tissue architecture has not been unacceptable damaged during its transport) to the transfer magazine 27.

One embodiment, as discussed above and shown relative to FIGS. 29A-D, replaces the discrete, spring-like helical element with a tube 280 having one or more slot-shaped fenestrations defined therein. Replacing a discrete helical element with the variant shown in FIG. 29A eliminates a separate structure that otherwise would have been required to both transmit torque and provide differential forces in a longitudinal direction for beak actuation. Moreover, eliminating a spring-like helical member in favor of a unitary tube in which slot-shaped (for example) fenestrations may be present reduces the parts count and eases manufacturing of the device 10. The structure of FIG. 29D comprising the proximal sheath 284 fitted over at least a portion of the helical element 280 provides simplicity, robustness, increased actuation precision, a decreased torque drain and less disruptions in the architecture of the transported tissue sample.

According to one embodiment, a thin outer sheath 590 may be disposed over at least a portion of the proximal sheath 284. The thin outer sheath 590, according to one embodiment, may be configured to be non- or manually rotating. According to one embodiment, the outer sheath 590 (shown in FIG. 29D) may be formed of or comprise, for example, polyimide.

According to another embodiment, and as shown in FIG. 20, the non- or differentially rotating distal sheath (not shown in this FIG. 29D specifically) may be configured to fit over the work element as shown in FIG. 19 comprising the body portion 428, the tendon actuating element 469 and at least a portion of the first or first and (if present) articulable beaks. The outer sheath 590 may be configured to slide and fit over both the distal and the proximal sheath 584 that is mechanically coupled to the work element. In such an embodiment, the inner or first helical element may be deleted entirely, but the helical slots previously shown in element 280 of FIG. 28A may be incorporated into such distal sheath. The outer sheath 590, according to embodiments may cover the distal sheath to prevent or lessen tissue wind-up during rotation. The outer sheath 590 may also create an annular space for flush to travel forward to its distal end, depositing flush, anesthetics, anticoagulants, vasoconstrictors and the like to the very distal end of the work element: that is, to the beak or beaks and/or to the scoopula-shaped distal end of the device. The outer sheath 590 may function to protect the beak(s) of the work element during opening thereof, to prevent the beak(s) from experiencing too great strangulation forces, as the beak(s) of the work element may be caused to move slightly proximally during beak opening, such that the beaks open (for the most part) under the shelter provided by the outer sheath 590. The thin (e.g., polyimide or thin hypotube) outer sheath also protects the tendons and the living hinge areas of the work element, as well as the distal portions of the beak or beaks by removing some of the rotational resistance. Moreover, such outer sheath 590 may also provide cover and protection for at least part of the distal sheath and proximal sheath 284 that does not flex inward with the living hinge and work elements, such that these do not snag tissues during forward excursion within tissue. Lastly, a polyimide or other material outer sheath 590 may have a naturally or coated lubricious surface that is highly impervious to chemicals that the excisional device is likely to encounter and can readily be sterilized.

FIGS. 30A and 30B show another embodiment of a work element, according to one embodiment. Specifically, the work element 13 in FIG. 30A is similar to that shown in FIGS. 21 and 22 (although two beaks are shown in FIG. 30A). Attention is drawn to the proximal end of the work element 13. Therein, the body portion 428 of the work element 13 may be mechanically coupled to the tendon actuating element 469 at the proximal end of the work element. Note that the tendon actuating element 469, from the embodiment of FIGS. 21 and 22, is already coupled to the body portion 428 through the tendons 468, 470, toward the distal end of the work element 13. That is, the entire work element 13 may be formed of a single homogeneous material—such as from a single hollow tube that is (for example) laser-cut to form the structures shown in FIGS. 30A and 30B. Two beaks are shown. It is to be understood, however, that such need not be the case, as the work element 13 may comprise multiple beaks or a single beak that acts against a non-moveable part such as a fixed trough-shaped or scoopula-shaped distal portion of an outer sheath, such as element 512 from FIGS. 15A and 15B above.

According to one embodiment, as shown in FIGS. 30A and 30B, the proximal end of the tendon actuating element 469 may be mechanically coupled to the proximal portion of the body portion 428. Such mechanical coupling may be configured to maintain the tendon actuating element centered on the cutout in the body portion formed to accommodate the tendon actuating element 469 and/or to provide additional biasing force in the distal direction, as well as to aid in manufacturing. One embodiment comprises a resilient member 427 having one end thereof coupled to the tendon actuating element 469 and another end thereof coupled to the proximal portion of the work element 13. Such a resilient member 427 may be configured to bias the beak or beaks of the work element 13 in the open configuration, such that a sufficiently great proximally-directed force applied to the tendon actuating element 469 tends to close the beak or beaks. Conversely, release of such proximally-directed force causes the resilient member 427 to release the energy stored during the extension thereof and return to its un-extended state, thereby exerting a distally-directed force on the tendon actuating member 469, winch causes the beak or beaks to return to its or their default open configuration.

Also shown in FIG. 30B, attachment holes 292A and 292B may be provided on the body portion 428 and on the tendon actuating element 469, respectively. Such attachment holes 292 may, according to one embodiment, indicate the location of, for example, spot welds, as detailed below.

Figure 31:
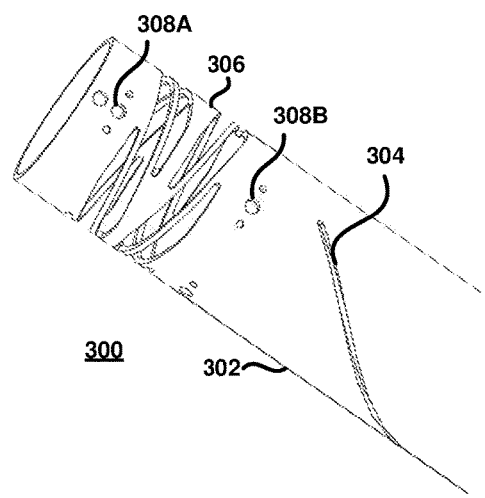
FIG. 31 shows the distal end of a proximal sheath of an excisional device according to one embodiment.
Figure 32:
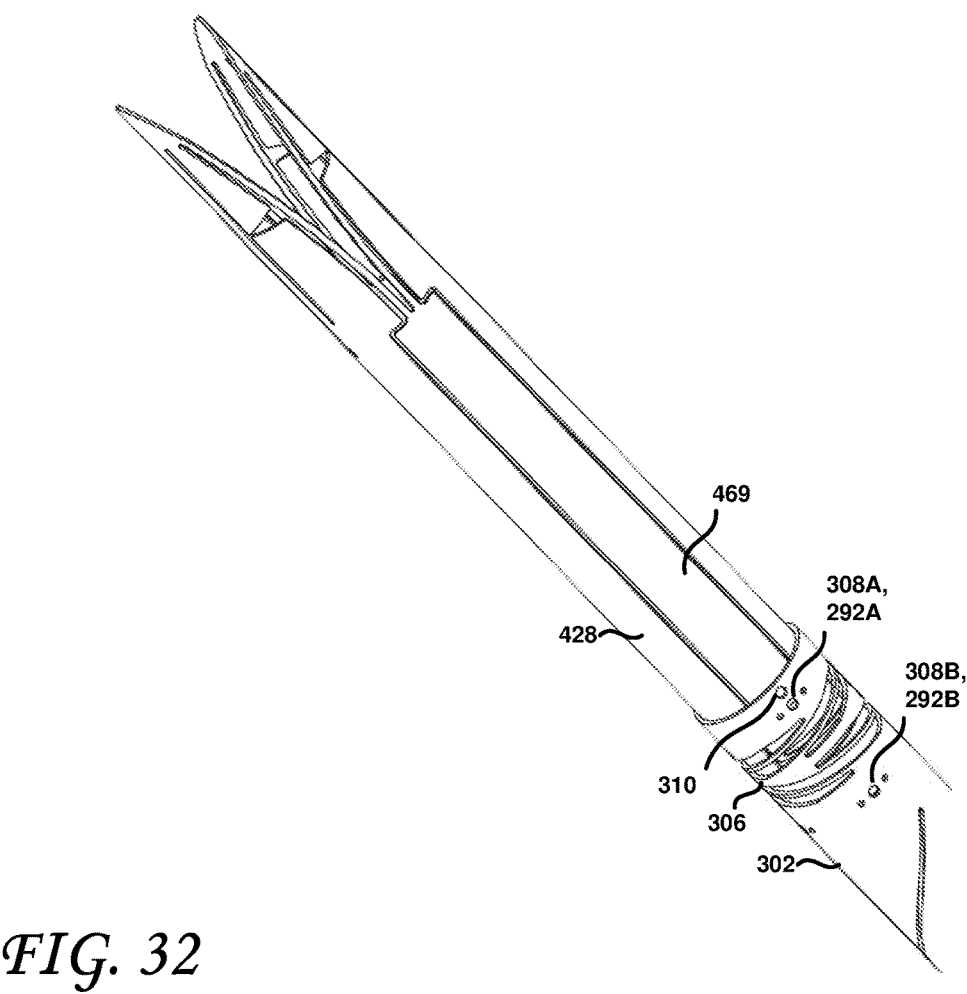
FIG. 32 shows an assembly comprising the monolithic beak assembly and the proximal sheath of an excisional device according to one embodiment.

FIG. 31 shows a distal portion of a proximal sheath according to one embodiment. The proximal sheath 300, as shown in FIG. 31 may comprise a number of fenestrations or slots 304 that run through the wall of the proximal sheath 300, from an outer surface to the interior lumen thereof. The distal portion of the proximal sheath 300 may be configured to fit over and attach to the proximal end of the monolithic beak assembly 13 of FIGS. 30A and 30B. During assembly of the present excisional device and as shown in FIG. 32, the attachment holes 308A and 308B of the proximal sheath 300 may be lined up with the attachment holes 292A and 292B, respectively, of the monolithic beak assembly 13 and the proximal sheath 300 attached to the monolithic beak assembly 13 at attachment points 292A, 308A and 292B, 308B. According to one implementation, the attachment point 308A of the proximal sheath 300 may be spot-welded to the attachment point 292A of the tendon actuating member 469 of the monolithic beak assembly 13. Although not shown in these figures, corresponding attachment points may be provided on the hidden side of the device. Similarly, the attachment point 308B of the proximal sheath 300 may be spot-welded to the attachment point 292B of the body portion 428 of the monolithic beak assembly 13. As also shown in FIG. 31, the distal portion of the proximal sheath 300 may define a resilient or spring portion, as shown at reference numeral 306.

Figure 33:
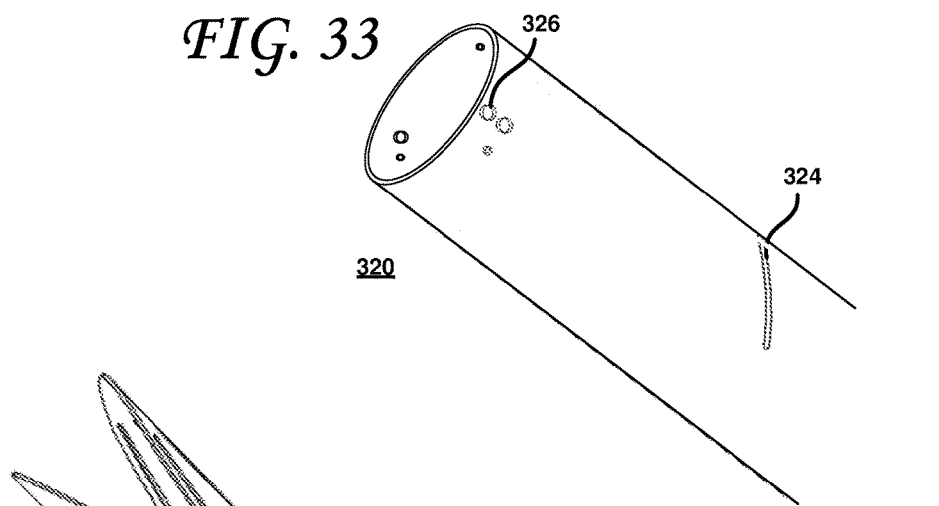
FIG. 33 shows the distal end of a distal sheath of an excisional device, according to one embodiment.
Figure 34:
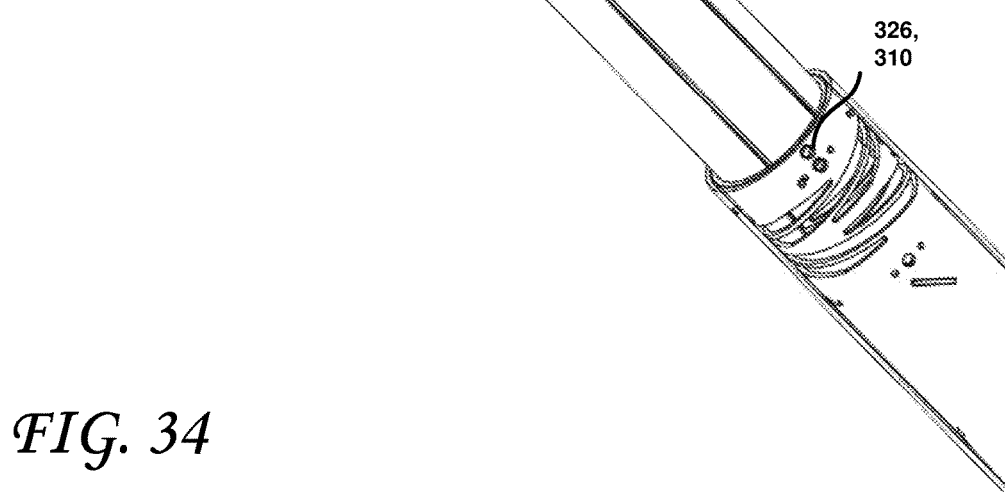
FIG. 34 shows an assembly comprising a monolithic beak assembly, a proximal sheath and a distal sheath, according to one embodiment.

FIG. 33 shows the distal portion of a distal sheath 320, according to one embodiment. The distal sheath 320 may be configured to fit over the proximal sheath 300 and the attachment point 326 of the distal sheath 320 attached to attachment point 310 on the proximal sheath 300, as shown in FIGS. 32 and 34. For example, the attachment point 326 of the distal sheath 322 may be spot-welded to attachment point 310 on the proximal sheath 300, as suggested in FIG. 34. The distal sheath 320 is transparently illustrated in FIG. 34, to show underlying detail. It is to be understood that spot-welding is but one method of attaching the constituent components of the present excisional device to one another. Other attachment technologies may also be used, as appropriate. Once the distal sheath 320 is spot welded in place, it will rotate in synchronicity with the beak assembly 13 and proximal sheath 300, but will be able to move axially relative to proximal sheath 300. Such axial movement between the distal and proximal sheaths will positively open and/or close the beak or beaks of monolithic beak assembly 13, as previously discussed.

Figure 35:
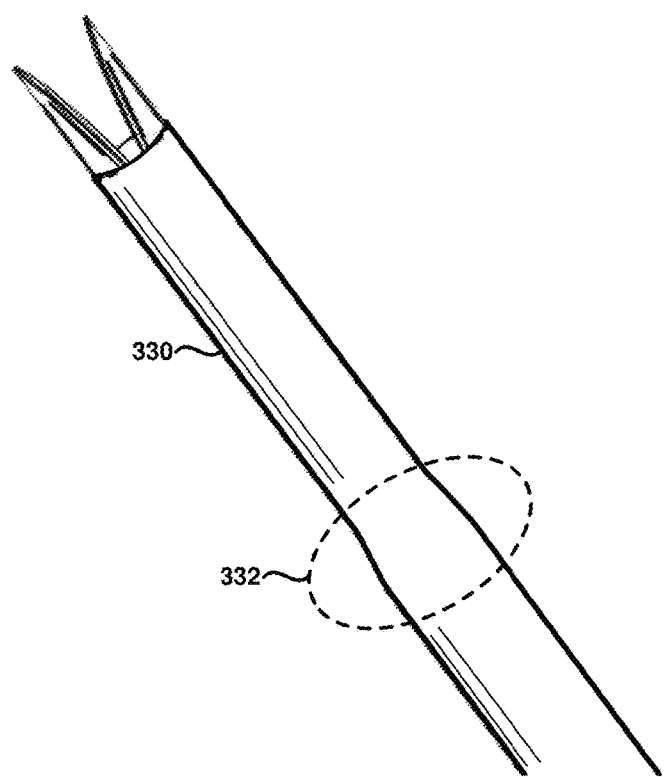
FIG. 35 shows the distal portion of an excisional device according to one embodiment.

FIG. 35 shows one embodiment of the present excisional device, in a still further intermediate state of assembly. In FIG. 35, an outer sheath 330 has been fitted over the assembly comprising the monolithic beak assembly 13, the proximal sheath 300 and the distal sheath 320, and for purposes of illustration, without the scoopula shaped extremity that would be formed in the continuation of the outer sheath, in order to show the beaks 13 easily. For example, the outer sheath 330 may comprise polyimide or may comprise or be formed of stainless steel. The outer sheath 330 may be configured to be manually rotating, non-rotating, or at least differentially rotating with respect to the assembly comprising the monolithic beak assembly 13, the proximal sheath 300 and the distal sheath 320. That is, while the assembly comprising the assembly monolithic beak assembly 13, the proximal sheath 300 and the distal sheath 320 may rotate at relatively high rates of speed (in the thousands of revolutions per minute, for example), the outer sheath 330 may be held stationary or rotated as needed, wither manually or otherwise actuated by any mechanical means. For example, the user may rotate the outer sheath 330 a few tens of degrees at a time, as and when the procedure requires, for example in sampling around the clock as previously described. The outer sheath 330 may extend distally to the beaks of the monolithic beak assembly 13, may expose a greater proportion of the monolithic beak assembly 13 or may cover a significant portion of the beaks. According to one embodiment, one "side" of the outer sheath 330 may form a trough or scoopula shape and extend at least slightly beyond the distal-most tip of the beak or beaks of the monolithic beak assembly 13. Indeed, the embodiment shown and described relative to FIGS. 29A through 33 may comprise a single beak or two or more beaks.

According to one embodiment, the outer sheath 330 may be dimensioned so as to allow an annular space to exist between the outer surface of the distal sheath, the distal portion of the monolithic beak assembly 13 along with the distal sheath 320 and the inner wall of the outer sheath 330. This annular space allows for flush to be introduced at selected stages in the procedure. The flush may provide lubrication for the rotation of the assembly comprising the assembly monolithic beak assembly 13, the proximal sheath 300 and the distal sheath 320 and may facilitate the rotation and thus the transport of the cored and severed tissue specimen in the distal direction. According to one embodiment, when the beak or beaks of the monolithic beak assembly is or are in the open configuration, the fenestrations or slots 304 (FIG. 31) defined in the proximal sheath 300 are not lined up with the fenestrations or slots 324 (FIG. 33) defined in the distal sheath 320. However, according to one embodiment, when the beak or beaks are actuated, and the beaks are closing, are closed or are substantially closed, the fenestrations or slots 324 defined in the distal sheath 320 become or are lined up or substantially lined up with corresponding one or ones of the fenestrations or slots 304 defined in the proximal sheath 300. In this state, if there is flush in the annular space between the outer surface of the distal sheath 320 and the timer wall of the outer sheath 330, this flush will enter the interior lumen of the device (where the cored and severed tissue specimens are collected and are transported). Moreover, as the flash may have been entrained into rotation in the aforementioned annular space as the assembly comprising the monolithic beak assembly 13, the proximal sheath 300 and the distal sheath 320 rotates, the rotating flush may enter this interior lumen with some force and may exert that force on any cored and severed tissue specimen therein. This flush may act as a lubricant as well, to the specimen contained in the inner lumen of the device. According to one embodiment, a vacuum may be drawn within the interior lumen of the device. According to one embodiment, the force imparted on the cored and severed tissue specimen, together with the force imparted on such specimen by the flush entering this interior lumen, draws and transports the cored and severed tissue specimen in the proximal direction, for eventual transport to the transfer magazine 27, for example.

Transport may be aided by the shoulder shown at 332 in FIG. 35. Indeed, this shoulder encompasses the location defined by the proximal end of the monolithic beak assembly 13 and the distal end of the proximal sheath 300. As the diameter of the proximal sheath 300 is somewhat greater than that of the proximal end of the monolithic beak assembly 13, the interior lumen of the proximal sheath 300 is correspondingly greater than the interior lumen of the monolithic beak assembly 13. As the cored and severed tissue specimen eater the interior lumen of the monolithic beak assembly 13, they may be somewhat compressed. Such compression may be somewhat relieved as the tissue specimens transition from the lumen of the monolithic beak assembly 13 to the lumen of somewhat greater diameter of the proximal sheath 300, at shoulder 332. This decompression of the tissue specimen in the lumen of the proximal sheath 300 may, together with the flush and the vacuum, also facilitate tissue transport. The shoulder at 332 could expand the inner lumen diameter in the range of 0.001 inch to 0.100 inch additional over the original lumen internal diameter or double the lumen internal diameter, whichever is greater. As previously mentioned, shoulder features may be incorporated into the proximal sheath, distal sheath and outer sheath to augment such tissue expansion/transport action.

Figure 36:
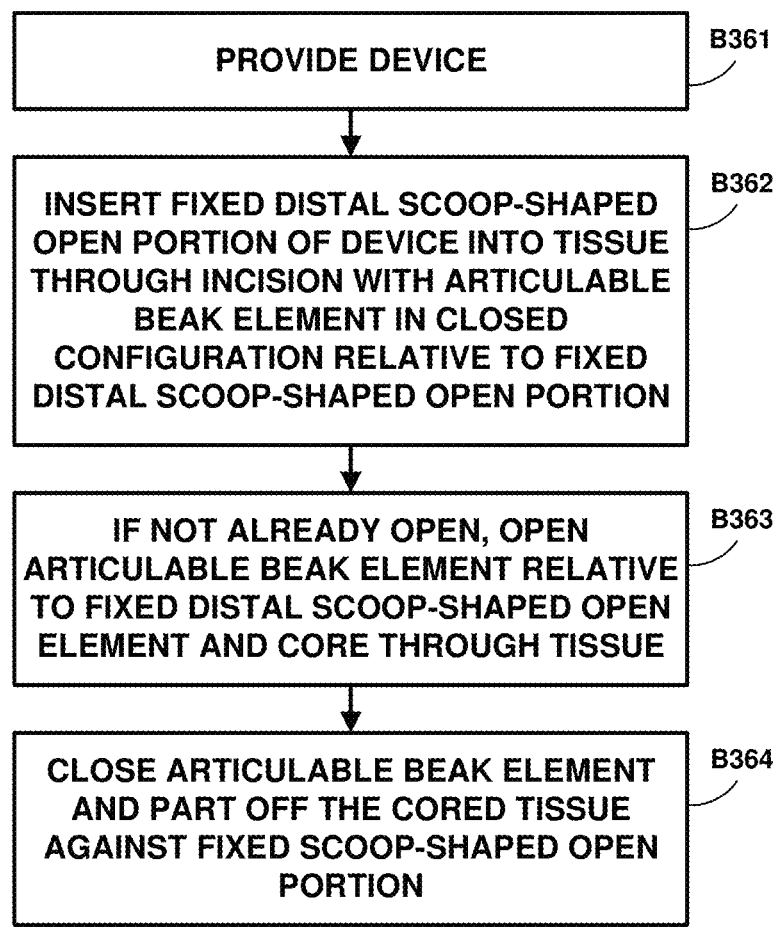
FIG. 36 is a flowchart of a method according to one embodiment.

FIG. 36 is a flowchart of a method according to one embodiment. As shown therein, block B361 calls for providing a device. According to one embodiment, the provided device may compose an outer sheath and an inner assembly configured to be received (at least partially) within the outer sheath. The outer sheath may define a diameter, a longitudinal axis, a proximal portion and may comprise a fixed distal scoop or trough-shaped open portion. The inner assembly may define a proximal portion, a distal portion and a body portion between the proximal and distal portions. According to one embodiment, the distal portion may comprise an articulable beak element configured to core through and cut tissue. Block B362, as shown, calls for inserting the fixed distal scoop-shaped open portion of the biopsy device into tissue through an incision, with the articulable beak element(s) in a closed configuration relative to the fixed distal scoop-shaped open portion. As shown at B363, if not already open, the articulable beak element may be opened relative to the fixed distal scoop-shaped open portion and a step or coring through the tissue may be carried out. According to one embodiment, the articulable beak element may be rotating during all or part of the coring. The articulable beak element may then be closed and the cored tissue may be parted-off against the fixed distal scoop-shaped open portion, as shown at B364. The articulable beak element may be rotating during the parting-off. As previously described, the parted-off cored tissue may then be transported in the proximal direction within the inner assembly.

Figure 37:
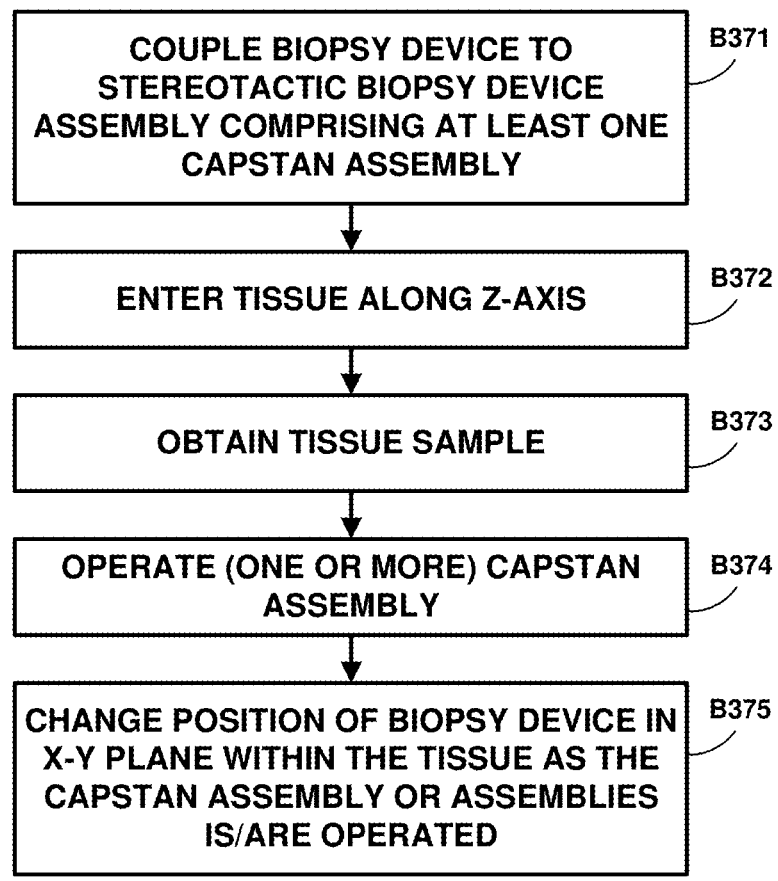
FIG. 37 is a flowchart of a method of positioning a biopsy device, according to one embodiment.

FIG. 37 is a flowchart of a method of positioning a biopsy device, according to one embodiment. As shown therein, Block B371 calls for coupling a biopsy device to a stereotactic biopsy device assembly comprising at least one capstan assembly. One embodiment of a suitable capstan is shown in FIGS. 27A-C and FIGS. 28A-D. The stereotactic biopsy device assembly may be configured to couple to a stage of a stereotactic table. According to one embodiment, the stereotactic biopsy device assembly may comprise a first portion configured to fixedly couple to the stage and a second portion movably coupled to the first portion. A first capstan assembly may be configured to couple to the second portion of the platform and to the biopsy device. Block B372 calls for the biopsy device to enter the tissue along the z-axis, whereupon a tissue sample may be obtained, as shown at B373. The capstan assembly may then be operated, as shown at B374. For example, a ship's wheel (or other type of actuator) of the capstan assembly may be turned or otherwise actuated, either manually or by machine using either Cartesian or polar coordinates, within the degrees of freedom allowed by the capstan assembly. The capstan assembly may be operated entirely manually, controlled by the user using his or her best clinical judgment and skill, optionally under direct visualization. The position of the biopsy device in the x-y plane within the tissue may then be changed (changing the angle of attack of the biopsy device) as the capstan assembly or assemblies is/are operated, as shown at B375. For example, capstan assemblies may be used to identically or differentially raise or lower the distal and/or proximal ends of the biopsy device and to move the biopsy to a position that is off-center relative to its initial position. The biopsy device may also be rotated in conjunction with the movement imparted thereto by the capstan assembly or assemblies coupled thereto.

Figure 38:
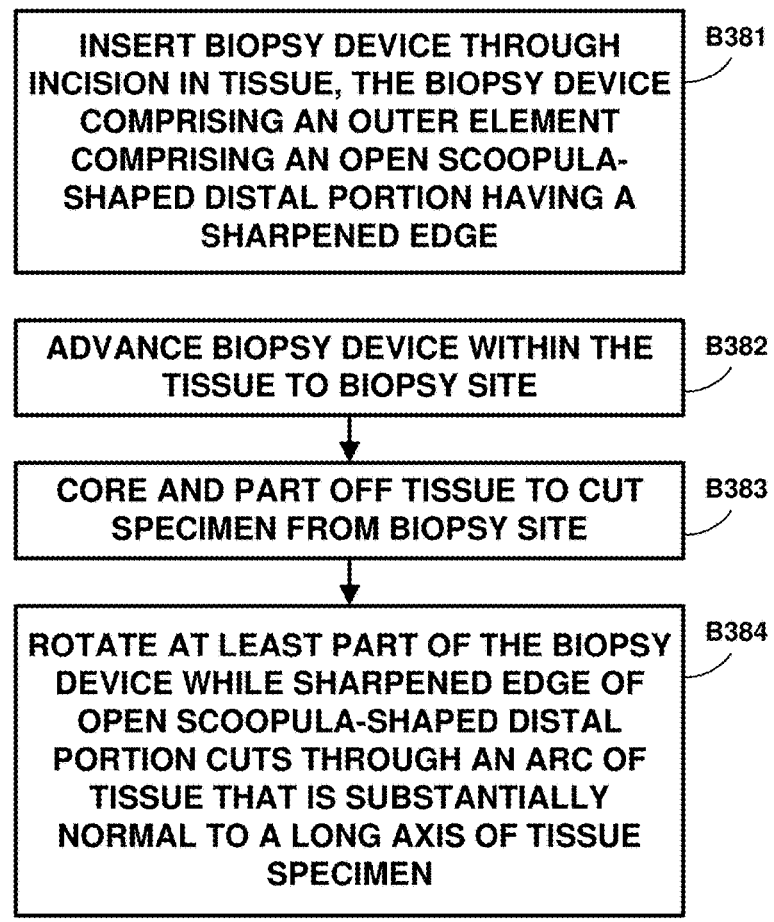
FIG. 38 is a flowchart of another method according to one embodiment.

FIG. 38 is a flowchart of another method according to one embodiment. As shown in FIG. 38, Block B381 calls for inserting a biopsy device through an incision in tissue. According to one embodiment, the inserted biopsy device may comprise an outer element comprising an open scoopula-shaped distal portion having a sharpened edge, and an inner assembly configured to fit at least partially within the outer element and comprising a tissue coring and parting off assembly. As shown at B382, the biopsy device may then be advanced within the tissue to the intended biopsy site. B383 calls for coring and parting off the tissue to cut a first tissue specimen from the biopsy site. At least the outer element may be rotated as shown at B384, while the sharpened edge of the open scoopula-shaped distal portion cuts through an arc of tissue. According to one embodiment, the arc of tissue may be oriented substantially normal to the long axis of the tissue specimen. That is, according to one embodiment, the open scoopula-shaped distal portion may be rotated about its longitudinal axis (e.g., 14 in FIG. 15B), which is normal to the long axis of the tissue specimen (shaped like, according to one embodiment, short segments of a tube, with tapered proximal and distal ends). After rotating, one or more further tissue specimens may be cut from the tissue facing the open scoopula-shaped distal portion, which facing tissue may be radially separated from the tissue from which the previous, pre-rotation specimen was cut.

According to one embodiment, the inserting in Block B381 may be carried out with the tissue coring and part-off assembly comprising at least one articulated beak element. Coring and parting off, rotating and generating steps may be repeated as desired to generate tissue specimens at least partially "around the clock", that is, at least partially about 360 degrees of rotation. The tissue may be caused to prolapse or to prolapse further into the open scoopula-shaped distal portion after the rotating step of Block B384. Such may be carried out by, for example, imposing an axially-directed movement on the biopsy device before or after the rotating step. The cut specimen(s) may then transported within the biopsy device away from the biopsy site. Advancing the biopsy device within the tissue in Block B382 may cause the sharpened edge of the open scoopula-shaped distal portion to dissect tissue along an insertion path. According to one embodiment, as the coring and part-off assembly is advanced such that the distal tip thereof faces the distal tip of the open scoopula-shaped distal portion, the coring and parting off of the tissue may be carried out with substantially zero dead space at the distal tip of the biopsy device. Conversely, the tissue coring and parting off assembly may be retracted away from the distal tip and sharpened edge of the open scoopula-shaped distal portion during the advancing and/or rotating steps or for such purposes as parting off a specimen that is less than the full length of the scoopula, as well as other purposes. Such advancing, retracting and rotating steps may be carried out stereotactically or may be controlled or carried out manually by the user of the biopsy device. The sharpened edge of the open scoopula-shaped distal portion may be configured to cut at an angle that is substantially normal (i.e., substantially perpendicular) to a long axis of the specimens (generally tapered tube-shaped pieces of tissue) cut and collected by the biopsy device.

As shown in the figures and as noted above, the proximal sheath 300, according to one embodiment, may be attached to the body portion 428 as well as to the tendon actuating portion 469 of the monolithic beak assembly 13. In turn, the distal sheath 320 may be attached to the proximal sheath 300 at attachment point 326. In this manner, rotation of the distal sheath will entrain the monolithic beak assembly and the proximal sheath 300 in rotation also or vice versa, depending on the driving mechanism of such embodiment. Therefore, according to one embodiment, the rotation for tissue specimen transport is the same as the rotation for specimen collection using the monolithic beak assembly. Moreover, since the interior lumen of the proximal sheath 300 may be relatively smooth and as the interior lumen thereof may be further lubricated with flush entering the lumen through aligned fenestrations 304, 324 in the proximal sheath 300 and the distal sheath 320, the tissue specimen may be transported substantially intact (e.g., with the tissue architecture undamaged or not damaged to such a degree as to hinder examination) to the transfer magazine 27 or to the proximal end of the interior lumen.

According to one embodiment, as attachment points 326 of the distal sheath 320 are attached to corresponding attachment points 310 on proximal sheath 300, which are attached to the tendon actuating member 469, a distally-directed force applied to the proximal sheath 300 acts to close the beak or beaks of the monolithic beak assembly 13. This is because the tendon actuating members 469 are acted upon by the axially stationary distal sheath 320, while the body portion of the monolithic beak assembly 13 is held by the proximal sheath 302, at attachment points 308B, 292B and moved axially forward, causing the beaks to close down via their living hinges. The spring or resilient portions 427 on the monolithic beak assembly 13, the spring or resilient portion of the proximal sheath 302 act in concert to bias the beak or beaks in the open configuration such that, when the distally-directed force imparted on the proximal sheath 300 is released, the beak or beaks of the monolithic beak assembly 13 retain to their default open configuration. It should be noted that holding the proximal sheath stationary axially while exerting a proximal force on the distal sheath will produce an identical beak open/closing mechanism, and may be selected to match with a driving mechanism that will accommodate such action, as may be envisioned by one skilled in the art.

According to one embodiment, the beak may be configured for actuation and cycling between a closed configuration (for penetration and part-off) and an open configuration (for coring and capturing tissue sample) while rotating. Such cycling between closed and open beak confirmations may be accomplished, according to one embodiment, using a push-pull mechanism that originates in a driving assembly far proximal to the beak structures themselves. Such a push-pull mechanism, between a proximal driver and the movable structures of the beak assembly including movement of living backbone hinge elements relative to living hinge tendon/keystone elements of the beaks, may comprise relatively rigid structures that can transmit small movements precisely, relying on column strength structural integrity combined with relatively inelastic tension structures to transmit these direct, linear forces over the length between the distal beaks and the proximal driver mechanism.

Such a driving mechanism may be appropriate for instruments that can rely on relatively short and rigid members between the handle (driver) and the working end. However, in the event the application requires a relatively long flexible catheter between the driver (proximal, handle end) and the working (distal) end, use of such a simple proximal push-pull motion that must be transmitted in a linear manner along a potentially tortuous pathway may present challenges. In fact, it has been determined that there are several factors that render a linear motion mode of force transmission along the length of a flexible catheter undesirable, in certain applications, as a way to transmit the precise forces needed to actuate the beak mechanisms to cycle between fully open and closed configurations. This is because the distal motions may be as small as several thousandths of an inch, particularly when the catheter is forced into, around and past curves needed to gain access to a treatment site. As a result, it has been found to be advantageous to generate the push-pull forces needed to actuate the beaks locally; that is, as near the actual living-hinge backbone and living tendon members as possible, using forces that are less affected by flexing the catheter over or through which these forces are transmitted.

One embodiment of such a distally-originated beak actuation mechanism is described herein. Significantly, one embodiment utilizes a mechanism that allows significant flexing of the catheter that connects the driver and the working distal end while providing forces that may be converted to small, precise, repeatable liner push-pull forces locally—that is, at the distal end very near to keystone and backbone, living hinge and tendon elements. In so doing, such relative motion causes the distal beak to cycle between open and closed configurations. This cycling between open and closed beak configurations may be carried out while also enabling powered rotation of the beak elements for penetration (closed beak), coring (open beak), and part-off/transport (closed beak) operating modes. It is also desirable to permit an open core transmission section between the distal beak elements and the storage chamber, which may be disposed proximal to the driving mechanism. Embodiments shown herein and detailed below fulfill these requirements.

Figure 39:
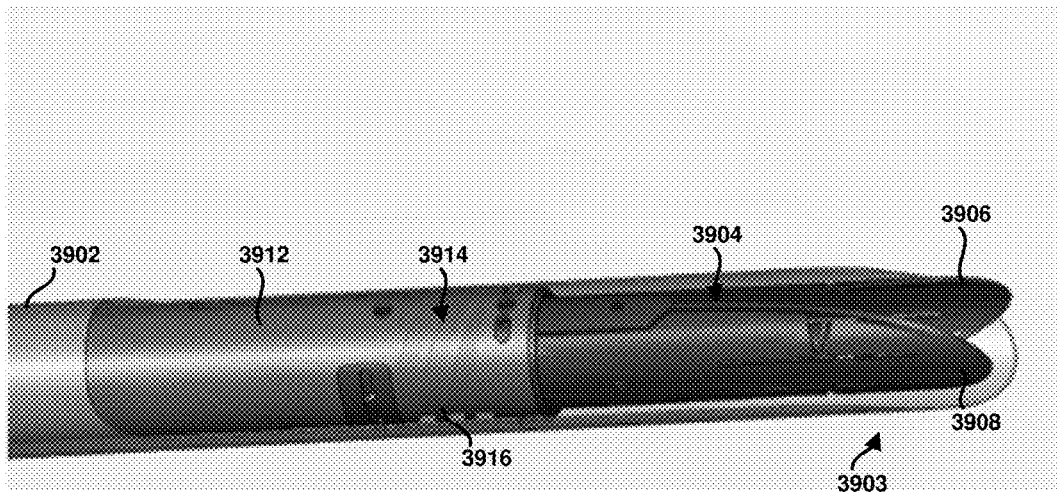
FIG. 39 is a view of a distal portion of an excisional device according to one embodiment.
Figure 40:
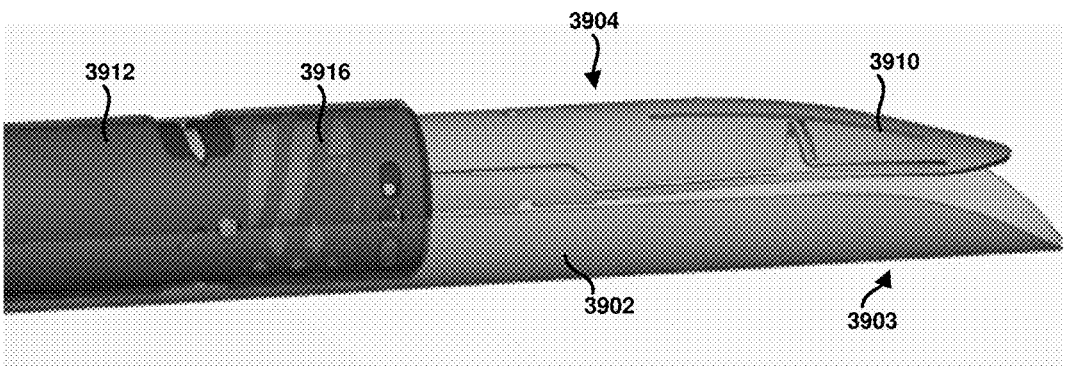
FIG. 40 is a view of a distal portion of an excisional device according to one embodiment.

FIG. 39 shows a twin-beak device, comprising a double beak coring/part-off assembly in relationship with a sheath 3902 comprising a distal scoop-shaped open portion 3903 (scoopula), according to one embodiment. FIG. 39 shows an inner element comprising an articulable distal assembly 3904. In FIG. 39, the articulable distal assembly 3904 comprises two articulable members (beaks) 3906, 3908. In FIG. 40, the articulable distal beak assembly 3904 comprises a single articulable member 3910. In the embodiments of FIGS. 39 and 40, the articulable beak assembly 3904 is disposed in the innermost position within a middle tubular element 3912. In FIG. 39, the two beaks 3906, 3908 are shown in a distal position where they are about to be closed to part-off tissue (not shown) through which they have cored while rotating and traveling in a proximal to distal direction in the scoopula, in their wide open configuration. The mechanism and method, according to embodiments, for opening the twin beaks 3906, 3908 and keeping them open throughout their proximal to distal excursion may comprise rotating the tubular element 3912 (which is outer with respect to the inner element (that terminates distally with the articulable distal assembly 3904) and/or helical element, and inner relative to the non- or differentially rotating sheath 3902 and distal scoop-shaped open portion 3903) in a counter-clockwise (for example) direction, together with and after holding back the rotation of the inner element only a matter of degrees such that its helical/resilient element 3914 (seen through corresponding and co-axially-disposed helical/resilient element 3916 in the tubular element 3912), is driven back proximally, after which the inner element and the tubular element 3912 may rotate together until the desired closed configuration is achieved. In this example, the living backbone (hinge) element(s) of the articulable distal assembly 3904 is of one integral structure with its helical/resilient component 3914 ("threaded" section, nesting in a similar component in the middle tubular/helical "threaded" section) and has limited travel ability that comprises both rotation relative to the middle tubular/helical structure 3916 of the tubular element 3912 and longitudinal (linear, along the long axis of the excisional device) movement. Because the keystone element of the inner element is constrained such that it may only move in a circular slot in the middle tubular/helical/resilient structure 3916 of the tubular element 3912, which is at a finer pitch (shown here as 90 degrees to the long axis), the articulable distal member(s) (beak(s)) 3906, 3908, 3910 of the articulable distal assembly 3904 are necessarily open wide based on the relative linear motions imposed on keystone (attached to living tendons) and living backbone (hinge). Upon reaching the part-off region, (or at any time part-off or other reason to close the beak elements is desired) the inner-most tube/helix/resilient portion 3914 of the inner element is made to "catch up" while rotating, to the middle tubular/helical/resilient element 3916, thus causing the threaded elements of each of the tubular/helical/resilient components that are threaded with each other, to return to the resting or "closed" configuration and force a linear motion, again based on the fact that the keystone element is constrained to only move at a finer pitch (in this case approximately 90 degrees to the long axis of the roughly tubular elements) than those of the threaded elements to fully close the articulable distal assembly 3904.

FIG. 40 shows an embodiment in which the inner element comprises an articulable distal assembly 3904 comprising a single articulable member (beak) 3910 configured to operate based on similar principles and modes of operation as were discussed above relative to FIG. 39, in which the articulable distal assembly 3904 of the inner element comprised two (e.g., a first and a second) articulable members (beaks). In the depiction of FIG. 40, the single articulable member (beak) 3910 is already at a point where it is desirable to have it close down against the inner surface of the scoop-shaped open portion 3903 of the sheath 3902 for purposes of parting-off a cored specimen or for presenting a tapered profile to ease penetration within tissue to a target or for other purposes such as to deliver a substance or element to a site without allowing ingress of tissue during the approach to a target.

In this case, the rotating inner tubular/helical/resilient 3914 structure will have been made to "catch up" (briefly accelerated in rotation) with respect to the also rotating middle tubular/helical/resilient structure 3916, thereby closing the articulable distal assembly 3904 (in this case comprising a single articulable member or beak 3910) down against the scoop-shaped open portion 3903 of the sheath 3902. At that point rotation may be completely halted for beak retraction and transport of cored specimen(s) and the entire sequence repeated as often as desired.

One embodiment, therefore, is an excisional device that may comprise a sheath 3902; a tubular element 3912 configured for rotation with the sheath 3902 and an inner element configured for rotation and disposed as least partially within the tubular element 3912. The inner element may comprise an articulable distal assembly 3904 configured to core through tissue in an open configuration and part-off cored tissue in a closed configuration. According to one embodiment, differential rotation of the inner element (that comprises the distally-disposed articulable assembly 3904) with respect to the tubular element 3912 causes the articulable distal assembly 3904 to selectively assume the open and closed configurations.

According to one embodiment, the sheath 3902 may comprise a distal scoop-shaped open portion, shown in 3903 in FIGS. 39 and 40. Rotating the inner element comparatively faster than the tubular element may cause the articulable distal assembly 3904 to assume the closed configuration. Conversely, rotating the inner element comparatively slower than the tubular element 3912 may causes the articulable distal assembly 3904 to assume the open configuration. In one embodiment, the articulable distal assembly 3904 may comprise a single articulable member 3910 that may be configured to bear against the sheath 3902 when the articulable distal assembly 3904 is in the closed configuration. In another embodiment, the articulable distal assembly 3904 may comprise a first articulable member 3906 and a second articulable member 3908. The first and second articulable members 3906, 3908 may be configured to bear against each other when the articulable distal assembly 3904 is in the closed configuration. As noted above, the amount of the differential rotation of the inner element with respect to the tubular element 3912 is limited. Indeed, the articulable distal assembly 3904 may be mechanically coupled to the tubular element 3912 so as to allow a limited amount of differential rotation of the tubular element 3912 relative to the inner element. This limited amount of differential rotation of the tubular element relative to the inner element, however, is sufficient for the articulable distal assembly 3904 to selectively assume the open and closed configurations. The inner element may be configured to comprise a first resilient portion 3914 and the tubular element 3912 may be configured to comprise a second resilient portion 3916 that may be mechanically coupled (or at least constrained in its relative movement with respect) to the first resident portion 3914. Operationally, differential rotation of the inner element with respect to the tubular element may comprise the inner element lagging in rotation relative to the tubular element and/or the inner element leading in rotation relative to the tubular element.

Figure 41:
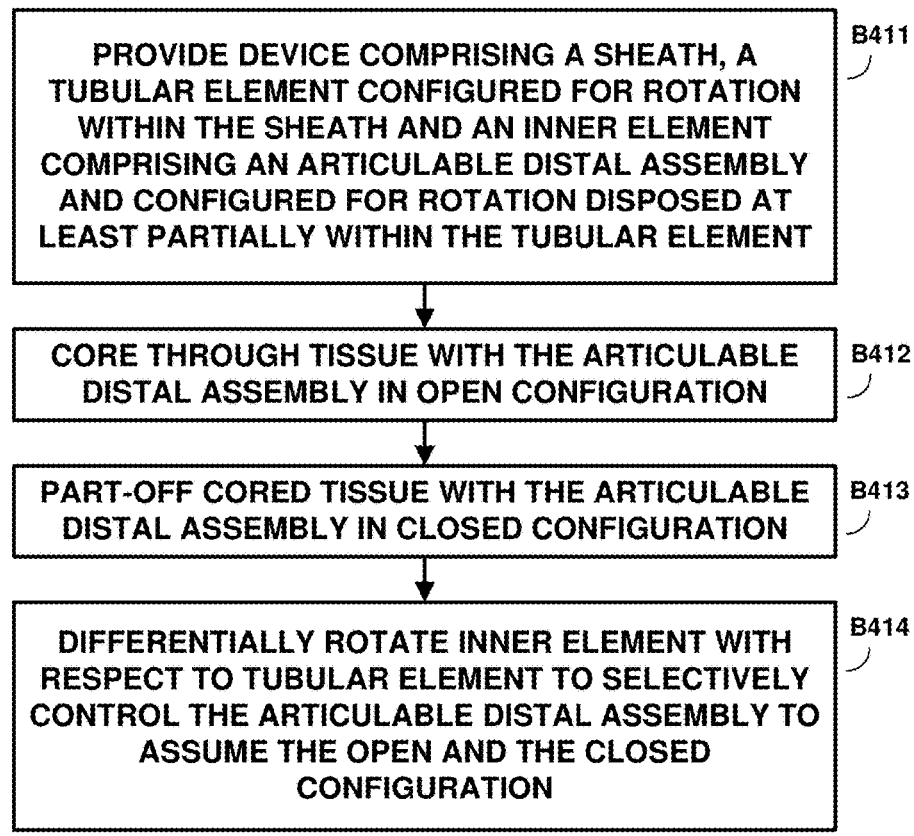
FIG. 41 is a flowchart of a method according to one embodiment.

FIG. 41 is a flowchart of a method according to one embodiment. As shown therein, block B411 calls for providing a device comprising a sheath, a tubular element configured for rotation within the sheath, and an inner element comprising an articulable distal assembly configured for rotation and disposed at least partially within the tubular element. Block B412 calls for coring through tissue with the articulable distal assembly in an open configuration. In block B413, the cored tissue may be parted off with the articulable distal assembly in a closed configuration. Lastly, B414 calls for different rotating the inner element with respect to the tubular element to selectively control the articulable distal assembly to assume the open (block B412) and the closed configuration (block B413).

Significantly, the coring and transport mechanisms and methods described and shown herein are configured to apply traction while coring, as the beak(s) either close against the scoopula, if one beak is used, or against each other if dual beaks are used and are then withdrawn to its or their resting position within the proximal edge of the scoopula opening, carrying the tissue specimen with it or them. That is, coring, cutting, parting-off traction and transport may be, according to one embodiment, carried out simultaneously. In so doing, as traction is applied during a cutting event the cutting event is not only rendered more efficient, but may be the only way to successfully cut certain tissue types. This traction, according to one embodiment, is facilitated by the continuous interaction of the helical element(s), the tubular coring and transport assembly, and the flush and aspiration, depending on embodiments, which all or separately act together to provide gentle continuous traction beginning immediately upon the tissue entering the lumen of the tubular coring and transport assembly 11 of FIG. 1 and continuing during part-off of the tissue specimen. According to one embodiment, the ratio between the twisting and pulling actions may be carefully controlled by, for example, control of rotation versus crank or cam speed, or other axial control mechanism. According to one embodiment, when the beak assembly is open wider than the inner lumen of the tubular coring and transport assembly, tissue is drawn in by at least the surface treatment(s), channels, and helical elements past the sharp beak assembly and into the interior lumen of the tubular coring and transport assembly. This may be, according to one embodiment, augmented with either flush or vacuum or both. However, it is to be noted that the transport mechanisms and functionality described herein is more effective than vacuum alone, as vacuum predominantly acts locally at the proximal surface of a specimen. Indeed, the transport mechanisms described and shown herein (e.g., surface treatments, rifling, vacuum slots, helical elements(s), and the selective rotation of these) may be configured to act along the entire length of the sidewalls of the tissue specimen, which may be useful in transporting certain tissue types. Vacuum, according to one embodiment, may well augment such traction and transport but need not be the primary modality by which tissue specimen are drawn proximally or materials are pushed distally to the target lesion site. According to one embodiment, vacuum may be used for extracting cells, body fluids and flush fluids, and to prevent the inadvertent injection of outside air, which may obscure an ultrasound image or transfer other unwanted elements into the body.

The present biopsy device may be formed of or comprise one or more biocompatible materials such as, for example, stainless steel or other biocompatible alloys, and may be made of, comprise or be coated with polymers, such as polyimide, and/or biopolymer materials as needed to optimize functions(s). For example, the cutting elements (such as the constituent elements of the beak assembly 13) may comprise or be made of hardened alloys and may be additionally coated with a slippery material or materials to thereby optimize passage through living tissues of a variety of consistencies and frictions. Some of the components may be purposely surface-treated differentially with respect to adjacent components, as detailed herein in reference to the transporting tubular and storage components. The various gears or pulleys may be made of any suitable, commercially available materials such as nylons, polymers such as moldable plastics, and others. If used, the motor powering the various powered functions of the present biopsy device may be a commercially available electric DC motor. The handle of the present biopsy device may likewise be made of or comprise inexpensive, injection-molded plastic or other suitable rigid, easily hand held strong and light-weight material. The handle may be configured in such a way as to make it easily adaptable to one of any number of existing guiding platforms, such as stereotactic table stages. The materials used in the present biopsy device may also be carefully selected from a ferro-magnetic standpoint, such that the present biopsy device maintains compatibility with MRI equipment that is commonly used for biopsy procedures. The vacuum/delivery assembly components may comprise commercially available vacuum pumps, syringes and tubing for competing to the present biopsy device, along with readily available reed valves for switching between suction and emptying of materials such as fluids, which may be suctioned by the vacuum components. The fluids collected by the embodiments of the present biopsy device in this manner may then be ejected into an additional external, yet portable, liquid storage vessel connected to the tubing of the present biopsy device, for discarding or for safe keeping for laboratory cellular analysis.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, for example, mechanical linkages or compressed air motors, may be used.

The cutting beak assembly of embodiments of the biopsy devices may be used, without alteration of their shape, attachment to any other modification, to penetrate tissue on approach to a target lesion. The cutting beak assembly may then be used to open and core the tissue specimen, and to thereafter part-off the specimen at the end of the coring stage. The beak assembly may also be used to help augment transport of the collected specimen. Having such multiple functions integrated in a single device saves valuable cross-sectional area, which in turn creates a device that has a minimal outer diameter while providing the maximum diameter core sample. Maximizing the diameter of the core sample is believed to be significant from a clinical standpoint, since it has been demonstrated in multiple peer-reviewed journals that larger diameter core specimens yield more accurate diagnoses. The clinical desire for large diameter core samples, however, must be balanced against the trauma associated with larger caliber devices. Embodiments optimize the ratio so that the clinician can have the best of both worlds.

Advantageously, according to one embodiment, an internal helical transport system may be configured to augment the coring function of the forward cutting beaks. The helical transport coring elements may be configured to apply gentle, predictable traction on the cored specimen, during and alter coring, which permits pairing the ideal speed of longitudinal excursion of the coring elements of the present biopsy device with the ideal speed of rotational movement of the same elements. In this manner, the architecture of the collected specimen is less likely to be disrupted during transport. It has been shown in peer-reviewed scientific articles that preserving tissue architecture (i.e., preserving the architecture of the tissue as it was in vivo) to the extent possible leads to an easier and more accurate diagnosis. The present vacuum/delivery mechanism may be configured to enable the force of vacuum to be exerted directly to the coring transport components, such that coring and transport of the specimen is handled as delicately, yet as surely, as possible and comprises non-significantly dimension-increasing components such as progressively sized fenestration features within collection magazine areas. If the present biopsy device were to rely solely on vacuum for tissue transport, then vacuum artifact, which is a known and descried phenomenon associated with conventional biopsy devices, might be present to a greater degree than is present (if at all) in embodiments described herein. On the other hand, were embodiments of the present biopsy device to rely solely on a physical pushing or pulling mechanism to retrieve cut specimen samples, crush artifact might be more prominent than is otherwise present when embodiments of the present biopsy device and methods are used.

The internal surface treatments of an outer tube and a hollow, helical inner component, when acting in concert, move materials in a variety of phase states along longitudinally without the need for complex components that would otherwise contribute substantially to the outer caliber dimensions of the present biopsy device. Embodiments comprise a hollow helical transport mechanism that may be both strong and flexible, which continues to function even when distorted by bending. Conventional biopsy devices typically cease to function properly if distorted even slightly. As such, the present biopsy device may be configured to define a curve along its longitudinal axis and would still function properly, with minimal modifications.

Advantageously, a biopsy and coring device, according to embodiments, comprises features configured to perform medical core biopsy procedures or for shaping (such as for vascular applications) or harvesting tissue for other uses. These features comprise structures configured for penetration, coring, part-off, transport and storage of core specimens for medical purposes such as diagnosis and treatment of a variety of diseases and abnormalities. Integral and detachable components may be provided and configured to aspirate fluids for cellular analysis as well as deliver agents at various selectable stages of the procedure. The present biopsy device may be selectable for automatic and/or semi-automatic function, may be used with or without image guidance, and may be compatible with a variety of guidance imaging equipment such as ultrasound, magnetic resonance imaging and X-ray imaging. The present biopsy device may be configured to be disposable and/or recyclable, highly portable, and delivered for use in sterile packaging, typical of medical devices having contact with internal body structures. The present biopsy device may be configured to be minimally invasive. As embodied herein, the present biopsy device comprises several features that may be therapeutic in nature, to be utilized at various stages along the diagnosis/treatment pathway.

While certain embodiments of the disclosure have been described, these embodiments have been presented by way of example only, and are not intended to limit the scope of the disclosure. Indeed, the novel methods, devices and systems described herein may be embodied in a variety of other forms and other applications. For instance, the monolithic beak structures with living hinges, tendon actuation mechanisms and attached actuating sheaths and other mechanisms described herein may find use on a different scale for seek applications, such as robotic arm manipulation and collection systems, so that such a robotic arm would be capable of picking up an object or material, if desired. As another example, the cam and cam follower configurations described in FIGS. 23-26A may find applications such as for internal combustion engine valve configurations, wherein an overhead cam of a special shape acts on a valve stem or extension of a valve stem for instance adorned or other shape. Following the discussion outlined in these last referenced figures, it may be seen that the valves on an internal combustion engine may be extremely finely tuned with respect to dynamics such as initial or staged acceleration/deceleration during opening and closing of the valves. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. An excisional device, comprising:
a sheath comprising a distal scoop-shaped open portion;
a tubular element configured for rotation within the sheath, the tubular element comprising a first proximal spring-like portion; and
an inner tube element configured for rotation and disposed at least partially within the tubular element, the inner tube element comprising an articulable distal assembly configured to core through tissue in an open configuration and part-off cored tissue in a closed configuration and a second proximal spring-like portion that is mechanically coupled to the first proximal spring-like portion to enable limited differential rotation of the inner tube element with respect to the tubular element to cause the articulable distal assembly to selectively assume the open and closed configurations.

2. The excisional device of claim 1, wherein rotating the inner tube element comparatively faster than the tubular element causes the articulable distal assembly to assume the closed configuration.

3. The excisional device of claim 1, wherein rotating the inner tube element comparatively slower than the tubular element causes the articulable distal assembly to assume the open configuration.

4. The excisional device of claim 1, wherein the articulable distal assembly comprises a single articulable member that is configured to bear against the sheath when the articulable distal assembly is in the closed configuration.

5. The excisional device of claim 1, wherein the articulable distal assembly comprises a first articulable member and a second articulable member, the first and second articulable members being configured to bear against each other when the articulable distal assembly is in the closed configuration.

6. The excisional device of claim 1, wherein differential rotation of the inner tube element with respect to the tubular element comprises one of:

the inner tube element lagging in rotation relative to the tubular element; and the inner tube element leading in rotation relative to the tubular element.

7. The excisional device of claim 6, configured such that:

when the inner tube element lags the tubular element in rotation, the articulable distal assembly is caused to assume the open configuration, and when the inner tube element leads the tubular element in rotation, the articulable distal assembly is caused to assume the closed configuration.

8. A method, comprising:

providing a device comprising a sheath comprising a distal scoop-shaped open portion; a tubular element configured for rotation within the sheath, the tubular element comprising a first proximal spring-like portion and an inner tube element configured for rotation and disposed at least partially within the tubular element, the inner tube element comprising an articulable distal assembly and a second proximal spring-like portion that is mechanically coupled to the first proximal spring-like portion;

differentially rotating the inner tube element with respect to the tubular element to selectively control the articulable distal assembly to selectively:

core through tissue with the articulable distal assembly in an open configuration; and part off cored tissue with the articulable distal assembly in a closed configuration.

9. The method of claim 8, wherein differentially rotating comprises rotating the inner tube element comparatively faster than the tubular element to control the articulable distal assembly to assume the closed configuration.

10. The method of claim 8, wherein differentially rotating comprises rotating the inner tube element comparatively slower than the tubular element to control the articulable distal assembly to assume the open configuration.

11. The method of claim 8, wherein providing is carried out with the articulable distal assembly comprising a single articulable member that is configured to bear against the sheath when the articulable distal assembly is in the closed configuration.

12. The method of claim 8, wherein providing is carried out with the articulable distal assembly comprising a first articulable member and a second articulable member, the first and second articulable members being configured to bear against each other when the articulable distal assembly controlled to assume the closed configuration.

13. The method of claim 8, wherein differentially rotating is carried out with an amount of the differential rotation of the inner tube element with respect to the tubular element being limited.

14. The method of claim 8, wherein providing is carried out with the articulable distal assembly being mechanically coupled to the tubular element so as to allow a limited amount of differential rotation of the tubular element relative to the inner tube element.

15. The method of claim 8, wherein differentially rotating the inner tube element with respect to the tubular element comprises one of:

lagging a rotation of the inner tube element relative to a rotation of the tubular element; and leading the rotation of the inner tube element relative to the rotation of the tubular element.

16. The method of claim 8, wherein differentially rotating the inner tube element relative to the tubular element comprises:

lagging a rotation of the inner tube element relative to a rotation of the tubular element to control the articulable distal assembly to assume the open configuration, and leading the rotation of the inner tube element relative to the rotation of the tubular element to control the articulable distal assembly to assume the closed configuration.

* * * * *